United States Patent
Le Poul et al.

(10) Patent No.: US 7,303,889 B2
(45) Date of Patent: Dec. 4, 2007

(54) LIGAND FOR G-PROTEIN COUPLED RECEPTOR GPR43 AND USES THEREOF

(75) Inventors: Emmanuel Le Poul, Brussels (BE); Michel Detheux, Mons (BE); Stéphane Brézillon, Brussels (BE); Vincent Lannoy, Liernu (BE); Marc Parmentier, Beersel (BE)

(73) Assignee: Euroscreen S.A. (BE)

( * ) Notice: Subject to any disclaimer, the term of this patent is extended or adjusted under 35 U.S.C. 154(b) by 495 days.

(21) Appl. No.: 10/337,992

(22) Filed: Jan. 7, 2003

(65) Prior Publication Data

US 2003/0175775 A1    Sep. 18, 2003

Related U.S. Application Data

(60) Provisional application No. 60/346,396, filed on Jan. 7, 2002.

(51) Int. Cl.
 *G01N 33/566* (2006.01)
(52) U.S. Cl. .................. 435/7.21; 435/7.1; 436/501
(58) Field of Classification Search .............. 435/7.21; 436/501
 See application file for complete search history.

(56) References Cited

U.S. PATENT DOCUMENTS

| 5,910,430 A | 6/1999 | Bergsma et al. ........... 435/69.1 |
| 6,180,365 B1 | 1/2001 | Elshourbagy et al. ...... 435/69.1 |

FOREIGN PATENT DOCUMENTS

| WO | WO 98/40483 | 9/1998 |
| WO | WO 99/15656 | 4/1999 |
| WO | WO 00/22129 | 4/2000 |
| WO | WO 00/28083 | 5/2000 |

OTHER PUBLICATIONS

Brunkhorst et al. Propionate Induces Polymorphonuclear Leukocyte Activation and Inhibits Formylmethionyl-Leucyl-Phenylalanin-Stimulated Activation. Infection and Immunity, Jul. 1992, vol. 60, No. 7, pp. 2957-2968.*

Brown et al. The Orphan G Protein-coupled Receptors GPR41 and GPR43 Are Activated by Propionate and Other Short Chain Carboxylic Acids. The Journal of Biological Chemistry, Mar. 28, 2003, vol. 278, No. 13, pp. 11312-11319.*

Le Poul et al. Functional Characterization of Human Receptors for Short Chain Fatty Acids and Their Role in Polymorphonuclear Cell Activation. The Journal of Biological Chemistry, Jul. 11, 2003, vol. 278, No. 28, pp. 25481-25489.*

Downes & Gautam; "The G Protein Subunit Gene Families"; *Genomics*; (1999); 62: 544-552.

Gudermann, et al.; "Receptors and G proteins as primary components of transmembrane signal transduction"; *J. Mol. Med.*; (1995); 73: 51-63.

Sawzdargo, et al.; "A Cluster of Four Novel Human G Protein-Coupled Receptor Genes Occurring in Close Proximity to CD22 Gene on Chromosome 13q13.1"; *Biochemical and Biophysical Research Communications*; (1997); 239: 543-547.

Cummings, et al.; "Short chain fatty acids in human large intestine, portal, hepatic and venous blood"; *Gut*; (1987) 28: 1221-1227.

Bergman; "Energy Contributions of Volatile Fatty Acids from the Gastrointestinal Tract in Various Species"; *Physyciological Reviews*; (1990); 70, 2: 567-590.

Lundquist & Galatius-Jensen; "Quantiative Determination of Amino Acids by Combined Displacement and Paper Chromatrograhy"; *Scandinav. J. Clin. & Lab. Investigation*; (1960); 12: 342-352.

Lodish, et al.; *Molecular Cell Biology* ( *Scientific American Books, Inc.*, New York, NY; (1995); Chpt. 20, pp. 853-925.

* cited by examiner

*Primary Examiner*—John Ulm
(74) *Attorney, Agent, or Firm*—Edwards Angell Palmer & Dodge

(57) ABSTRACT

The present invention is related to the G-protein coupled orphan receptor GPR43 and the identification of short chain fatty acids as natural ligands of the receptor. The invention further relates to assays for the identification of agents that modulate GPR43 ligand binding and signaling activity, as well as compositions consisting essentially of an isolated GPR43 polypeptide and an isolated short chain fatty acid. The invention also relates to diagnostic methods and kits that take advantage of the novel interaction of GPR43 with short chain fatty acids.

26 Claims, 17 Drawing Sheets

Figure 1: Nucleotide (SEQ ID NO: 1) and deduced amino acid (SEQ ID NO: 2) sequence of human GPR43 (AC: O 15552)

```
  1 M   L   P   D   W   K   S   S   L   I   L   M   A   Y   I    15
  1 ATG CTG CCG GAC TGG AAG AGC TCC TTG ATC CTC ATG GCT TAC ATC   45

16 I   I   F   L   T   G   L   P   A   N   L   L   A   L   R    30
 46 ATC ATC TTC CTC ACT GGC CTC CCT GCC AAC CTC CTG GCC CTG CGG   90

31 A   F   V   G   R   I   R   Q   P   Q   P   A   P   V   H    45
 91 GCC TTT GTG GGG CGG ATC CGC CAG CCC CAG CCT GCA CCT GTG CAC  135

46 I   L   L   L   S   L   T   L   A   D   L   L   L   L   L    60
136 ATC CTC CTG CTG AGC CTG ACG CTG GCC GAC CTC CTC CTG CTG CTG  180

61 L   L   P   F   K   I   I   E   A   A   S   N   F   R   W    75
181 CTG CTG CCC TTC AAG ATC ATC GAG GCT GCG TCG AAC TTC CGC TGG  225

76 Y   L   P   K   V   V   C   A   L   T   S   F   G   F   Y    90
226 TAC CTG CCC AAG GTC GTC TGC GCC CTC ACG AGT TTT GGC TTC TAC  270

91 S   S   I   Y   C   S   T   W   L   L   A   G   I   S   I   105
271 AGC AGC ATC TAC TGC AGC ACG TGG CTC CTG GCG GGC ATC AGC ATC  315

106 E   R   Y   L   G   V   A   F   P   V   Q   Y   K   L   S   120
316 GAG CGC TAC CTG GGA GTG GCT TTC CCC GTG CAG TAC AAG CTC TCC  360

121 R   R   P   L   Y   G   V   I   A   A   L   V   A   W   V   135
361 CGC CGG CCT CTG TAT GGA GTG ATT GCA GCT CTG GTG GCC TGG GTT  405

136 M   S   F   G   H   C   T   I   V   I   I   V   Q   Y   L   150
406 ATG TCC TTT GGT CAC TGC ACC ATC GTG ATC ATC GTT CAA TAC TTG  450

151 N   T   T   E   Q   V   R   S   G   N   E   I   T   C   Y   165
451 AAC ACG ACT GAG CAG GTC AGA AGT GGC AAT GAA ATT ACC TGC TAC  495

166 E   N   F   T   D   N   Q   L   D   V   V   L   P   V   R   180
496 GAG AAC TTC ACC GAT AAC CAG TTG GAC GTG GTG CTG CCC GTG CGG  540

181 L   E   L   C   L   V   L   F   F   I   P   M   A   V   T   195
541 CTG GAG CTG TGC CTG GTG CTC TTC TTC ATC CCC ATG GCA GTC ACC  585

196 I   F   C   Y   W   R   F   V   W   I   M   L   S   Q   P   210
586 ATC TTC TGC TAC TGG CGT TTT GTG TGG ATC ATG CTC TCC CAG CCC  630

211 L   V   G   A   Q   R   R   R   R   A   V   G   L   A   V   225
631 CTT GTG GGG GCC CAG AGG CGG CGC CGA GCC GTG GGG CTG GCT GTG  675

226 V   T   L   L   N   F   L   V   C   F   G   P   Y   N   V   240
676 GTG ACG CTG CTC AAT TTC CTG GTG TGC TTC GGA CCT TAC AAC GTG  720

241 S   H   L   V   G   Y   H   Q   R   K   S   P   W   W   R   255
721 TCC CAC CTG GTG GGG TAT CAC CAG AGA AAA AGC CCC TGG TGG CGG  765

256 S   I   A   V   V   F   S   S   L   N   A   S   L   D   P   270
766 TCA ATA GCC GTG GTG TTC AGT TCA CTC AAC GCC AGT CTG GAC CCC  810

271 L   L   F   Y   F   S   S   S   V   V   R   R   A   F   G   285
811 CTG CTC TTC TAT TTC TCT TCT TCA GTG GTG CGC AGG GCA TTT GGG  855

286 R   G   L   Q   V   L   R   N   Q   G   S   S   L   L   G   300
856 AGA GGG CTG CAG GTG CTG CGG AAT CAG GGC TCC TCC CTG TTG GGA  900

301 R   R   G   K   D   T   A   E   G   T   N   E   D   R   G   315
901 CGC AGA GGC AAA GAC ACA GCA GAG GGG ACA AAT GAG GAC AGG GGT  945

316 V   G   Q   G   E   M   P   S   S   D   F   T   T   E   330
946 GTG GGT CAA GGA GAA GGG ATG CCA AGT TCG GAC TTC ACT ACA GAG  990

331 *                                                             331
991 TAG                                                           993
```

Figure 2: Alignment of GPR43.
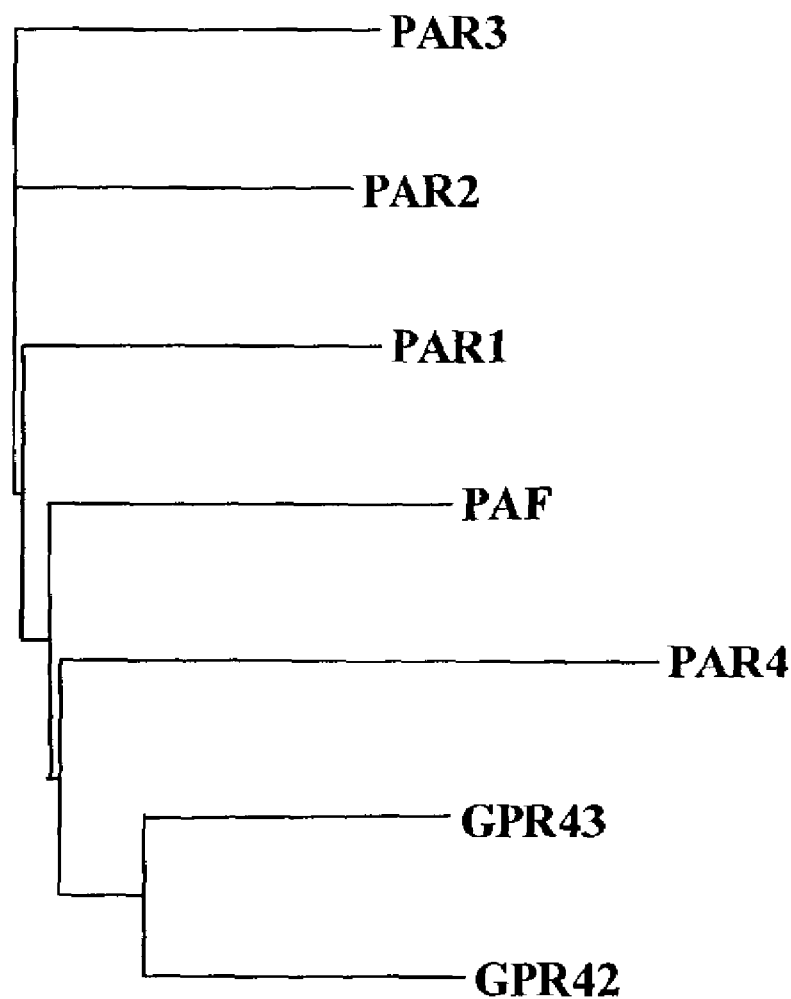

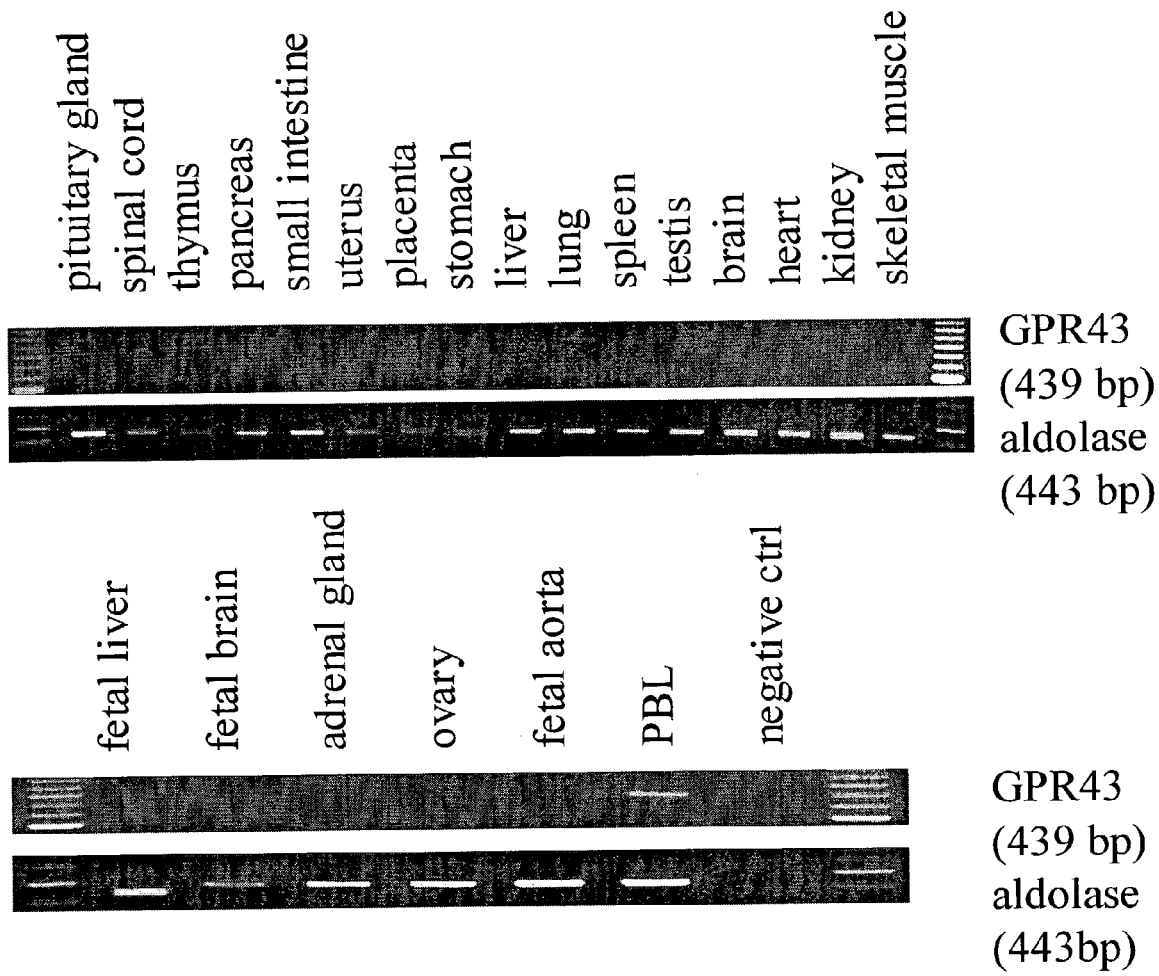
Figure3: Tissue distribution of GPR43 in human tissues, using RT-PCR

Figure 12

Short Fatty Carboxylic Acids (SFCA) and analogues formula and activity on human GPR43

| R | SFCA | activity |
|---|---|---|
| H | formate | weak active |
| CH3 | acetate | very active |
| Cl3C | trichloroacetate | very weak active |
| C2H5 | propionate | very active |
| CH3-CO | pyruvate | very weak active |
| C3H7 | n-butyrate | active |
|  | isobutyrate | active |
| CH3-CO-CH2 | acetoacetate | very weak active |
| C4H9 | n-valerate | active |
| C5H11 | n-caproate | active |

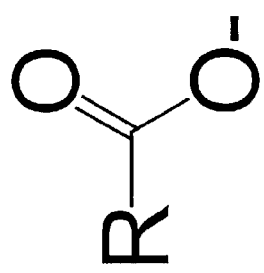

Figure 13 : Tissular distribution of human GPR43 receptor using semi-quantitative RT-PCR.
A.
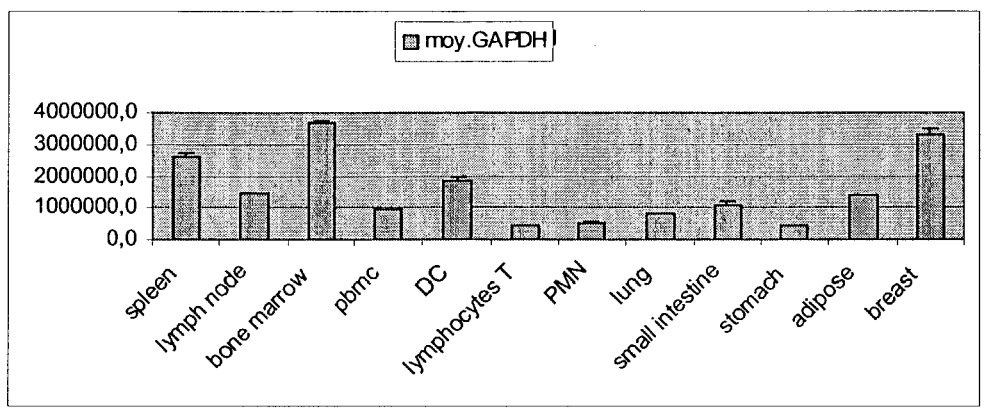
B.
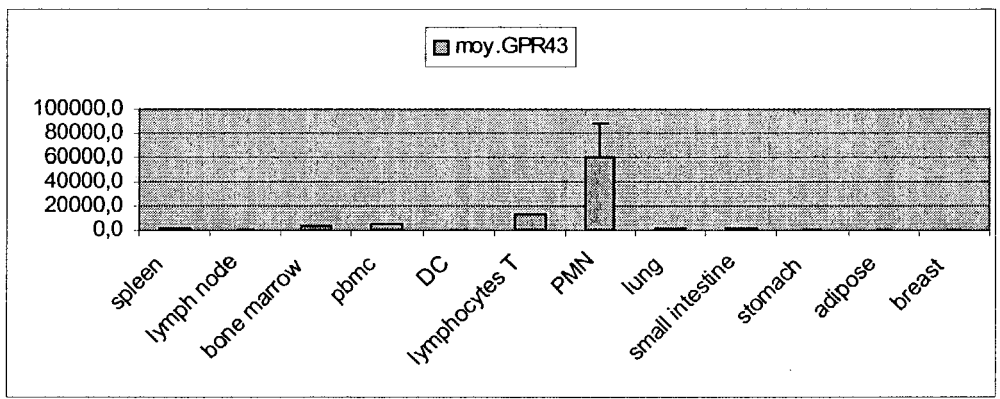
C.
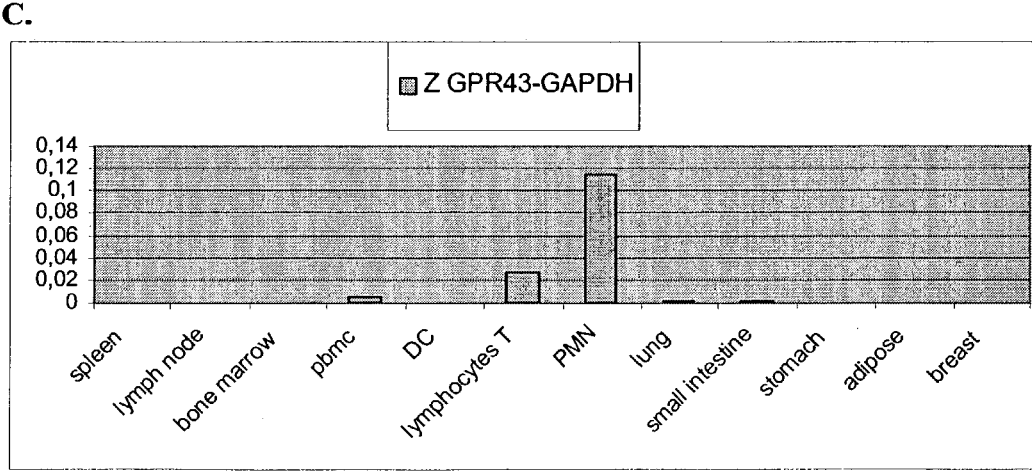

kinetic plot of increase of intracellular calcium in PMN for varying concentration of Na propionate.

Injection with increasing concentration of acetate leads to a concentration-dependent increase of intracellular calcium Figure 17 : Neutrophil chemotaxis induced by SCFA.
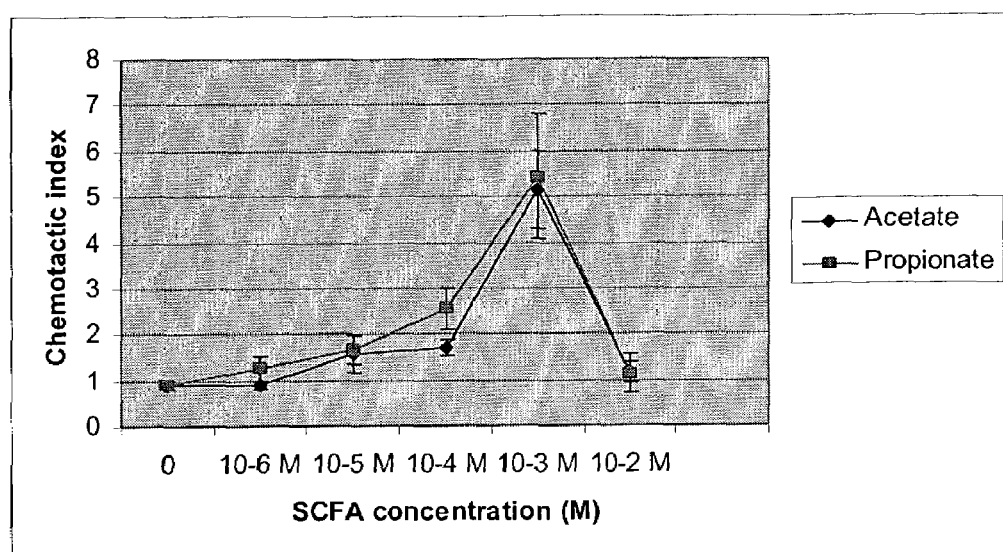
Neutrophil migration in response to increasing concentrations of SCFA (acetate and propionate) is reported as a migration index. The chemotaxis data represent mean and SEM of 5 independent experiments

US 7,303,889 B2

LIGAND FOR G-PROTEIN COUPLED RECEPTOR GPR43 AND USES THEREOF

PRIORITY

This application claims priority under 35 U.S.C. §119(e) to U.S. Provisional Application No. 60/346,396, filed Jan. 7, 2002.

FIELD OF THE INVENTION

The present invention is related to the natural ligand for an orphan G protein coupled receptor and methods of use.

BACKGROUND OF THE INVENTION AND STATE OF THE ART

G-protein coupled receptors (GPCRs) are proteins responsible for transducing a signal within a cell. GPCRs have usually seven transmembrane domains. Upon binding of a ligand to an extra-cellular portion or fragment of a GPCR, a signal is transduced within the cell that results in a change in a biological or physiological property or behaviour of the cell. GPCRs, along with G-proteins and effectors (intracellular enzymes and channels modulated by G-proteins), are the components of a modular signalling system that connects the state of intra-cellular second messengers to extra-cellular inputs.

GPCR genes and gene products can modulate various physiological processes and are potential causative agents of disease. The GPCRs seem to be of critical importance to both the central nervous system and peripheral physiological processes.

The GPCR protein superfamily is represented in five families: Family I, receptors typified by rhodopsin and the beta2-adrenergic receptor and currently represented by over 200 unique members; Family II, the parathyroid hormone/calcitonin/secretin receptor family; Family III, the metabotropic glutamate receptor family, Family IV, the CAMP receptor family, important in the chemotaxis and development of *D. discoideum*; and Family V, the fungal mating pheromone receptor such as STE2.

G proteins represent a family of heterotrimeric proteins composed of α, β and γ subunits, that bind guanine nucleotides. These proteins are usually linked to cell surface receptors (receptors containing seven transmembrane domains) for signal transduction. Indeed, following ligand binding to the GPCR, a conformational change is transmitted to the G protein, which causes the α-subunit to exchange a bound GDP molecule for a GTP molecule and to dissociate from the βγ-subunits.

The GTP-bound form of the α, β and γ-subunits typically functions as an effector-modulating moiety, leading to the production of second messengers, such as cAMP (e.g. by activation of adenyl cyclase), diacylglycerol or inositol phosphates.

Greater than 20 different types of α-subunits are known in humans. These subunits associate with a small pool of β and γ subunits. Examples of mammalian G proteins include Gi, Go, Gq, Gs and Gt. G proteins are described extensively in Lodish et al., *Molecular Cell Biology* (Scientific American Books Inc., New York, N.Y., 1995; and also by Downes and Gautam, 1999, The G-Protein Subunit Gene Families. *Genomics* 62:544-552), the contents of both of which are incorporated herein by reference.

Known and uncharacterized GPCRs currently constitute major targets for drug action and development. There are ongoing efforts to identify new G protein coupled receptors which can be used to screen for new agonists and antagonists having potential prophylactic and therapeutic properties.

More than 300 GPCRs have been cloned to date, excluding the family of olfactory receptors. Mechanistically, approximately 50-60% of all clinically relevant drugs act by modulating the functions of various GPCRs (Cudermann et al., *J. Mol. Med.*, 73:51-63, 1995).

GPR43 is a member of the rhodopsin like receptors family, cloned in 1997. It shows a homology of 38% with another orphan GPCR, GPR41 and 27% with transmembrane domains of mouse PAR1 receptor. The gene encoding GPR43 coding gene is located on human chromosome 19q31 (Sawzdargo et al., 1997). GPR43 has been described as a gene induced by IL-9 in mouse cytokine dependent T helper cell lines and bone marrow derived primary mast cells. In addition, GPR43 mRNA transcription is stimulated in the lung, intestine and stomach of transgenic mice over-expressing IL-9. GPR43 mRNA is also induced in splenoytes by mitogens, such as concanavalin A, and this induction is blocked by aminosterol compounds (see WO99/15656). GPR43 polynucleotide and amino acid sequences are disclosed in U.S. Pat. Nos. 5,910,430 and 6,180,365B1 and in WO00/28083, WO98/40483, WO99/15656 and WO00/22129, each of which is incorporated herein by reference.

Short chain fatty acids (SCFA) include but are not limited to acetate, propionate, butyrate and valerate. SCFA are produced by microbial fermentation in the hindgut in considerable amounts. Most of the anions in hindgut contents are SCFA, mainly acetate, propionate and butyrate. SCFA are rapidly absorbed, and the total SCFA concentration in peripheral blood reaches 79 μM (Cummings, 1987). Among the different SCFAs, acetate is the principal anion and can also be produced in different tissues by biochemical synthesis (Bergman, 1990). Acetate is present in the plasma at a concentration of 59 to 85 μM and its concentration can be increased by 20 fold after ethanol administration (Lundquist et al., 1960). It is believed that most plasma acetate is derived from the splanchnic bed and is used by other tissues where it can account for almost 7% of basal energy expenditure. Butyrate is produced by bacterial fermentation of dietary fibers in the colon lumen, and dramatically affects the proliferation of colon cancer cells in vitro experiments. Various periodontal and root canal pathogens, such as the Bacteroides species, can produce significant amounts of short chain fatty acids. (SCFA). Short-chain fatty acids are also physiological regulators of growth and differentiation in the gastrointestinal tract and can act as antibacterial agents. There is some evidence that SCFA metabolism is involved in the development of colitis ulcerosa, diverticulosis and colorectal cancer. The differences between the effects of SCFA on cell proliferation, differentiation and apoptosis of colonocytes in vivo and in vitro indicate that in addition to direct effects of SCFA, systemic effects such as neural and humoral factors are also of crucial importance. The opposing effects of SCFA on proliferation and apoptosis in normal colonocytes and in colon cancer cells demonstrate possibilities for prevention and/or therapy of colonic diseases.

SUMMARY OF THE INVENTION

The invention is based on the discovery that short chain fatty acids (SCFAs) are natural ligands of the orphan receptor GPR43. This invention thus relates to the SCFA ligand/receptor (identified hereafter as SEQ ID NO. 2) pair, and to functional homologs of the receptor which also bind SCFAs and cells transformed by a vector comprising the nucleotide sequence encoding the receptor (SEQ ID NO: 1) in combination with the SCFA ligand. The invention also relates to a composition consisting essentially of an isolated GPR43 polypeptide and an isolated SCFA, as well as to methods of identifying agents that modulate the activities of GPR43 polypeptides. The methods are useful for the identification of agonist, inverse agonist or antagonist compounds useful for the development of new drugs. The interaction of GPR43 with SCFAs is also useful for the development of diagnostics for diseases related to GPR43 activity.

The invention encompasses a method of identifying an agent that modulates the function of GPR43, the method comprising: a) contacting a GPR43 polypeptide with a short chain fatty acid in the presence and absence of a candidate modulator under conditions permitting the binding of the short chain fatty acid to the GPR43 polypeptide; and b) measuring binding of the GPR43 polypeptide to the short chain fatty acid wherein a decrease in binding in the presence of the candidate modulator, relative to binding in the absence of the candidate modulator, identifies the candidate modulator as an agent that modulates the function of GPR43.

The invention further encompasses a method of detecting, in a sample, the presence of an agent that modulates the function of GPR43, the method comprising: a) contacting a GPR43 polypeptide with a short chain fatty acid in the presence and absence of the sample under conditions permitting the binding of the short chain fatty acid to the GPR43 polypeptide; and b) measuring binding of the GPR43 polypeptide to the short chain fatty acid wherein a decrease in binding in the presence of the sample, relative to binding in the absence of the sample, indicates the presence, in the sample of an agent that modulates the function of GPR43.

In one embodiment of either of the preceding methods, the measuring is performed using a method selected from label displacement, surface plasmon resonance, fluorescence resonance energy transfer, fluorescence quenching, and fluorescence polarization.

The invention further encompasses a method of identifying an agent that modulates the function of GPR43, the method comprising: a) contacting a GPR43 polypeptide with a short chain fatty acid in the presence and absence of a candidate modulator; and b) measuring a signalling activity of the GPR43 polypeptide, wherein a change in the activity in the presence of the candidate modulator relative to the activity in the absence of the candidate modulator identifies the candidate modulator as an agent that modulates the function of GPR43.

The invention further encompasses a method of identifying an agent that modulates the function of GPR43, the method comprising: a) contacting a GPR43 polypeptide with a candidate modulator; b) measuring a signalling activity of the GPR43 polypeptide in the presence of the candidate modulator; and c) comparing the activity measured in the presence of the candidate modulator to the activity measured in a sample in which the GPR43 polypeptide is contacted with a short chain fatty acid at its $EC_{50}$, wherein the candidate modulator is identified as an agent that modulates the function of GPR43 when the amount of the activity measured in the presence of the candidate modulator is at least 20% of the amount induced by the short chain fatty acid present at its $EC_{50}$.

The invention further encompasses a method of detecting the presence, in a sample, of an agent that modulates the function of GPR43, the method comprising: a) contacting a GPR43 polypeptide with short chain fatty acid in the presence and absence of the sample; b) measuring a signalling activity of the GPR43 polypeptide; and c) comparing the amount of the activity measured in a reaction containing GPR43 and short chain fatty acid without the sample to the amount of the activity measured in a reaction containing GPR43, short chain fatty acid and the sample, wherein a change in the activity in the presence of the sample relative to the activity in the absence of the sample indicates the presence, in the sample, of an agent that modulates the function of GPR43.

The invention further encompasses a method of detecting the presence, in a sample, of an agent that modulates the function of GPR43, the method comprising: a) contacting a GPR43 polypeptide with the sample; b) measuring a signalling activity of the GPR43 polypeptide in the presence of the sample; and c) comparing the activity measured in the presence of the sample to the activity measured in a reaction in which the GPR43 polypeptide is contacted with a short chain fatty acid present at its $EC_{50}$, wherein an agent that modulates the function of GPR43 is detected if the amount of the activity measured in the presence of the sample is at least 20% of the amount induced by the short chain fatty acid present at its $EC_{50}$.

In one embodiment of each of the preceding methods, the short chain fatty acid is detectably labeled. In a preferred embodiment, the short chain fatty acid is detectably labeled with a moiety selected from the group consisting of a radioisotope, a fluorophore, a quencher of fluorescence, an enzyme, and an affinity tag.

In an embodiment of each of the preceding methods, the contacting is performed in or on a cell expressing the GPR43 polypeptide.

In an embodiment of each of the preceding methods the contacting is performed in or on synthetic liposomes.

In an embodiment of each of the preceding methods the contacting is performed in or on virus-induced budding membranes containing a GPR43 polypeptide.

In an embodiment of each of the preceding methods the contacting is performed using a membrane fraction from cells expressing the GPR43 polypeptide.

In an embodiment of each of the preceding methods the agent is selected from the group consisting of a natural or synthetic peptide or polypeptide, an antibody or antigen-binding fragment thereof, a lipid, a carbohydrate, a nucleic acid, and a small organic molecule.

In one embodiment of the methods wherein a signalling activity is measured, the step of measuring a signalling activity of the GPR43 polypeptide comprises detecting a change in the level of a second messenger.

In another embodiment of the methods wherein a signalling activity is measured, the step of measuring a signalling activity comprises measurement of guanine nucleotide binding or exchange, adenylate cyclase activity, cAMP, Protein Kinase C activity, phosphatidylinositol breakdown, diacylglycerol, inositol triphosphate, intracellular calcium, arachinoid acid, MAP kinase activity, tyrosine kinase activity, or reporter gene expression.

In one embodiment, the step of measuring a signalling activity comprises using an aequorin-based assay.

The invention further comprises a method of modulating the activity of a GPR43 polypeptide in a cell, the method comprising the step of delivering to the cell an agent that modulates the activity of a GPR43 polypeptide, such that the activity of GPR43 is modulated.

The invention further encompasses a method of diagnosing a disease or disorder characterized by dysregulation of GPR43 signalling, the method comprising: a) contacting a tissue sample with an antibody specific for a GPR43 polypeptide; b) detecting binding of the antibody to the tissue sample; and c) comparing the binding detected in step (b) with a standard, wherein a difference in binding relative to the standard is diagnostic of a disease or disorder characterized by dysregulation of GPR43.

The invention further encompasses a method of diagnosing a disease or disorder characterized by dysregulation of GPR43 signalling, the method comprising: a) isolating nucleic acid from a tissue sample; b) amplifying a GPR43 polynucleotide, using the nucleic acid as a template; and c) comparing the amount of amplified GPR43 polynucleotide produced in step (b) with a standard, wherein a difference in the amount of amplified GPR43 polynucleotide relative to the standard is diagnostic of a disease or disorder characterized by dysregulation of GPR43.

The invention further encompasses a method of diagnosing a disease or disorder characterized by dysregulation of GPR43 signalling, the method comprising: a) isolating nucleic acid from a tissue sample; b) amplifying a GPR43 polynucleotide, using the nucleic acid as a template; and c) comparing the sequence of the amplified GPR43 polynucleotide produced in step (b) with a standard, wherein a difference in the sequence, relative to the standard is diagnostic of a disease or disorder characterized by dysregulation of GPR43. In one embodiment, the step of amplifying comprises RT/PCR. In another embodiment, the standard is SEQ ID NO: 1. In another embodiment, the step of comparing the sequence comprises minisequencing. In another embodiment, the step of comparing the amount is performed using a microarray.

The invention further encompasses a composition consisting essentially of an isolated GPR43 polypeptide and an isolated short chain fatty acid. An isolated GPR43 polypeptide and an isolated short chain fatty acid together can form a complex that is useful for the identification of agents that modulate their interaction, the identification of agents that modulate the activity of GPR43 polypeptides, and the identification of individuals suffering from a disease or disorder mediated by or involving GPR43. Complexed or uncomplexed (i.e., bound or unbound) isolated GPR43 polypeptide and isolated short chain fatty acid is thus the essential element or basis of the assays and methods of the invention. The composition "consisting essentially of" an isolated GPR43 polypeptide and an isolated short chain fatty acid can comprise additional components, however, such additional components are not essential to the novel interaction upon which the invention is based. The composition "consisting essentially of" an isolated GPR43 polypeptide and an isolated short chain fatty acid is distinct from and excludes naturally occurring complexes between GPR43 polypeptides and short chain fatty acids, present e.g., in cells, tissues or in cell or tissue extracts. The composition of the invention is also distinct from and excludes complexes between GPR43 polypeptides expressed from recombinant constructs and naturally-occurring short chain fatty acids.

The invention further encompasses a kit comprising an isolated GPR43 polypeptide and an isolated short chain fatty acid or salt thereof. In one embodiment, the short chain fatty acid or salt thereof is linear. In another embodiment, the short chain fatty acid or salt thereof is branched. In another embodiment, one or more non-carbonyl carbons in the short chain fatty acid or salt thereof is substituted with a non-carbon-containing substituent. In another embodiment, the short chain fatty acid salt is selected from the group consisting of sodium butyrate, sodium propionate, sodium acetate, sodium valerate and sodium formate.

The invention further encompasses a kit comprising an isolated polynucleotide encoding a GPR43 polypeptide and an isolated short chain fatty acid salt. In one embodiment, the short chain fatty acid or salt thereof is linear. In another embodiment, the short chain fatty acid or salt thereof is branched. In another embodiment, one or more non-carbonyl carbons in the short chain fatty acid or salt thereof is substituted with a non-carbon-containing substituent. In another embodiment, the short chain fatty acid salt is selected from the group consisting of sodium butyrate, sodium propionate, sodium acetate, sodium valerate and sodium formate.

The invention further encompasses a kit comprising a cell transformed with a polynucleotide encoding a GPR43 polypeptide and an isolated short chain fatty acid or salt thereof. In one embodiment, the short chain fatty acid or salt thereof is linear. In another embodiment, the short chain fatty acid or salt thereof is branched. In another embodiment, one or more non-carbonyl carbons in the short chain fatty acid or salt thereof is substituted with a non-carbon-containing substituent. In another embodiment, the short chain fatty acid salt is selected from the group consisting of sodium butyrate, sodium propionate, sodium acetate, sodium valerate and sodium formate.

The invention further encompasses a kit comprising a cellular membrane fraction comprising a GPR43 polypeptide, and packaging materials therefor. In one embodiment, the kit further comprises an isolated short chain fatty acid or salt thereof. In one embodiment, the short chain fatty acid or salt thereof is linear. In another embodiment, the short chain fatty acid or salt thereof is branched. In another embodiment, one or more non-carbonyl carbons in the short chain fatty acid or salt thereof is substituted with a non-carbon-containing substituent. In another embodiment, the short chain fatty acid salt is selected from the group consisting of sodium butyrate, sodium propionate, sodium acetate, sodium valerate and sodium formate.

Kits according to the invention are useful, for example, for screening for agents that modulate the activity of GPR43, identifying the presence of an agent that modulates GPR43 in a sample, or for diagnosis of a disease or disorder characterized by dysregulation of GPR43. Kits according to the invention will additionally comprise packaging materials necessary for such kits. Kits according to the invention can additionally comprise a standard. In one embodiment, the standard is a sample from an individual not affected by a disease or disorder characterized by dysregulation of GPR43.

As used herein, the term "GPR43 polypeptide" refers to a polypeptide having two essential properties: 1) a GPR43 polypeptide has at least 80% amino acid identity, preferably 85%, 90%, 95%, or higher, up to and including 100% identity, with SEQ ID NO. 2; and 2) a GPR43 polypeptide has GPR43 activity including either or both of GPR43 ligand binding activity (wherein SCFA ligands bind with affinity at least equivalent to acetate or propionate binding) or GPR43 signalling activity as defined herein.

As used herein, "GPR43 activity" refers to SCFA binding to or signalling by a GPR43 polypeptide as defined herein. A polypeptide that has "GPR43 activity" will bind to acetate and propionate with an affinity that is at least 100-fold greater than that of formate.

A homologous sequence (which may exist in other mammal species or specific groups of human populations), where homology indicates sequence identity, means a sequence which presents a high sequence identity (more than 80%, 85%, 90%, 95% or 98% sequence identity) with the complete human nucleotide or amino acid sequence of SEQ ID NO: 2. A functional homolog is characterized by the ability to bind a short chain fatty acid ligand as defined herein or by the ability to initiate or propagate a signal in response to ligand binding, or both. A functional homolog will bind natural ligands of wt GPR43 with affinity as follows: propionate=acetate>butyrate>formate, where propionate and acetate bind with at least 100×greater affinity than formate.

Homologous sequences of a sequence according to the invention may include an amino acid or nucleotide sequence encoding a similar receptor which exists in other animal species (rat, mouse, cat, dog, etc.) or in specific human population groups, but which are involved in the same biochemical pathway.

Such homologous sequences may comprise additions, deletions or substitutions of one or more amino acids or nucleotides, which do not substantially alter the functional characteristics of the receptor according to the invention. That is, homologs will have at least 90% of the activity of wt full length human GPR43 and will bind acetate and propionate with at least 100×greater affinity than formate.

Such homologous sequences can also be nucleotide sequences of more than 400, 600, 800 or 1000 nucleotides which are able to hybridize to the complete human GPR43 sequence under stringent hybridisation conditions (such as the ones described by SAMBROOK et al., Molecular Cloning, Laboratory Manuel, Cold Spring, Harbor Laboratory press, N.Y.). An example of "stringent hybridization conditions" is as follows: hybridize in 50% formamide, 5×SSC, 50 mM sodium phosphate (pH 6.8), 0.1% sodium pyrophosphate, 5× Denhardt's solution, 50 µg/ml sonicated salmon sperm DNA, 0.1% SDS and 10% dextran sulfate at 42° C.; and wash at 42° C. (or higher, e.g., up to two degrees C. below the $T_m$ of the perfect complement of the probe sequence) in 0.2×SSC and 0.1% SDS.

As used herein, the term "GPR43 signalling activity" refers to the initiation or propagation of signalling by a GPR43 polypeptide. GPR43 signalling activity is monitored by measuring a detectable step in a signalling cascade by assaying one or more of the following: stimulation of GDP for GTP exchange on a G protein; alteration of adenylate cyclase activity; protein kinase C modulation; phosphatidylinositol breakdown (generating second messengers diacylglycerol, and inositol triphosphate); intracellular calcium flux; activation of MAP kinases; modulation of tyrosine kinases; or modulation of gene or reporter gene activity. A detectable step in a signalling cascade is considered initiated or mediated if the measurable activity is altered by 10% or more above or below a baseline established in the substantial absence of a SCFA relative to any of the GPR43 activity assays described herein below. The measurable activity can be measured directly, as in, for example, measurement of cAMP or diacylglycerol levels. Alternatively, the measurable activity can be measured indirectly, as in, for example, a reporter gene assay.

As used herein, the terms "short chain fatty acid" and "short fatty carobxylic acid" refer to a molecule of the general structure $C_xH_{(2x+1)}$—COO wherein x is 0 to 5, or to related molecules in which non-carbon-containing substitutents, including, for example, OH, $NH_3$, $PO_4$, O, and halogens are branched on the carbonyl chain. An SCFA according to the invention can be linear or branched, saturated or unsaturated. An SCFA according to the invention will bind to a GPR43 polypeptide as defined herein with an affinity at least equivalent to acetate or propionate and at least 100×stronger than formate. An SCFA according to the invention may additionally stimulate a GPR43 signalling activity. Examples of SCFA include, but are not limited to acetate, propionate, n-buyrate, n-pentanoate (valerate) and formate. Examples of SCFAs according to the invention and their relative activity on GPR43 are shown in FIG. 12.

As used herein, the term "detectable step" refers to a step that can be measured, either directly, e.g., by measurement of a second messenger or detection of a modified (e.g., phosphorylated) protein, or indirectly, e.g., by monitoring a downstream effect of that step. For example, adenylate cyclase activation results in the generation of cAMP. The activity of adenylate cyclase can be measured directly, e.g., by an assay that monitors the production of cAMP in the assay, or indirectly, by measurement of actual levels of cAMP.

Preferably, a recombinant cell according to the invention is a recombinant cell transformed by a plasmid, cosmid or viral vector, preferably a baculovirus, an adenovirus, or a semliki forest virus, and the cell is preferably selected from the group consisting of bacterial cells, yeast cells, insect cells or mammal cells.

According to a preferred embodiment of the present invention, the cell is selected from the group consisting of COS-7 cells, a CHO cell, a LM (TK–) cell, a NIH-3T3 cell, HEK-293 cell, K-562 cell or a 1321N1 astrocytoma cell. Other transfectable cell lines are also useful, however. Preferably, the vector comprises regulatory elements operatively linked to the polynucleotide sequence encoding the receptor according to the invention, so as to permit expression thereof.

Another aspect of the present invention is related to the use of a specific active portion of the sequences. As used herein, an "active portion" refers to a portion of a sequence that is of sufficient size to exhibit normal or near normal pharmacology (e.g., receptor activity (as defined herein), the response to an activator or inhibitor, or ligand binding are at least 90% of the level of activity, response, or binding exhibited by a wild type receptor). "A portion" as it refers to a sequence encoding a receptor, refers to less than 100% of the sequence (i.e., 99, 90, 80, 70, 60, 50% etc . . . ). The active portion could be a receptor which comprises a partial deletion of the complete nucleotide or amino acid sequence and which still maintains the active site(s) and protein domain(s) necessary for the binding of and interaction with a specific ligand, preferably acetate and propionate.

In another embodiment of any of the preceding methods, the contacting is performed in or on synthetic liposomes (Mirzabekov et al., 2000) or virus-induced budding membranes containing a GPR43 polypeptide. (see Patent application WO0102551, Virus-like particles, their Preparation and their Use preferably in Pharmaceutical Screening and Functional Genomics (2001) incorporated herein by reference).

As used herein, "ligand" refers to a moiety that is capable of associating or binding to a receptor. According to the method of the invention, a ligand and a receptor have a binding constant that is sufficiently strong to allow detection of binding by an assay method that is appropriate for detection of a ligand binding to a receptor (e.g. a second messenger assay to detect an increase or decrease in the production of a second messenger in response to ligand binding to the receptor, a binding assay to measure protein-ligand binding or an immunoassay to measure antibody-antigen interactions). A ligand according to the invention includes the actual molecule that binds a receptor (e.g.

propionate is the ligand for GPR43) or a ligand may be any nucleotide, antibody, antigen, enzyme, peptide, polypeptide or nucleic acid capable of binding to the receptor. A ligand is preferably a short chain carboxylic acid but can also include a polypeptide, a peptide or a nucleic acid sequence. According to the method of the invention, a ligand and receptor specifically bind to each other (e.g. via covalent or hydrogen bonding or via an interaction between, for example, a protein and a ligand, an antibody and an antigen or protein subunits).

Another aspect of the present invention is related to a method for the screening, detection and recovery of candidate modulators of a receptor of the invention comprising the steps of: contacting a cell expressing GPR43 with an SCFA under conditions which permit binding of acetate or propionate to GPR43, in the presence of the candidate modulator, performing a second messenger assay, and comparing the results of the second messenger assay obtained in the presence and absence of the candidate modulator.

Another aspect of the present invention is related to a method for the screening, detection and possible recovery of candidate modulators of a receptor of the invention comprising the steps of: contacting a cell membrane expressing GPR43 with an SCFA under conditions which permit binding of acetate or propionate to GPR43, performing a second messenger assay, and comparing the results of the second messenger assay obtained in the presence and absence of the candidate modulator.

In another embodiment, the step of measuring a signalling activity of the GPR43 polypeptide comprises detecting a change in the level of a second messenger.

A further aspect of the present invention is related to the unknown agonist and/or antagonist compounds identified and/or recovered by the method of the invention, as well as to a diagnostic kit comprising the (unknown) compounds or a pharmaceutical composition (including a vaccine) comprising an adequate pharmaceutical carrier and a sufficient amount of the (unknown) compound.

An antagonist compound according to the invention means a molecule or a group of molecules able to bind to the receptor according to the invention and block the binding of natural compounds (propionate or acetate or related short chain carboxylic acids).

The invention further encompasses a method of diagnosing a disease or disorder characterized by dysregulation of GPR43 signalling, the method comprising: a) contacting a tissue sample with an antibody specific for a GPR43 polypeptide and an antibody specific for a GPR43 ligand; b) detecting binding of the antibodies to the tissue sample; and c) comparing the binding detected in step (b) with a standard, wherein a difference in binding of either antibody or both, relative to the standard, is diagnostic of a disease or disorder characterized by dysregulation of GPR43

The invention further encompasses a method of diagnosing a disease or disorder characterized by dysregulation of GPR43 signalling, the method comprising: a) isolating a tissue sample; b) measuring the concentration of SCFA; and c) comparing the amount of SCFA measured in step (b) with a standard, wherein a difference in the amount of SCFA relative to the standard is diagnostic of a disease or disorder characterized by dysregulation of GPR43.

A further aspect of the present invention is related to a non-human mammal comprising a homozygous null mutation (homozygous "knock-out") of the polynucleotide sequence encoding the GPR43 receptor according to the invention, or a transgenic non-human mammal that over expresses a GPR43 polypeptide above the natural level of expression. As used herein. "above the natural level of expression" refers to a level that is at least 2-fold, preferably 5-fold, more preferably 10-fold and most preferably 100-fold or more (i.e., 150-fold, 200-fold, 250-fold, 500-fold, 1000-fold, 10,000-fold etc.) as compared to the level of expression of the endogenous receptor in its normal native context. A transgenic non-human mammal according to the invention will express the transgene in at least one tissue or cell type but can express the GPR43 transgene in all tissues and cells. A transgenic non-human mammal can be obtained by a method well known by a person skilled in the art, for instance, as described in document WO 98/20112 using the classical technique based upon the transfection of embryonic stem cells, preferably according to the method described by Carmeliet et al. (Nature, Vol.380, p.435-439, 1996).

"Gene targeting" is a type of homologous recombination that occurs when a fragment of genomic DNA is introduced into a mammalian cell and that fragment locates and recombines with endogenous homologous sequences as exemplified in U.S. Pat. No. 5,464,764, and U.S. Pat. No. 5,777,195, the contents of which are hereby incorporated by reference herein in their entireties. As used herein the term "transgenic animal" refers to a non-human animal in which one or more, and preferably essentially all, of the cells of the animal contain a transgene introduced by way of human intervention, such as by transgenic techniques known in the art. The transgene can be introduced into the cell, directly or indirectly by introduction into a precursor of the cell, by way of deliberate genetic manipulation, such as by microinjection or by infection with a recombinant virus.

Preferably, the transgenic non-human mammal overexpressing the polynucleotide encoding the GPR43 receptor according to the invention comprises the polynucleotide incorporated in a DNA construct with an inducible promoter allowing the overexpression of the receptor and possibly also tissue and cell-specific regulatory elements.

In one embodiment, the kits according to the invention comprise reagents for measuring the binding of a short chain fatty acid to a GPR43 polypeptide. In another embodiment, the kit comprises reagents for measuring a signalling activity of a GPR43 polypeptide.

In one embodiment, a screening or diagnostic kit according to the invention includes a GPR43 receptor polypeptide or a cellular membrane preparation comprising a GPR43 polypeptide and one or more SCFAs in separate containers. Such kits can additionally comprise all the necessary means and media for performing a detection of specific binding (for example of propionate) to the GPR43 receptor according to the invention. Binding or signalling activity can be correlated with a method of monitoring one or more of the symptoms of the diseases described hereafter.

The diagnostic kits can thus further comprise elements necessary for a specific diagnostic measurement, or, for example, the measurements of bound compounds using high throughput screening techniques known to the person skilled in the art, e.g., the techniques described in WO 00/02045. Such kits can be used, e.g. to monitor dosage and effectiveness of GPR43 modulating agents used for treatment. The high throughput screening diagnostic dosage and monitoring can be performed by using various solid supports, such as microtiter plates or biochips selected by the person skilled in the art.

In a pharmaceutical composition according to the invention, the adequate pharmaceutical carrier is a carrier of solid, liquid or gaseous form, which can be selected by the person skilled in the art according to the type of administration and the possible side effects of the compound administered to modulate GPR43 activity. The pharmaceutical carrier useful according to the invention does not include tissue culture medium or other media comprising serum. The ratio between the pharmaceutical carrier and the specific compound can be selected by the person skilled in the art according to the patient treated, the administration and the possible side effects of the compound, as well as the type of disease of disorder treated or sought to be prevented.

The pharmaceutical composition finds advantageous applications in the field of treatment and/or prevention of various diseases or disorders, preferably selected from the group consisting of ostatic hypertrophy, migraine, vomiting, psychotic and neurological disorders, including anxiety, schizophrenia, manic depression, depression, delirium, dementia and severe mental retardation, degenerative diseases, neurodegenerative diseases such as Alzheimer's disease or Parkinson's disease, and dyskinasias, such as Huntington's disease or Gilles de la Tourett's syndrome and other related diseases including thrombosis and other cardiovascular diseases, autoimmune and inflammatory diseases.

Among the mentioned diseases the preferred applications are related to therapeutic agents targeting 7TM receptors that can play a function in preventing, improving or correcting dysfunctions or diseases, including, but not limited to fertility, fetal development, infections such as bacterial, fungal, protozoan and viral infections, particularly infections caused by HIV1 and HIV2, pain, cancer, anorexia, bulimia, asthma, Parkinson's disease, acute heart failure, hypertension, urinary retention, osteoporosis, angina pectoris, myocardial infarction, ulcers, asthma, allergies, benign prostatic hypertrophy, psychotic and neurological disorders including anxiety, depression, migraine, vomiting, stroke, schizophrenia, manic depression, delirium, dementia, severe mental retardation and dyskinesias, such as Huntington's disease or Gilles de la Tourette's syndrome including thrombosis and other cardiovascular diseases, autoimmune and inflammatory diseases.

The present invention also provides a method of modulating PMN chemotaxis in a mammal comprising contacting PMN cells bearing the cell surface receptor GPR43 with a modulator of GPR43 signalling activity, sufficient to modulate said PMN chemotaxis.

In one embodiment, the present invention provides a method of modulating PMN chemotaxis in a patient in need thereof, comprising administering to the patient, an inhibitor of GPR43 signalling activity.

In one embodiment, PMN chemotaxis is decreased by contacting said PMN cell with an inhibitor of GPR43 signalling activity.

In one embodiment, PMN chemotaxis is decreased by contacting said PMN cell with an antagonist of GPR43 signalling activity.

In a further embodiment, PMN chemotaxis is increased by contacting said PMN cell with an agonist of GPR43 signalling activity.

The present invention also includes a method for identifying an agent which modulates PMN chemotaxis, comprising contacting a GPR43 polypeptide with a short chain fatty acid in the presence and absence of a candidate agent under conditions permitting binding of the short chain fatty acid to said GPR43 polypeptide; and measuring a signalling activity of the GPR43 polypeptide wherein an increase or decrease in signalling activity of the GPR43 in the presence of said candidate agent, relative to the signalling activity in the absence of the candidate agent, identifies said candidate agent as an agent which modulates PMN chemotaxis.

The present invention also provides a method for identifying an agent for the treatment of a PMN chemotaxis related disease comprising contacting a GPR43 polypeptide with a short chain fatty acid in the presence and absence of a candidate agent under conditions permitting binding of the short chain fatty acid to said GPR43 polypeptide; and measuring a signalling activity of the GPR43 polypeptide wherein an increase or decrease in signalling activity of the GPR43 in the presence of said candidate agent, relative to the signalling activity in the absence of the candidate agent, identifies said candidate agent as an agent for the treatment of a PMN chemotaxis-related disease.

The present invention provides a method for identifying an agent which modulates PMN chemotaxis, comprising contacting a GPR43 polypeptide with a short chain fatty acid in the presence and absence of a candidate agent under conditions permitting binding of the short chain fatty acid to the GPR43 polypeptide; and measuring binding of the GPR43 polypeptide to the short chain fatty acid, wherein a decrease in binding in the presence of the candidate agent, relative to binding in the absence of the candidate agent, identifies said candidate agent as an agent which modulates PMN chemotaxis.

The present invention still further provides a method for identifying an agent for the treatement of a PMN chemotaxis-related disease comprising contacting a GPR43 polypeptide with a short chain fatty acid in the presence and absence of a candidate agent under conditions permitting binding of the short chain fatty acid to the GPR43 polypeptide; and measuring binding of the GPR43 polypeptide to the short chain fatty acid, wherein a decrease in binding in the presence of the candidate agent, relative to binding in the absence of the candidate agent, identifies said candidate agent as an agent for the treatment of a PMN chemotaxis-related disease.

In one embodiment, the GPR43 receptor is present in the cell membrane of a PMN cell.

In one embodiment, the short chain fatty acid is detectably labeled.

In a further embodiment, the short chain fatty acid is detectably labeled with a moiety selected from the group consisting of a radioisotope, a fluorophore, a quencher of fluorescence, an enzyme, and an affinity tag.

As used herein, the term "polymorphonuclear cell" or "PMN" refers to a leukocyte of granulocytic lineage of between 10-14 µm in diameter. A "PMN" according to the invention has a nucleus with coarse, clumped, deeply staining chromatin with two or more lobes or segments (although immature PMN cells may have unlobated, band nuclei). A "PMN" according to the invention also has a granular cytoplasm containing small, weakly staining, or large strongly staining basophilic granules, or large (0.5-1 µm) eosinophilic granules. The morphology of a PMN cell according to the invention is well known to those of skill in the art.

As used herein, "PMN chemotaxis" refers to the to the directed movement of a PMN cell in response to, and either towards or away from a chemotactic factor. Chemotactic factors include, but are not limited to bacterial factors (N-formylated peptides such as fMLP, which are unique to the initiation of bacterial protein), plasma proteins (e.g., C5a, one of the activated products of either the classical or alternative pathways of complement activation, and leukotrines), and cells (e.g., TGF-beta and other cytokines, polypeptides released from lymphocytes, mast cells, and basophils, $G_c$-globulin, opsonins). PMN chemotaxis may be measured, according to the invention, by procedures originally developed by S. Boyden in 1962. (See, S. Boyden, The Chemotactic Effect of Mixtures of Antibody and Antigen on Polymorphonuclear Leucocytes, J. Exp. Med. 115: pp. 453-466, 1962). Briefly, the procedure involves placing a suspension of PMN cells and a chemical agent in two separate chambers, which chambers are separated by a polycarbonate filter. The PMN may, for example, be prepared from the peripheral blood of a mammal. After a predetermined period of time, the filter is removed and cells on the filter surface closest to the chamber containing the cell suspension are carefully removed. The remaining cells on the filter are then fixed and stained. Using a high power microscope, the filter is examined and the number of cells appearing on the underside of the filter (i.e., the side of the filter closest to the chamber containing the chemical agent) are counted manually. A positive chemotactic response is indicated by the cells having migrated or "crawled" through the filter to the side closest to the chamber containing the chemical agent. Because of the time required to do so, typically the entire filter is not examined. Rather, representative sample areas are examined and counted. According to the invention, "PMN chemotaxis" is said to have occurred where there are at least 10% more PMN cells on the filter surface aposed to the chamber containing the chemotactic factor when the chemotactic factor is present in the chamber, than when the chemotactic factor is not present.

As used herein, an "antagonist" is a ligand which competitively binds to a receptor at the same site as an agonist, but does not activate an intracellular response initiated by an active form of the receptor. An antagonist thereby inhibits the intracellular response induced by an agonist, for example propionate, by at least 10%, preferably 15-25%, more preferably 25-50% and most preferably, 50-100%, as compared to the intracellular response in the presence of an agonist and in the absence of an antagonist.

As used herein, an "agonist" refers to a ligand that activates an intracellular response when it binds to a receptor at concentrations equal to or lower than propionate concentrations which induce an intracellular response. An agonist according to the invention can increase the intracellular response mediated by a receptor by at least 2-fold, preferably 5-fold, more preferably 10-fold and most preferably 100-fold or more (i.e., 150-fold, 200-fold, 250-fold, 500-fold, 1000-fold, 10,000-fold etc . . . ), as compared to the intracellular response in the absence of agonist. An agonist according to the invention may decrease internalization of a cell surface receptor such that the cell surface expression of a receptor is increased by at least 2-fold, preferably 5-fold, more preferably 10-fold and most preferably, 100-fold or more (i.e., 150-fold, 200-fold, 250-fold, 500-fold, 1000-fold, 10,000-fold etc. . . . ), as compared to the number of cell surface receptors present on the surface of a cell in the absence of an agonist. In another embodiment of the invention, an agonist stablizes a cell surface receptor and increases the cell surface expression of a receptor by at least 2-fold, preferably 5-fold, more preferably 10-fold and most preferably, 100-fold or more (i.e., 200-fold, 250-fold, 500-fold, 1000-fold, 10,000-fold etc . . . ), as compared to the number of cell surface receptors present on the surface of a cell in the absence of agonist.

As used herein, an "inverse agonist" refers to a ligand which decreases a constitutive activity of a cell surface receptor when it binds to a receptor. An inverse agonist according to the invention can decrease the constitutive intracellular response mediated by a receptor by at least 2-fold, preferably 5-fold, more preferably 10-fold and most preferably 100-fold or more (i.e., 150-fold, 200-fold, 250-fold, 500-fold, 1000-fold, 10,000-fold etc. . . . ), as compared to the intracellular response in the absence of inverse agonist.

An "inhibitor" compound according to the invention is a molecule directed against the receptor or against the natural ligand for the receptor that decreases the binding of the ligand to the receptor by at least 10%, preferably 15-25%, more preferably 25-50% and most preferably, 50-100%, in the presence of acetate or propionate, as compared to the binding in the presence of acetate or propionate and in the absence of inhibitor. An "inhibitor" compound of the invention can decrease the intracellular response induced by an agonist, for example acetate or propionate, by at least 10%, preferably 15-25%, more preferably 25-50% and most preferably, 50-100%. An "inhibitor" also refers to a nucleotide sequence encoding an inhibitor compound of the invention. An inhibitor, useful according to the present invention, includes, but is not limited to an antibody which specifically binds to at least a portion of GPR43 which is required for signal transduction through GPR43 (such as the ligand binding site), or chemical compounds which are capable of blocking or reducing (e.g., by at least 10%) the signal transduction pathway which is coupled to the GPR43 receptor. Such inhibitors include, but are not limited to sub-lethal doses of pertussis toxin, N-ethylmaleimide (NEM; Sigma), dibutyryl cAMP (Boehringer Mannheim, Corp.), and H-89 (N-[2-((p-bromocinnamyl)amino)ethyl]-5-isoquinoline-sulfonamide-HCL; Calbiochem).

As used herein, "natural ligand" refers to a naturally occurring ligand, found in nature, which binds to a receptor in a manner that is at least equivalent to acetate or propionate (i.e., with an affinity for the receptor that is greater than the affinity of formate (acetate=propionate>formate)). A "natural ligand" does not refer to an engineered ligand that is not found in nature and that is engineered to bind to a receptor, where it did not formerly do so in a manner different, either in degree or kind, from that which it was engineered to do. Such an engineered ligand is no longer naturally-occurring but is "non-natural" and is derived from a naturally occurring molecule.

As used herein, a "modulator" refers to a compound that increases or decreases the cell surface expression of a receptor of the invention, increases or decreases the binding of a ligand to a receptor of the invention, or any compound that increases or decreases the intracellular response initiated by an active form of the receptor of the invention, either in the presence or absence or an agonist, and in the presence of a ligand for the receptor, for example acetate or propionate. A modulator includes an agonist, antagonist, inhibitor or inverse agonist, as defined herein. A modulator can be for example, a polypeptide, a peptide, an antibody or antigen-binding fragment thereof, a lipid, a carbohydrate, a nucleic acid, and a small organic molecule. Candidate modulators can be natural or synthetic compounds, including, for example, synthetic small molecules, compounds contained in extracts of animal, plant, bacterial or fungal cells, as well as conditioned medium from such cells.

As used herein, "increase" and "decrease" refer to a change in ligand binding to the GPR43 receptor and/or cell signalling through GPR43 of at least 10%. An "increase" or "decrease" in binding or signalling is preferably measured in response to contacting GPR43 with a ligand in the presence of a candidate modulator, wherein the change in binding or signalling is relative to the binding or signalling in the absence of the candidate modulator.

As used herein, the term "small molecule" refers to a compound having molecular mass of less than 3000 Daltons, preferably less than 2000 or 1500, still more preferably less than 1000, and most preferably less than 600 Daltons. A "small organic molecule" is a small molecule that comprises carbon.

As used herein, the terms "change", "difference", "decrease", or "increase" as applied to e.g., binding or signalling activity or amount of a substance refer to an at least 10% increase or decrease in binding, signalling activity, or for example, level of mRNA, polypeptide or ligand relative to a standard in a given assay.

As used herein, the term "dysregulation" refers to the signalling activity of GPR43 in a sample wherein:

a) a 10% or greater increase or decrease in the amount of one or more of GPR43 polypeptide, ligand or mRNA level is measured relative to a standard, as defined herein, in a given assay or;

b) at least a single base pair change in the GPR43 coding sequence is detected relative to SEQ ID NO: 1, and results in an alteration of GPR43 ligand binding or signalling activity as defined in paragraphs a), c) or d) or;

c) a 10% or greater increase or decrease in the amount of GPR43 ligand binding activity is measured relative to a standard, as defined herein, in a given assay or;

d) a 10% or greater increase or decrease in a second messenger, as defined herein, is measured relative to the standard, as defined herein, in a given assay.

As used herein, the term "conditions permitting the binding of SFCA to a GPR43 polypeptide" refers to conditions of, for example, temperature, salt concentration, pH and protein concentration under which SCFA, (e.g., acetate or propionate) binds GPR43. Exact binding conditions will vary depending upon the nature of the assay, for example, whether the assay uses viable cells or only a membrane fraction of cells. However, because GPR43 is a cell surface protein favored conditions will generally include physiological salt (90 mM) and pH (about 7.0 to 8.0). Temperatures for binding can vary from 15° C. to 37° C., but will preferably be between room temperature and about 30° C. The concentration of SCFA in a binding reaction will also vary, but will preferably be about 1 µM (e.g., in a reaction with radiolabelled tracer SCFA, e.g., propionate, where the concentration is generally below the $K_d$) to 10 mM (e.g., propionate as competitor).

As used herein, the term "sample" refers to the source of molecules being tested for the presence of an agent or modulator compound that modulates binding to or signalling activity of a GPR43 polypeptide. A sample can be an environmental sample, a natural extract of animal, plant yeast or bacterial cells or tissues, a clinical sample, a synthetic sample, or a conditioned medium from recombinant cells or a fermentation process. The term "tissue sample" refers to a tissue that is tested for the presence, abundance, quality or an activity of a GPR43 polypeptide, a nucleic acid encoding a GPR43 polypeptide, a GPR43 ligand or an agent or compound that modifies the ligand binding or activity of a GPR43 polypeptide.

As used herein, a "tissue" is an aggregate of cells that perform a particular function in an organism. The term "tissue" as used herein refers to cellular material from a particular physiological region. The cells in a particular tissue can comprise several different cell types. A non-limiting example of this would be brain tissue that further comprises neurons and glial cells, as well as capillary endothelial cells and blood cells, all contained in a given tissue section or sample. In addition to solid tissues, the term "tissue" is also intended to encompass non-solid tissues, such as blood.

As used herein, the term "membrane fraction" refers to a preparation of cellular lipid membranes comprising a GPR43 polypeptide. As the term is used herein, a "membrane fraction" is distinct from a cellular homogenate, in that at least a portion (i.e., at least 10%, and preferably more) of non-membrane-associated cellular constituents has been removed. The term "membrane associated" refers to those cellular constituents that are either integrated into a lipid membrane or are physically associated with a component that is integrated into a lipid membrane.

As used herein, the "second messenger assay" preferably comprises the measurement of guanine nucleotide binding or exchange, adenylate cyclase, intra-cellular cAMP, intra-cellular inositol phosphate, intra-cellular diacylglycerol concentration, arachidonic acid concentration, MAP kinase(s) or tyrosine kinase(s), protein kinase C activity, or reporter gene expression or an aequorin-based assay according to methods known in the art and defined herein.

As used herein, the term "second messenger" refers to a molecule, generated or caused to vary in concentration by the activation of a G-Protein Coupled Receptor, that participates in the transduction of a signal from that GPCR. Non-limiting examples of second messengers include cAMP, diacylglycerol, inositol triphosphate, arachidonic acid release, inositol triphosphates and intracellular calcium. The term "change in the level of a second messenger" refers to an increase or decrease of at least 10% in the detected level of a given second messenger relative to the amount detected in an assay performed in the absence of a candidate modulator.

As used herein, the term "aequorin-based assay" refers to an assay for GPCR activity that measures intracellular calcium flux induced by activated GPCRs, wherein intracellular calcium flux is measured by the luminescence of aequorin expressed in the cell.

As used herein, the term "binding" refers to the physical association of a ligand (e.g., an SCFA such as propionate, or an antibody) with a receptor (e.g., GPR43). As the term is used herein, binding is "specific" if it occurs with an $EC_{50}$ or a $K_d$ of 1 mM less, generally in the range of 1 mM to 10 nM For example, binding is specific if the $EC_{50}$ or $K_d$ is 1 mM, 500 µM, 100 µM, 10 µM, 9.5 µM, 9 µM, 8.5 µM, 8 µM, 7.5 µM, 7 µM, 6.5 µM, 6 µM, 5.5 µM, 5 µM, 4.5 µM, 4 µM, 3.5 µM, 3 µM, 2.5 µM, 2 µM, 1.5 µM, 1 µM, 750 nM, 500 nM, 250 nM As used herein, the term "$EC_{50}$," refers to that concentration of a compound at which a given activity, including binding of propionate or other ligand and a functional activity of a GPR43 polypeptide, is 50% of the maximum for that GPR43 activity measurable using the same assay in the absence of compound. Stated differently, the "$EC_{50}$" is the concentration of compound that gives 50% activation, when 100% activation is set at the amount of activity that does not increase with the addition of more agonist. It should be noted that the "$EC_{50}$" of an analog, of, for example, propionate, will vary according to the identity of the analogue used in the assay; for example, propionate analogues can have $EC_{50}$ values higher than, lower than or the same as propionate. Therefore, where a propionate analogue differs from propionate, one of skill in the art can determine the $EC_{50}$ for that analogue according to conventional methods. The $EC_{50}$ of a given SCFA is measured by performing an assay for the activity of a fixed amount of GPR43 polypeptide in the presence of doses of SCFA that increase at least until the GPR43 response is saturated or maximal, and then plotting the measured GPR43 activity versus the concentration of SCFA.

As used herein, the term "saturation" refers to the concentration of propionate or other ligand at which further increases in ligand concentration fail to increase the binding of ligand or GPR43-specific signalling activity.

As used herein, the term "$IC_{50}$" is the concentration of an antagonist or inverse agonist that reduces the maximal activation of a GPR43 receptor by 50%.

As used herein, the term "LD50" refers to the dose of a particular agent necessary to kill 50% of the subjects to which it is administered.

As used herein, the term "decrease in binding" refers to a decrease of at least 10% in the amount of ligand binding detected in a given assay with a known or suspected modulator of GPR43 relative to binding detected in an assay lacking that known or suspected modulator.

As used herein, the term "delivering," when used in reference to a drug or agent, means the addition of the drug or agent to an assay mixture, or to a cell in culture. The term also refers to the administration of the drug or agent to an animal. Such administration can be, for example, by injection (in a suitable carrier, e.g., sterile saline or water) or by inhalation, or by an oral, transdermal, rectal, vaginal, or other common route of drug administration.

As used herein, the term "standard" refers to a sample taken from an individual who is not affected by a disease or disorder characterized by dysregulation of GPR43 activity. The "standard" is used as a reference for the comparison of GPR43 mRNA or polypeptide levels and quality (i.e., mutant vs. wild type), as well as for the comparison of GPR43 activities. A "standard" also encompasses a reference sequence, e.g., SEQ ID NO: 1 or SEQ ID NO: 2, with which sequences of nucleic acids or their encoded polypeptides are compared.

As used herein, the term "amplifying," when applied to a nucleic acid sequence, refers to a process whereby one or more copies of a nucleic acid sequence is generated from a template nucleic acid. A preferred method of "amplifying" is PCR or RT/PCR.

As used herein, the term "G-Protein coupled receptor," or "GPCR" refers to a membrane-associated polypeptide with 7 alpha helical transmembrane domains. Functional GPCR's associate with a ligand or agonist and also associate with and activate G-proteins. GPR43 is a GPCR.

As used herein, the term "antibody" is the conventional immunoglobulin molecule, as well as fragments thereof which are also specifically reactive with one of the subject polypeptides. Antibodies can be fragmented using conventional techniques and the fragments screened for utility in the same manner as described herein below for whole antibodies. For example, $F(ab)_2$ fragments can be generated by treating antibody with pepsin. The resulting $F(ab)_2$ fragment can be treated to reduce disulfide bridges to produce Fab fragments. The antibody of the present invention is further intended to include bispecific, single-chain, and chimeric and humanised molecules having affinity for a polypeptide conferred by at least one CDR region of the antibody. In preferred embodiments, the antibody further comprises a label attached thereto and able to be detected, (e.g., the label can be a radioisotope, fluorescent compound, chemiluminescent compound, enzyme, or enzyme co-factor). The antibodies, monoclonal or polyclonal and its hypervariable portion thereof (FAB, FAB", etc.) as well as the hybridoma cell producing the antibodies are a further aspect of the present invention which find a specific industrial application in the field of diagnostics and monitoring of specific diseases, preferably the ones hereafter described.

Inhibitors according to the invention include but are not limited to labeled monoclonal or polyclonal antibodies or hypervariable portions of the antibodies.

As used herein, the term "transgenic animal" refers to any animal, preferably a non-human mammal, bird, fish or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical crossbreeding, or in vitro fertilization, but rather is directed to the introduction of a recombinant DNA molecule. This molecule may be integrated within a chromosome, or it may be extra-chromosomally replicating DNA. In the typical transgenic animals described herein, the transgene causes cells to express a recombinant form of one of the subject polypeptide, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

BRIEF DESCRIPTION OF FIGURES

FIG. 1 represents nucleotide (SEQ ID NO. 1) and deduced amino acid (SEQ ID NO. 2) sequence of the human GPR43 receptor.

FIG. 2 is a dendrogram showing the structural relatedness of the GPR43 receptor with related receptors. Alignment of the amino acid sequence of GPR43 with PAR1 and other PAR related sequences were performed using ClustalX algorithm. Then, the dendrogram was constucted using TreeView algorithm. Proteinase activated receptor (PAR)-1, -2, -3, -4; platelet-activating factor receptor (PAF); G-protein coupled receptor 43 (GPR43); G-protein coupled receptor 42 (GRP42). The latter one is always a orphan receptor FIG. 3 shows tissue distribution of the human GPR43 receptor.

FIG. 12 illustrates the names and formulae of SCFAs and related compounds tested, and their respective effects on human GPR43 activity.

FIG. 13 shows the tissue distribution of human GPR43 transcripts using semi-quantitative RT-PCR (TaqMan) methodology over a range of 12 selected human tissues. Data are presented as the ratio Z of the mean mRNA copies for each tissue from 2.5 ng of polyA+RNA or from 25 ng of total RNA. Panel A shows the mean (+/−S.D.) mRNA copies of glyceraldehyde-3-phosphate dehydrogenase (GAPDH) gene's mRNA detected/2.5 ng of polyA+RNA or from 25 ng of total RNA (Y axis). Panel B shows the mean (+/−S.D.) mRNA copies of GPR43. Y axis=copies of gene's mRNA detected/2.5 ng of polyA+RNA or from 25 ng of total RNA. Panel C shows the ratio (Z) of the GPCR/GAPDH means mRNA copies for each tissue (Y axis).

FIG. 17 shows neutrophil migration in response to increasing concentrations of SCFA (acetate and propionate) reported as a migration index. The chemotaxis data represents the mean and SEM of 5 independent experiments.

DETAILED DESCRIPTION OF THE INVENTION

Figure 4:
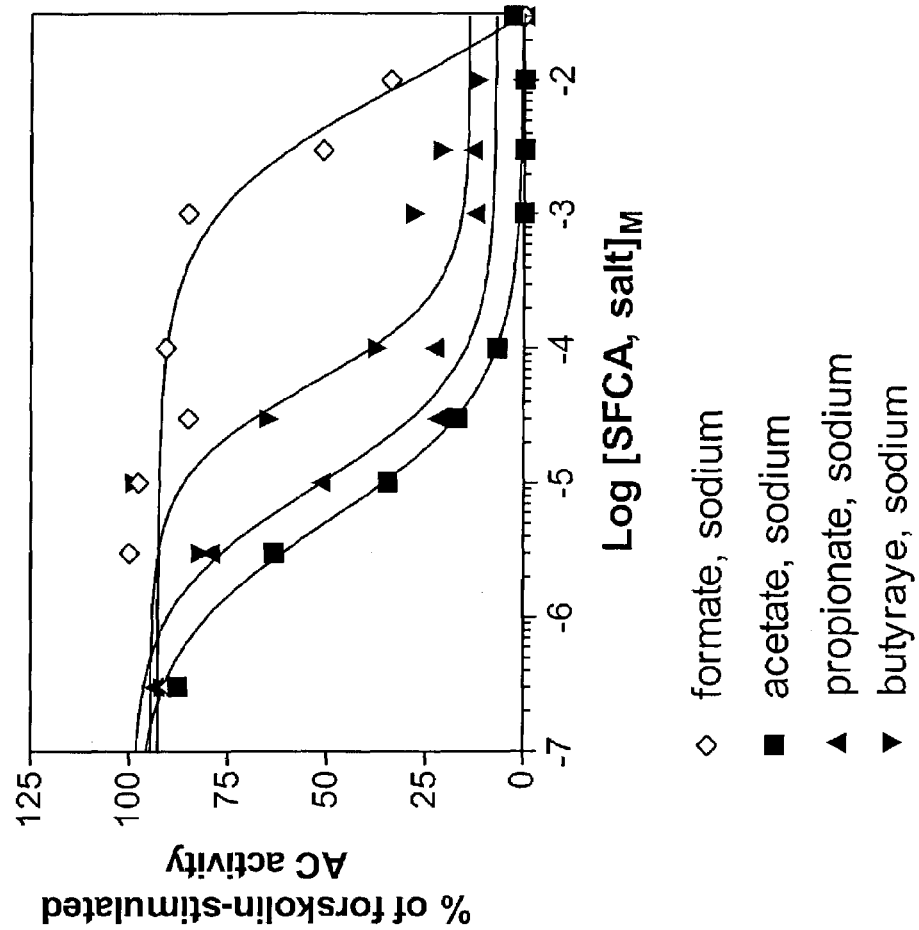
FIG. 4 illustrates the inhibitory activity of SCFA on forskolin-stimulated adenylate cyclase activity in CHO-K1 cells stably expressing the human GPR43.

The invention is based on the discovery that short chain fatty acids are natural ligands for the orphan G protein coupled receptor GPR43 and on methods of using the binding of this ligand to the receptor in drug screening methods. The known ligand and its interaction with the receptor GPR43 also provides for the diagnosis of conditions involving dysregulated receptor activity. The invention also relates to a kit comprising GPR43 and homologous sequences, its corresponding polynucleotide and/or recombinant cells expressing the polynucleotide, to identify agonist, antagonist and inverse agonist compounds of the receptor polypeptide and/or its corresponding polynucleotide. Such kits are useful for the diagnosis, prevention and/or a treatment of diseases and disorders related to GPR43 activity.

The invention also relates to novel agonist, antagonist and inverse agonist compounds of the receptor polypeptide and its corresponding polynucleotide, identified according to the method of the invention.

All references referred to below and above are incorporated herein by reference in their entirety.

Sequences

The invention relates to the nucleotide (SEQ ID NO: 1) and amino acid (SEQ ID NO: 2) sequences encoding GPR43 (presented in FIG. 1). The invention also relates to sequences that are homologous to the nucleotide and amino acid sequences encoding GPR43.

GPR43 Tissue Distribution

GPR43 is mainly expressed on neutrophils, and to a lower extent on monocytes, macrophages, lymphocytes T as well as in spleen and bone marrow. Its mRNA is also weakly detected in eosinophils and mast cells. Its expression is enhanced by cytokine and LPS stimulation, suggesting a possible role in leukocyte differentiation and activation (Senga et al., 2002).

Calculation of Sequence Homology

Sequence identity with respect to any of the sequences presented herein can be determined by a simple "eyeball" comparison (i.e. a strict comparison) of any one or more of the sequences with another sequence to see if that other sequence has, for example, at least 80% sequence identity to the sequence(s).

Relative sequence identity can also be determined by commercially available computer programs that can calculate % identity between two or more sequences using any suitable algorithm for determining identity, using for example default parameters. A typical example of such a computer program is CLUSTAL. Other computer program methods to determine identity and similarity between two sequences include but are not limited to the GCG program package (Devereux et al 1984 Nucleic Acids Research 12: 387) and FASTA (Atschul et al 1990 J Molec Biol 403-410).

% homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software that can perform sequence comparisons include, but are not limited to, the BLAST package (Ausubel et al., 1995, *Short Protocols in Molecular Biology*, 3rd Edition, John Wiley & Sons), FASTA (Atschul et al., 1990, J. Mol. Biol., 403-410) and the GENEWORKS suite of comparison tools. Both BLAST and FASTA are available for offline and online searching (Ausubel et al., 1999 supra, pages 7-58 to 7-60).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied. It is preferred to use the public default values for the GCG package, or in the case of other software, the default matrix, such as BLOSUM62.

Advantageously, the BLAST algorithm is employed, with parameters set to default values. The BLAST algorithm is described in detail at http://www.ncbi.nih.gov/BLAST/blast_help.html, which is incorporated herein by reference. The search parameters are defined as follows, and can be advantageously set to the defined default parameters.

Advantageously, "substantial identity" when assessed by BLAST equates to sequences which match with an EXPECT value of at least about 7, preferably at least about 9 and most preferably 10 or more. The default threshold for EXPECT in BLAST searching is usually 10.

BLAST (Basic Local Alignment Search Tool) is the heuristic search algorithm employed by the programs blastp, blastn, blastx, tblastn, and tblastx; these programs ascribe significance to their findings using the statistical methods of Karlin and Altschul (Karlin and Altschul 1990, *Proc. Natl. Acad. Sci. USA* 87:2264-68; Karlin and Altschul, 1993, *Proc. Natl. Acad. Sci. USA* 90:5873-7; see http://www.ncbi.nlm.nih.gov/BLAST/blast_help.html) with a few enhancements. The BLAST programs are tailored for sequence similarity searching, for example to identify homologues to a query sequence. For a discussion of basic issues in similarity searching of sequence databases, see Altschul et al (1994) Nature Genetics 6:119-129.

The five BLAST programs available at http://www.ncbi.nlm.nih.gov perform the following tasks: blastp—compares an amino acid query sequence against a protein sequence database; blastn—compares a nucleotide query sequence against a nucleotide sequence database; blastx—compares the six-frame conceptual translation products of a nucleotide query sequence (both strands) against a protein sequence database; tblastn—compares a protein query sequence against a nucleotide sequence database dynamically translated in all six reading frames (both strands); tblastx—compares the six-frame translations of a nucleotide query sequence against the six-frame translations of a nucleotide sequence database.

BLAST uses the following search parameters:

HISTOGRAM—Display a histogram of scores for each search; default is yes. (See parameter H in the BLAST Manual).

DESCRIPTIONS—Restricts the number of short descriptions of matching sequences reported to the number specified; default limit is 100 descriptions. (See parameter V in the manual page).

EXPECT—The statistical significance threshold for reporting matches against database sequences; the default value is 10, such that 10 matches are expected to be found merely by chance, according to the stochastic model of Karlin and Altschul (1990). If the statistical significance ascribed to a match is greater than the EXPECT threshold, the match will not be reported. Lower EXPECT thresholds are more stringent, leading to fewer chance matches being reported. Fractional values are acceptable. (See parameter E in the BLAST Manual).

CUTOFF—Cutoff score for reporting high-scoring segment pairs. The default value is calculated from the EXPECT value (see above). HSPs are reported for a database sequence only if the statistical significance ascribed to them is at least as high as would be ascribed to a lone HSP having a score equal to the CUTOFF value. Higher CUTOFF values are more stringent, leading to fewer chance matches being reported. (See parameter S in the BLAST Manual). Typically, significance thresholds can be more intuitively managed using EXPECT.

ALIGNMENTS—Restricts database sequences to the number specified for which high-scoring segment pairs (HSPs) are reported; the default limit is 50. If more database sequences than this happen to satisfy the statistical significance threshold for reporting (see EXPECT and CUTOFF below), only the matches ascribed the greatest statistical significance are reported. (See parameter B in the BLAST Manual).

MATRIX—Specify an alternate scoring matrix for BLASTP, BLASTX, TBLASTN and TBLASTX. The default matrix is BLOSUM62 (Henikoff & Henikoff, 1992). The valid alternative choices include: PAM40, PAM120, PAM250 and IDENTITY. No alternate scoring matrices are available for BLASTN; specifying the MATRIX directive in BLASTN requests returns an error response.

STRAND—Restrict a TBLASTN search to just the top or bottom strand of the database sequences; or restrict a BLASTN, BLASTX or TBLASTX search to just reading frames on the top or bottom strand of the query sequence.

FILTER—Mask off segments of the query sequence that have low compositional complexity, as determined by the SEG program of Wootton & Federhen (1993) Computers and Chemistry 17:149-163, or segments consisting of short-periodicity internal repeats, as determined by the XNU program of Claverie & States (1993) Computers and Chemistry 17:191-201, or, for BLASTN, by the DUST program of Tatusov and Lipman (see http://www.ncbi.nlm.nih.gov). Filtering can eliminate statistically significant but biologically uninteresting reports from the blast output (e.g., hits against common acidic-, basic- or proline-rich regions), leaving the more biologically interesting regions of the query sequence available for specific matching against database sequences.

Low complexity sequence found by a filter program is substituted using the letter "N" in nucleotide sequence (e.g., "NNNNNNNNNNNNN") and the letter "X" in protein sequences (e.g., "XXXXXXXXX").

Filtering is only applied to the query sequence (or its translation products), not to database sequences. Default filtering is DUST for BLASTN, SEG for other programs.

It is not unusual for nothing at all to be masked by SEG, XNU, or both, when applied to sequences in SWISS-PROT, so filtering should not be expected to always yield an effect. Furthermore, in some cases, sequences are masked in their entirety, indicating that the statistical significance of any matches reported against the unfiltered query sequence should be suspect.

NCBI-gi—Causes NCBI gi identifiers to be shown in the output, in addition to the accession and/or locus name.

Most preferably, sequence comparisons are conducted using the simple BLAST search algorithm provided at http://www.ncbi.nlm.nih.gov/BLAST. In some embodiments of the present invention, no gap penalties are used when determining sequence identity.

Cells

A cell that is useful according to the invention is preferably selected from the group consisting of bacterial cells, yeast cells, insect cells or mammalian cells.

A cell that is useful according to the invention can be any cell into which a nucleic acid sequence encoding a receptor according to the invention can be introduced such that the receptor is expressed at natural levels or above natural levels, as defined herein. Preferably a receptor of the invention that is expressed in a cell exhibits normal or near normal pharmacology, as defined herein. Most preferably a receptor of the invention that is expressed in a cell comprises the nucleotide or amino acid sequence presented in FIG. 1 or a nucleotide or amino acid sequence that is at least 70% identical to the amino acid sequence presented in FIG. 1. Preferably, a receptor of the invention that is expressed in a cell will bind propionate with an affinity that is at least 100-fold, preferably 500-fold and most preferably 1000-fold greater than the affinity for IDP and UDP.

According to a preferred embodiment of the present invention, a cell is selected from the group consisting of COS7-cells, a CHO cell, a LM (TK−) cell, a NIH-3T3 cell, HEK-293 cell, K-562 cell or a 1321N1 astrocytoma cell but also other transfectable cell lines.

Assays

I. Assays for the Identification of Agents that Modulate the Activity of GPR43

Agents that modulate the activity of GPR43 can be identified in a number of ways that take advantage of the newly discovered interaction of the receptor with SCFAs, such as acetete and propionate. For example, the ability to reconstitute GPR43/propionate binding either in vitro, on cultured cells or in vivo provides a target for the identification of agents that disrupt that binding. Assays based on disruption of binding can identify agents, such as small organic molecules, from libraries or collections of such molecules. Alternatively, such assays can identify agents in samples or extracts from natural sources, e.g., plant, fungal or bacterial extracts or even in human tissue samples (e.g., tumor tissue). In one aspect, the extracts can be made from cells expressing a library of variant nucleic acids, peptides or polypeptides. Modulators of GPR43/SCFA binding can then be screened using a binding assay or a functional assay that measures downstream signalling through the receptor.

Another approach that uses the GPR43/SCFA interaction more directly to identify agents that modulate GPR43 function measures changes in GPR43 downstream signalling induced by candidate agents or candidate modulators. These functional assays can be performed in isolated cell membrane fractions or on cells expressing the receptor on their surfaces.

The discovery that SCFAs, such as acetate and propionate are ligands of the GPR43 receptor permits screening assays to identify agonists, antagonists and inverse agonists of receptor activity. The screening assays have two general approaches, detailed below. For the purposes of this section propionate is used as an exemplary SCFA. It should be understood, however, that any SCFA as defined herein can be used in the assays described.

1) Ligand binding assays, in which cells expressing GPR43, membrane extracts from such cells, or immobilized lipid membranes comprising GPR43 are exposed to labelled and candidate compound. Following incubation, the reaction mixture is measured for specific binding of the labelled to the GPR43 receptor. Compounds that interfere with binding or displace labelled can be agonists, antagonists or inverse agonists of GPR43 activity. Subsequent functional analysis can then be performed on positive compounds to determine in which of these categories they belong.

2) Functional assays, in which a signalling activity of GPR43 is measured.

a) For agonist screening, cells expressing GPR43 or membranes prepared from them are incubated with a candidate compound, and a signalling activity of GPR43 is measured. The activity induced by compounds that modulate receptor activity is compared to that induced by the natural ligands, acetate or propionate. An agonist or partial agonist will have a maximal biological activity corresponding to at least 10% of the maximal activity of propionate when the agonist or partial agonist is present at 1 mM or less, and preferably will have a potency which is at least as potent as acetate or propionate.

b) For antagonist or inverse agonist screening, cells expressing GPR43 or membranes isolated from them are assayed for signalling activity in the presence of propionate with or without a candidate compound. Antagonists will reduce the level of propionate-stimulated receptor activity by at least 10%, relative to reactions lacking the antagonist in the presence of propionate. Inverse agonists will reduce the constitutive activity of the receptor by at least 10%, relative to reactions lacking the inverse agonist.

c) For inverse agonist screening, cells expressing constitutive GPR43 activity or membranes isolated from them are used in a functional assay that measures an activity of the receptor in the presence of a candidate compound. Inverse agonists are those compounds that reduce the constitutive activity of the receptor by at least 10%. Overexpression of GPR43 may lead to constitutive activation. GPR43 can be overexpressed by placing it under the control of a strong constitutive promoter, e.g., the CMV early promoter. Alternatively, certain mutations of conserved GPCR amino acids or amino acid domains tend to lead to constitutive activity. See for example: Kjelsberg et al., 1992, J. Biol. Chem. 267:1430; McWhinney et al., 2000. J. Biol. Chem. 275: 2087; Ren et al., 1993, J. Biol. Chem. 268:16483; Samama et al., 1993, J. Biol. Chem 268:4625; Parma et al., 1993, Nature 365:649; Parma et al., 1998, J. Pharmacol. Exp. Ther. 286:85; and Parent et al., 1996, J. Biol. Chem. 271:7949.

Ligand Binding and Displacement Assays:

As noted in (1) above, one can use GPR43 polypeptides expressed on a cell, or isolated membranes containing receptor polypeptides, along with propionate in order to screen for compounds that inhibit the binding of propionate to GPR43. For the purposes of this section, propionate is used as an exemplary SCFA. It should be understood however that any SCFA as defined herein can be used in the assays described.

For displacement experiments, cells expressing a GPR43 polypeptide (generally 25,000 cells per assay or 1 to 100 μg of membrane extracts) are incubated in binding buffer with labelled propionate in the presence or absence of increasing concentrations of a candidate modulator. To validate and calibrate the assay, control competition reactions using increasing concentrations of unlabeled propionate can be performed. After incubation, cells are washed extensively, and bound, labelled propionate is measured as appropriate for the given label (e.g., scintillation counting, fluorescence, etc.). A decrease of at least 10% in the amount of labelled propionate bound in the presence of candidate modulator indicates displacement of binding by the candidate modulator. Candidate modulators are considered to bind specifically in this or other assays described herein if they displace 50% of labelled propionate (sub-saturating propionate dose) at a concentration of 1 mM or less.

Alternatively, binding or displacement of binding can be monitored by surface plasmon resonance (SPR). Surface plasmon resonance assays can be used as a quantitative method to measure binding between two molecules by the change in mass near an immobilized sensor caused by the binding or loss of binding of propionate from the aqueous phase to a GPR43 polypeptide immobilized in a membrane on the sensor. This change in mass is measured as resonance units versus time after injection or removal of the propionate or candidate modulator and is measured using a Biacore Biosensor (Biacore AB). GPR43 can be immobilized on a sensor chip (for example, research grade CM5 chip; Biacore AB) in a thin film lipid membrane according to methods described by Salamon et al. (Salamon et al., 1996, Biophys J. 71: 283-294; Salamon et al., 2001, Biophys. J. 80: 1557-1567; Salamon et al., 1999, Trends Biochem. Sci. 24: 213-219, each of which is incorporated herein by reference.). Sarrio et al. demonstrated that SPR can be used to detect ligand binding to the GPCR A(1) adenosine receptor immobilized in a lipid layer on the chip (Sarrio et al., 2000, Mol. Cell. Biol. 20: 5164-5174, incorporated herein by reference). Conditions for propionate binding to GPR43 in an SPR assay can be fine-tuned by one of skill in the art using the conditions reported by Sarrio et al. as a starting point.

SPR can assay for modulators of binding in at least two ways. First, propionate can be pre-bound to immobilized GPR43 polypeptide, followed by injection of candidate modulator at a concentration ranging from 0.1 nM to 1 µM. Displacement of the bound propionate can be quantitated, permitting detection of modulator binding. Alternatively, the membrane-bound GPR43 polypeptide can be pre-incubated with candidate modulator and challenged with propionate. A difference in propionate binding to the GPR43 exposed to modulator relative to that on a chip not pre-exposed to modulator will demonstrate binding or displacement of propionate in the presence of modulator. In either assay, a decrease of 10% or more in the amount of propionate bound is in the presence of candidate modulator, relative to the amount of a propionate bound in the absence of candidate modulator indicates that the candidate modulator inhibits the interaction of GPR43 and propionate.

Another method of detecting inhibition of binding of propionate to GPR43 uses fluorescence resonance energy transfer (FRET). FRET is a quantum mechanical phenomenon that occurs between a fluorescence donor (D) and a fluorescence acceptor (A) in close proximity to each other (usually <100 A of separation) if the emission spectrum of D overlaps with the excitation spectrum of A. The molecules to be tested, e.g. propionate and a GPR43 polypeptide, are labelled with a complementary pair of donor and acceptor fluorophores. While bound closely together by the GPR43: propionate interaction, the fluorescence emitted upon excitation of the donor fluorophore will have a different wavelength than that emitted in response to that excitation wavelength when the propionate and GPR43 polypeptide are not bound, providing for quantitation of bound versus unbound molecules by measurement of emission intensity at each wavelength.

Donor fluorophores with which to label the GPR43 polypeptide are well known in the art. Of particular interest are variants of the *A. victoria* GFP known as Cyan FP (CFP, Donor (D)) and Yellow FP (YFP, Acceptor(A)). As an example, the YFP variant can be made as a fusion protein with GPR43. Vectors for the expression of GFP variants as fusions (Clontech) as well as flurophore-labeled propionate compounds (Molecular Probes) are known in the art. The addition of a candidate modulator to the mixture of labelled propionate and YFP-GPR43 protein will result in an inhibition of energy transfer evidenced by, for example, a decrease in YFP fluorescence relative to a sample without the candidate modulator. In an assay using FRET for the detection of GPR43: propionate interaction, a 10% or greater decrease in the intensity of fluorescent emission at the acceptor wavelength in samples containing a candidate modulator, relative to samples without the candidate modulator, indicates that the candidate modulator inhibits the GPR43: propionate interaction.

A variation on FRET uses fluorescence quenching to monitor molecular interactions. One molecule in the interacting pair can be labelled with a fluorophore, and the other with a molecule that quenches the fluorescence of the fluorophore when brought into close apposition with it. A change in fluorescence upon excitation is indicative of a change in the association of the molecules tagged with the fluorophore:quencher pair. Generally, an increase in fluorescence of the labelled GPR43 polypeptide is indicative that the propionate molecule bearing the quencher has been displaced. For quenching assays, a 10% or greater increase in the intensity of fluorescent emission in samples containing a candidate modulator, relative to samples without the candidate modulator, indicates that the candidate modulator inhibits GPR43: propionate interaction.

In addition to the surface plasmon resonance and FRET methods, fluorescence polarization measurement is useful to quantitate binding. The fluorescence polarization value for a fluorescently-tagged molecule depends on the rotational correlation time)or tumbling rate. Complexes, such as those formed by GPR43 associating with a fluorescently labelled propionate, have higher polarization values than uncomplexed, labelled propionate. The inclusion of a candidate inhibitor of the GPR43: propionate interaction results in a decrease in fluorescence polarization, relative to a mixture without the candidate inhibitor, if the candidate inhibitor disrupts or inhibits the interaction of GPR43 with propionate. Fluorescence polarization is well suited for the identification of small molecules that disrupt the formation of receptor:ligand complexes. A decrease of 10% or more in fluorescence polarization in samples containing a candidate modulator, relative to fluorescence polarization in a sample lacking the candidate modulator, indicates that the candidate modulator inhibits GPR43: propionate interaction.

Another alternative for monitoring GPR43: propionate interactions uses a biosensor assay. ICS biosensors have been described in the art (Australian Membrane Biotechnology Research Institute; www.ambri.com.au/; Cornell B, Braach-Maksvytis V, King L, Osman P, Raguse B, Wieczorek L, and Pace R. "A biosensor that uses ion-channel switches" Nature1997, 387, 580). In this technology, the association of GPR43 and its ligand is coupled to the closing of gramacidin-facilitated ion channels in suspended membrane bilayers and thus to a measurable change in the admittance (similar to impedance) of the biosensor. This approach is linear over six orders of magnitude of admittance change and is ideally suited for large scale, high throughput screening of small molecule combinatorial libraries. A 10% or greater change (increase or decrease) in admittance in a sample containing a candidate modulator, relative to the admittance of a sample lacking the candidate modulator, indicates that the candidate modulator inhibits the interaction of GPR43 and propionate. It is important to note that in assays testing the interaction of GPR43 with propionate, it is possible that a modulator of the interaction need not necessarily interact directly with the domain(s) of the proteins that physically interact with propionate. It is also possible that a modulator will interact at a location removed from the site of interaction and cause, for example, a conformational change in the GPR43 polypeptide. Modulators (inhibitors or agonists) that act in this manner are nonetheless of interest as agents to modulate the activity of GPR43.

It should be understood that any of the binding assays described herein can be performed with a non-propionate ligand (for example, agonist, antagonist, etc.) of GPR43, e.g., a small molecule identified as described herein or propionate analogues including but not limited to any of the propionate analogues, a natural or synthetic peptide, a polypeptide, an antibody or antigen-binding fragment thereof, a lipid, a carbohydrate, and a small organic molecule.

Any of the binding assays described can be used to determine the presence of an agent in a sample, e.g., a tissue sample, that binds to the GPR43 receptor molecule, or that affects the binding of propionate to the receptor. To do so, GPR43 polypeptide is reacted with propionate or another ligand in the presence or absence of the sample, and propionate or ligand binding is measured as appropriate for the binding assay being used. A decrease of 10% or more in the binding of propionate or other ligand indicates that the sample contains an agent that modulates propionate or ligand binding to the receptor polypeptide.

Functional Assays of Receptor Activity i. GTPase/GTP Binding Assays:

For GPCRs such as GPR43, a measure of receptor activity is the binding of GTP by cell membranes containing receptors. In the method described by Traynor and Nahorski, 1995, Mol. Pharmacol. 47: 848-854, incorporated herein by reference, one essentially measures G-protein coupling to membranes by detecting the binding of labelled GTP. For GTP binding assays, membranes isolated from cells expressing the receptor are incubated in a buffer containing 20 mM HEPES, pH 7.4, 100 mM NaCl, and 10 mM MgCl2, 80 pM $^{35}$S-GTPγS and 3 μM GDP. The assay mixture is incubated for 60 minutes at 30° C., after which unbound labelled GTP is removed by filtration onto GF/B filters. Bound, labelled GTP is measured by liquid scintillation counting. In order to assay for modulation of propionate-induced GPR43 activity, membranes prepared from cells expressing a GPR43 polypeptide are mixed with propionate, and the GTP binding assay is performed in the presence and absence of a candidate modulator of GPR43 activity. An increase of 10% or more in labelled GTP binding as measured by scintillation counting in an assay of this kind containing a candidate modulator, relative to an assay without the modulator, indicates that the candidate modulator inhibits GPR43 activity. A similar GTP-binding assay can be performed without propionate to identify compounds that act as agonists. In this case, propionate-stimulated GTP binding is used as a standard. A compound is considered an agonist if it induces at least 50% of the level of GTP binding induced by propionate when the compound is present at 1 μM or less, and preferably will induce a level the same as or higher than that induced by propionate. GTPase activity is measured by incubating the membranes containing a GPR43 polypeptide with $\gamma^{32}$P-GTP. Active GTPase will release the label as inorganic phosphate, which is detected by separation of free inorganic phosphate in a 5% suspension of activated charcoal in 20 mM $H_3PO_4$, followed by scintillation counting. Controls include assays using membranes isolated from cells not expressing GPR43 (mock-transfected), in order to exclude possible non-specific effects of the candidate compound.

In order to assay for the effect of a candidate modulator on GPR43-regulated GTPase activity, membrane samples are incubated with propionate, with and without the modulator, followed by the GTPase assay. A change (increase or decrease) of 10% or more in the level of GTP binding or GTPase activity relative to samples without modulator is indicative of GPR43 modulation by a candidate modulator.

ii. Downstream Pathway Activation Assays:

a. Calcium Flux—The Aequorin-Based Assay.

The aequorin assay takes advantage of the responsiveness of mitochondrial apoaequorin to intracellular calcium release induced by the activation of GPCRs (Stables et al., 1997, Anal. Biochem. 252:115-126; Detheux et al., 2000, J. Exp. Med., 192 1501-1508; both of which are incorporated herein by reference). Briefly, GPR43-expressing clones are transfected to coexpress mitochondrial apoaequorin and Gα16. Cells are incubated with 5 μM Coelenterazine H (Molecular Probes) for 4 hours at room temperature, washed in DMEM-F12 culture medium and resuspended at a concentration of $0.5 \times 10^6$ cells/ml. Cells are then mixed with test agonist molecules and light emission by the aequorin is recorded with a luminometer for 30 sec. Results are expressed as Relative Light Units (RLU). Controls include assays using membranes isolated from cells not expressing GPR43 (mock transfected), in order to exclude possible non-specific effects of the candidate compound.

Aequorin activity or intracellular calcium levels are "changed" if light intensity increases or decreases by 10% or more in a sample of cells, expressing a GPR43 polypeptide and treated with a candidate modulator, relative to a sample of cells expressing the GPR43 polypeptide but not treated with the candidate modulator or relative to a sample of cells not expressing the GPR43 polypeptide (mock-transfected cells) but treated with the candidate modulator.

When performed in the absence of propionate, the assay can be used to identify an agonist of GPR43 activity. When the assay is performed in the presence of propionate, it can be used to assay for an antagonist.

b. Adenylate Cyclase Assay:

Assays for adenylate cyclase activity are described by Kenimer & Nirenberg, 1981, Mol. Pharmacol. 20: 585-591, incorporated herein by reference. That assay is a modification of the assay taught by Solomon et al., 1974, Anal. Biochem. 58: 541-548, also incorporated herein by reference. Briefly, 100 μl reactions contain 50 mM Tris-Hcl (pH 7.5), 5 mM $MgCl_2$, 20 mM creatine phosphate (disodium salt), 10 units (71 μg of protein) of creatine phosphokinase, 1 mM α-$^{32}$P-ATP (tetrasodium salt, 2 μCi), 0.5 mM cyclic AMP, G-$^3$H-labeled cyclic AMP (approximately 10,000 cpm), 0.5 mM Ro20-1724, 0.25% ethanol, and 50-200 μg of protein homogenate to be tested (i.e., homogenate from cells expressing or not expressing a GPR43 polypeptide, treated or not treated with propionate with or without a candidate modulator). Reaction mixtures are generally incubated at 37° C. for 60 minutes. Following incubation, reaction mixtures are deproteinized by the addition of 0.9 ml of cold 6% trichloroacetic acid. Tubes are centrifuged at 1800×g for 20 minutes and each supernatant solution is added to a Dowex AG50W-X4 column. The cAMP fraction from the column is eluted with 4 ml of 0.1 mM imidazole-HCl (pH 7.5) into a counting vial. Assays should be performed in triplicate. Control reactions should also be performed using protein homogenate from cells that do not express a GPR43 polypeptide.

According to the invention, adenylate cyclase activity is "changed" if it increases or decreases by 10% or more in a sample taken from cells treated with a candidate modulator of GPR43 activity, relative to a similar sample of cells not treated with the candidate modulator or relative to a sample of cells not expressing the GPR43 polypeptide (mock-transfected cells) but treated with the candidate modulator.

c. cAMP Assay:

Intracellular or extracellular cAMP is measured using a cAMP radioimmunoassay (RIA) or cAMP binding protein according to methods widely known in the art. For example, Horton & Baxendale, 1995, Methods Mol. Biol. 41: 91-105, which is incorporated herein by reference, describes an RIA for cAMP.

A number of kits for the measurement of cAMP are commercially available, such as the High Efficiency Fluorescence Polarization-based homogeneous assay marketed by LJL Biosystems and NEN Life Science Products. Control reactions should be performed using extracts of mock-transfected cells to exclude possible non-specific effects of some candidate modulators.

The level of cAMP is "changed" if the level of cAMP detected in cells, expressing a GPR43 polypeptide and treated with a candidate modulator of GPR43 activity (or in extracts of such cells), using the RIA-based assay of Horton & Baxendale, 1995, supra, increases or decreases by at least 10% relative to the cAMP level in similar cells not treated with the candidate modulator.

d. Phospholipid Breakdown, DAG Production and Inositol Triphosphate Levels:

Receptors that activate the breakdown of phospholipids can be monitored for changes due to the activity of known or suspected modulators of GPR43 by monitoring phospholipid breakdown, and the resulting production of second messengers DAG and/or inositol triphosphate ($IP_3$). Methods of detecting each of these are described in *Phospholipid Signalling Protocols*, edited by Ian M. Bird. Totowa, N.J., Humana Press, 1998, which is incorporated herein by reference. See also Rudolph et al., 1999, J. Biol. Chem. 274: 11824-11831, incorporated herein by reference, which also describes an assay for phosphatidylinositol breakdown. Assays should be performed using cells or extracts of cells expressing GPR43, treated or not treated with propionate with or without a candidate modulator. Control reactions should be performed using mock-transfected cells, or extracts from them in order to exclude possible non-specific effects of some candidate modulators.

According to the invention, phosphatidylinositol breakdown, and diacylglycerol and/or inositol triphosphate levels are "changed" if they increase or decrease by at least 10% in a sample from cells expressing a GPR43 polypeptide and treated with a candidate modulator, relative to the level observed in a sample from cells expressing a GPR43 polypeptide that is not treated with the candidate modulator.

e. PKC Activation Assays:

Growth factor receptor tyrosine kinases can signal via a pathway involving activation of Protein Kinase C (PKC), which is a family of phospholipid- and calcium-activated protein kinases. PKC activation ultimately results in the transcription of an array of proto-oncogene transcription factor-encoding genes, including c-fos, c-myc and c-jun, proteases, protease inhibitors, including collagenase type I and plasminogen activator inhibitor, and adhesion molecules, including intracellular adhesion molecule I (ICAM I). Assays designed to detect increases in gene products induced by PKC can be used to monitor PKC activation and thereby receptor activity. In addition, the activity of receptors that signal via PKC can be monitored through the use of reporter gene constructs driven by the control sequences of genes activated by PKC activation. This type of reporter gene-based assay is discussed in more detail below.

For a more direct measure of PKC activity, the method of Kikkawa et al., 1982, J. Biol. Chem. 257: 13341, incorporated herein by reference, can be used. This assay measures phosphorylation of a PKC substrate peptide, which is subsequently separated by binding to phosphocellulose paper. This PKC assay system can be used to measure activity of purified kinase, or the activity in crude cellular extracts. Protein kinase C sample can be diluted in 20 mM HEPES/2 mM DTT immediately prior to assay.

The substrate for the assay is the peptide Ac-FKKSFKL-NH2 (SEQ ID NO: 3), derived from the myristoylated alanine-rich protein kinase C substrate protein (MARCKS). The $K_m$ of the enzyme for this peptide is approximately 50 µM. Other basic, protein kinase C-selective peptides known in the art can also be used, at a concentration of at least 2-3 times their $K_m$.

Cofactors required for the assay include calcium, magnesium, ATP, phosphatidylserine and diacylglycerol. Depending upon the intent of the user, the assay can be performed to determine the amount of PKC present (activating conditions) or the amount of active PKC present (non-activating conditions). For most purposes according to the invention, non-activating conditions will be used, such that the PKC, that is active in the sample when it is isolated, is measured, rather than measuring the PKC that can be activated. For non-activating conditions, calcium is omitted from the assay in favor of EGTA.

The assay is performed in a mixture containing 20 mM HEPES, pH 7.4, 1-2 mM DTT, 5 mM $MgCl_2$, 100 µM ATP, ~1 µCi γ-$^{32}$P-ATP, 100 µg/ml peptide substrate (~100 µM), 140 µM/ 3.8 µM phosphatidylserine/diacylglycerol membranes, and 100 µM calcium (or 500 µM EGTA). 48 µl of sample, diluted in 20 mM HEPES, pH 7.4, 2 mM DTT is used in a final reaction volume of 80 µl. Reactions are performed at 30° C. for 5-10 minutes, followed by addition of 25 µl of 100 mM ATP, 100 mM EDTA, pH 8.0, which stops the reactions.

After the reaction is stopped, a portion (85 µl) of each reaction is spotted onto a Whatman P81 cellulose phosphate filter, followed by washes: four times 500 ml in 0.4% phosphoric acid, (5-10 min per wash); and a final wash in 500 ml 95% EtOH, for 2-5 min. Bound radioactivity is measured by scintillation counting. Specific activity (cpm/nmol) of the labelled ATP is determined by spotting a sample of the reaction onto P81 paper and counting without washing. Units of PKC activity, defined as nmol phosphate transferred per min, are calculated as follows:

The activity, in UNITS (nmol/min) is:

$$= \frac{(\text{cpm on paper}) \times (105 \, \mu l \, \text{total}/85 \, \mu l \, \text{spotted})}{(\text{assay time, min})(\text{specific activity of ATP cpm/nmol})}.$$

An alternative assay can be performed using a Protein Kinase C Assay Kit sold by PanVera (Cat. # P2747).

Assays are performed on extracts from cells expressing a GPR43 polypeptide, treated or not treated with propionate with or without a candidate modulator. Control reactions should be performed using mock-transfected cells, or extracts from them in order to exclude possible non-specific effects of some candidate modulators.

According to the invention, PKC activity is "changed" by a candidate modulator when the units of PKC measured by either assay described above increase or decrease by at least 10%, in extracts from cells expressing GPR43 and treated with a candidate modulator, relative to a reaction performed on a similar sample from cells not treated with a candidate modulator.

f. Kinase Assays:

MAP kinase activity can be assayed using any of several kits available commercially, for example, the p38 MAP Kinase assay kit sold by New England Biolabs (Cat # 9820) or the FlashPlate™ MAP Kinase assays sold by Perkin-Elmer Life Sciences.

MAP Kinase activity is "changed" if the level of activity is increased or decreased by 10% or more in a sample from cells, expressing a GPR43 polypeptide, treated with a candidate modulator relative to MAP kinase activity in a sample from similar cells not treated with the candidate modulator.

Direct assays for tyrosine kinase activity using known synthetic or natural tyrosine kinase substrates and labelled phosphate are well known, as are similar assays for other types of kinases (e.g., Ser/Thr kinases). Kinase assays can be performed with both purified kinases and crude extracts prepared from cells expressing a GPR43 polypeptide, treated with or without propionate, with or without a candidate modulator. Control reactions should be performed using mock-transfected cells, or extracts from them in order to exclude possible non-specific effects of some candidate modulators. Substrates can be either full-length protein or synthetic peptides representing the substrate. Pinna & Ruzzene (1996, Biochem. Biophys. Acta 1314: 191-225, incorporated herein by reference) list a number of phosphorylation substrate sites useful for detecting kinase activities. A number of kinase substrate peptides are commercially available. One that is particularly useful is the "Src-related peptide," RRLIEDAEYAARG (SEQ ID NO: 4; available from Sigma # A7433), which is a substrate for many receptor and nonreceptor tyrosine kinases. Because the assay described below requires binding of peptide substrates to filters, the peptide substrates should have a net positive charge to facilitate binding. Generally, peptide substrates should have at least 2 basic residues and a free amino terminus. Reactions generally use a peptide concentration of 0.7-1.5 mM.

Assays are generally carried out in a 25 µl volume comprising 5 µl of 5×kinase buffer (5 mg/mL BSA, 150 mM Tris-Ci (pH 7.5), 100 mM $MgCl_2$; depending upon the exact kinase assayed for, $MnCl_2$ can be used in place of or in addition to the $MgCl_2$), 5 µl of 1.0 mM ATP (0.2 mM final concentration), γ-32P-ATP (100-500 cpm/pmol), 3 µl of 10 mM peptide substrate (1.2 mM final concentration), cell extract containing kinase to be tested (cell extracts used for kinase assays should contain a phosphatase inhibitor (e.g. 0.1-1 mM sodium orthovanadate)), and $H_2O$ to 25 µl. Reactions are performed at 30° C., and are initiated by the addition of the cell extract.

Kinase reactions are performed for 30 seconds to about 30 minutes, followed by the addition of 45 µl of ice-cold 10% trichloroacetic acid (TCA). Samples are spun for 2 minutes in a microcentrifuge, and 35 µl of the supernatant is spotted onto Whatman P81 cellulose phosphate filter circles. The filters are washed three times with 500 ml cold 0.5% phosphoric acid, followed by one wash with 200 ml of acetone at room temperature for 5 minutes. Filters are dried and incorporated $^{32}P$ is measured by scintillation counting. The specific activity of ATP in the kinase reaction (e.g., in cpm/pmol) is determined by spotting a small sample (2-5 µl) of the reaction onto a P81 filter circle and counting directly, without washing. Counts per minute obtained in the kinase reaction (minus blank) are then divided by the specific activity to determine the moles of phosphate transferred in the reaction.

Tyrosine kinase activity is "changed" if the level of kinase activity is increased or decreased by 10% or more in a sample from cells, expressing a GPR43 polypeptide, treated with a candidate modulator relative to kinase activity in a sample from similar cells not treated with the candidate modulator.

g. Transcriptional Reporters for Downstream Pathway Activation:

The intracellular signal initiated by binding of an agonist to a receptor, e.g., GPR43, sets in motion a cascade of intracellular events, the ultimate consequence of which is a rapid and detectable change in the transcription or translation of one or more genes. The activity of the receptor can therefore be monitored by detecting the expression of a reporter gene driven by control sequences responsive to GPR43 activation.

As used herein "promoter" refers to the transcriptional control elements necessary for receptor-mediated regulation of gene expression, including not only the basal promoter, but also any enhancers or transcription-factor binding sites necessary for receptor-regulated expression. By selecting promoters that are responsive to the intracellular signals resulting from agonist binding, and operatively linking the selected promoters to reporter genes whose transcription, translation or ultimate activity is readily detectable and measurable, the transcription based reporter assay provides a rapid indication of whether a given receptor is activated.

Reporter genes such as luciferase, CAT, GFP, β-lactamase or β-galactosidase are well known in the art, as are assays for the detection of their products.

Genes particularly well suited for monitoring receptor activity are the "immediate early" genes, which are rapidly induced, generally within minutes of contact between the receptor and the effector protein or ligand. The induction of immediate early gene transcription does not require the synthesis of new regulatory proteins. In addition to rapid responsiveness to ligand binding, characteristics of preferred genes useful for making reporter constructs include: low or undetectable expression in quiescent cells; induction that is transient and independent of new protein synthesis; subsequent shut-off of transcription requires new protein synthesis; and mRNAs transcribed from these genes have a short half-life. It is preferred, but not necessary that a transcriptional control element have all of these properties for it to be useful.

An example of a gene that is responsive to a number of different stimuli is the c-fos proto-oncogene. The c-fos gene is activated in a protein-synthesis-independent manner by growth factors, hormones, differentiation-specific agents, stress, and other known inducers of cell surface proteins. The induction of c-fos expression is extremely rapid, often occurring within minutes of receptor stimulation. This characteristic makes the c-fos regulatory regions particularly attractive for use as a reporter of receptor activation.

The c-fos regulatory elements include (see, Verma et al., 1987, Cell 51: 513-514): a TATA box that is required for transcription initiation; two upstream elements for basal transcription, and an enhancer, which includes an element with dyad symmetry and which is required for induction by TPA, serum, EGF, and PMA.

The 20 bp c-fos transcriptional enhancer element located between −317 and −298 bp upstream from the c-fos mRNA cap site, is essential for serum induction in serum starved NIH 3T3 cells. One of the two upstream elements is located at −63 to −57 and it resembles the consensus sequence for cAMP regulation.

The transcription factor CREB (cyclic AMP responsive element binding protein) is, as the name implies, responsive to levels of intracellular cAMP. Therefore, the activation of a receptor that signals via modulation of cAMP levels can be monitored by detecting either the binding of the transcription factor, or the expression of a reporter gene linked to a CREB-binding element (termed the CRE, or cAMP response element). The DNA sequence of the CRE is TGACGTCA. Reporter constructs responsive to CREB binding activity are described in U.S. Pat. No. 5,919,649.

Other promoters and transcriptional control elements, in addition to the c-fos elements and CREB-responsive constructs, include the vasoactive intestinal peptide (VIP) gene promoter (cAMP responsive; Fink et al., 1988, Proc. Natl. Acad. Sci. 85:6662-6666); the somatostatin gene promoter (cAMP responsive; Montminy et al., 1986, Proc. Natl. Acad. Sci. 8.3:6682-6686); the proenkephalin promoter (responsive to cAMP, nicotinic agonists, and phorbol esters; Comb et al., 1986, Nature 323:353-356); the phosphoenolpyruvate carboxy-kinase (PEPCK) gene promoter (cAMP responsive; Short et al., 1986, J. Biol. Chem. 261:9721-9726).

Additional examples of transcriptional control elements that are responsive to changes in GPCR activity include, but are not limited to those responsive to the AP-1 transcription factor and those responsive to NF-κB activity. The consensus AP-1 binding site is the palindrome TGA(C/G)TCA (Lee et al., 1987, Nature 325: 368-372; Lee et al., 1987, Cell 49: 741-752). The AP-1 site is also responsible for mediating induction by tumor promoters such as the phorbol ester 12-O-tetradecanoylphorbol- -acetate (TPA), and are therefore sometimes also referred to as a TRE, for TPA-response element. AP-1 activates numerous genes that are involved in the early response of cells to growth stimuli. Examples of AP-1-responsive genes include, but are not limited to the genes for Fos and Jun (which proteins themselves make up AP-1 activity), Fos-related antigens (Fra) 1 and 2, IκBα, ornithine decarboxylase, and annexins I and II.

The NF-κB binding element has the consensus sequence GGGGACTTTCC (SEQ ID NO: 5). A large number of genes have been identified as NF-κB responsive, and their control elements can be linked to a reporter gene to monitor GPCR activity. A small sample of the genes responsive to NF-κB includes those encoding IL-1β (Hiscott et al., 1993, Mol. Cell. Biol. 13: 6231-6240), TNF-α (Shakhov et al., 1990, J. Exp. Med. 171: 35-47), CCR5 (Liu et al., 1998, AIDS Res. Hum. Retroviruses 14: 1509-1519), P-selection (Pan & McEver, 1995, J. Biol. Chem. 270: 23077-23083), Fas ligand (Matsui et al., 1998, J. Immunol. 161: 3469-3473), GM-CSF (Schreck & Baeuerle, 1990, Mol. Cell. Biol. 10: 1281-1286) and IκBα (Haskill et al., 1991, Cell 65: 1281-1289). Each of these references is incorporated herein by reference. Vectors encoding NF-κB-responsive reporters are also known in the art or can be readily made by one of skill in the art using, for example, synthetic NF-κB elements and a minimal promoter, or using the NF-κB-responsive sequences of a gene known to be subject to NF-κB regulation. Further, NF-κB responsive reporter constructs are commercially available from, for example, CLONTECH.

A given promoter construct should be tested by exposing GPR43-expressing cells, transfected with the construct, to propionate. An increase of at least two-fold in the expression of reporter in response to propionate indicates that the reporter is an indicator of GPR43 activity.

In order to assay GPR43 activity with a transcriptional reporter construct, cells that stably express a GPR43 polypeptide are stably transfected with the reporter construct. To screen for agonists, the cells are left untreated, exposed to candidate modulators, or exposed to propionate, and expression of the reporter is measured. The propionate-treated cultures serve as a standard for the level of transcription induced by a known agonist. An increase of at least 50% in reporter expression in the presence of a candidate modulator indicates that the candidate is a modulator of GPR43 activity. An agonist will induce at least as much, and preferably the same amount or greater reporter expression than propionate alone. This approach can also be used to screen for inverse agonists where cells express a GPR43 polypeptide at levels such that there is an elevated basal activity of the reporter in the absence of propionate or another agonist. A decrease in reporter activity of 10% or more in the presence of a candidate modulator, relative to its absence, indicates that the compound is an inverse agonist.

To screen for antagonists, the cells expressing GPR43 and carrying the reporter construct are exposed to propionate (or another agonist) in the presence and absence of candidate modulator. A decrease of 10% or more in reporter expression in the presence of candidate modulator, relative to the absence of the candidate modulator, indicates that the candidate is a modulator of GPR43 activity.

Controls for transcription assays include cells not expressing GPR43 but carrying the reporter construct, as well as cells with a promoterless reporter construct. Compounds that are identified as modulators of GPR43-regulated transcription should also be analyzed to determine whether they affect transcription driven by other regulatory sequences and by other receptors, in order to determine the specificity and spectrum of their activity.

The transcriptional reporter assay, and most cell-based assays, are well suited for screening expression libraries for proteins for those that modulate GPR43 activity. The libraries can be, for example, cDNA libraries from natural sources, e.g., plants, animals, bacteria, etc., or they can be libraries expressing randomly or systematically mutated variants of one or more polypeptides. Genomic libraries in viral vectors can also be used to express the mRNA content of one cell or tissue in the different libraries used for screening of GPR43.

h) Inositol Phosphates (IP) Measurement

Cells of the invention, for example, CHO-K1 cells, are labelled for 24 hours with 10 μCi/ml [$^3$H] inositol in inositol free DMEM containing 5% FCS, antibiotics, amphotericin, sodium pyruvate and 400 μg/ml G418. Cells are incubated for 2 h in Krebs-Ringer Hepes (KRH) buffer of the following composition (124 mM NaCl, 5 mM KCl, 1.25 mM MgSO$_4$, 1.45 mM CaCl$_2$, 1.25 mM KH$_2$PO$_4$, 25 mM Hepes (pH:7.4) and 8 mM glucose). The cells are then challenged with various SCFA for 30 min. The incubation is stopped by the addition of an ice cold 3% perchloric acid solution. IP are extracted and separated on Dowex columns as previously described (25).

GPR43 Assay

The invention provides for an assay for detecting the activity of a receptor of the invention in a sample. For example, GPR43 activity can be measured in a sample comprising a cell or a cell membrane that expresses GPR43. As above, propionate is used as an example in this section. It should be understood that any SCFA as defined herein can be used in these assays. The assay is performed by incubating the sample in the presence or absence of SCFA and carrying out a second messenger assay, as described above. The results of the second messenger assay performed in the presence or absence of SCFA are compared to determine if the GPR43 receptor is active. An increase of 10% or more in the detected level of a given second messenger, as defined herein, in the presence of SCFA relative to the amount detected in an assay performed in the absence of SCFA is indicative of GPR43 activity.

Any of the assays of receptor activity, including but not limited to the GTP-binding, GTPase, adenylate cyclase, cAMP, phospholipid-breakdown, diacylglycerol, inositol triphosphate, arachidonic acid release (see below), PKC, kinase and transcriptional reporter assays, can be used to determine the presence of an agent in a sample, e.g., a tissue sample, that affects the activity of the GPR43 receptor molecule. To do so, GPR43 polypeptide is assayed for activity in the presence and absence of the sample or an extract of the sample. An increase in GPR43 activity in the presence of the sample or extract relative to the absence of the sample indicates that the sample contains an agonist of the receptor activity. A decrease in receptor activity in the presence of propionate or another agonist and the sample, relative to receptor activity in the presence of propionate alone, indicates that the sample contains an antagonist of GPR43 activity. If desired, samples can then be fractionated and further tested to isolate or purify the agonist or antagonist. The amount of increase or decrease in measured activity necessary for a sample to be said to contain a modulator depends upon the type of assay used. Generally, a 10% or greater change (increase or decrease) relative to an assay performed in the absence of a sample indicates the presence of a modulator in the sample. One exception is the transcriptional reporter assay, in which at least a two-fold increase or 10% decrease in signal is necessary for a sample to be said to contain a modulator. It is preferred that an agonist stimulates at least 50%, and preferably 75% or 100% or more, e.g., 2-fold, 5-fold, 10-fold or greater receptor activation than with propionate alone.

Other functional assays include, for example, microphysiometer or biosensor assays (see Hafner, 2000, Biosens. Bioelectron. 15: 149-158, incorporated herein by reference). The intracellular level of arachidonic acid can also be determined as described in Gijon et al., 2000, J. Biol. Chem., 275:20146-20156.

II. Diagnostic Assays Based upon the Interaction of GPR43 and Propionate:

Signalling through GPCRs is instrumental in the pathology of a large number of diseases and disorders. GPR43, which is expressed in cells of the lymphocyte lineages, platelets, spleen, stomach, lung as well as leukemic cells, can have a role in immune processes, cancer, thrombosis and associated disorders or diseases.

The expression pattern of GPR43 and the knowledge with respect to disorders generally mediated by GPCRs suggests that GPR43 can be involved in disturbances of cell migration, cancer, development of tumours and tumour metastasis, inflammatory and neoplastic processes, wound and bone healing and dysfunction of regulatory growth functions, diabetes, obesity, anorexia, bulimia, acute heart failure, hypotension, hypertension, urinary retention, osteoporosis, angina pectoris, myocardial infarction, restenosis, atherosclerosis, thrombosis and other cardiovascular diseases, autoimmune and inflammatory diseases, diseases characterized by excessive smooth muscle cell proliferation, aneurysms, diseases characterized by loss of smooth muscle cells or reduced smooth muscle cell proliferation, stroke, ischemia, ulcers, allergies, benign prostatic hypertrophy, migraine, vomiting, psychotic and neurological disorders, including anxiety, schizophrenia, manic depression, depression, delirium, dementia and severe mental retardation, degenerative diseases, neurodegenerative diseases such as Alzheimer's disease or Parkinson's disease, and dyskinasias, such as Huntington's disease or Gilles de la Tourett's syndrome and other related diseases including thrombosis and other cardiovascular diseases, autoimmune and inflammatory diseases.

The interaction of GPR43 with propionate can be used as the basis of assays for the diagnosis or monitoring of diseases, disorders or processes involving GPR43 signalling. Diagnostic assays for GPR43-related diseases or disorders can have several different forms. First, diagnostic assays can measure the amount of GPR43 polypeptides, mRNA or ligand in a sample of tissue. Assays that measure the amount of mRNA encoding GPR43 polypeptide also fit into this category. Second, assays can evaluate the qualities of the receptor or the ligand. For example, assays that determine whether an individual expresses a mutant or variant form of GPR43 can be used diagnostically. Third, assays that measure one or more activities of GPR43 polypeptide can be used diagnostically.

A. Assays that Measure the Amount of GPR43 Polypeptide

GPR43 levels can be measured and compared to standards in order to determine whether an abnormal level of the receptor or its ligand is present in a sample, either of which indicate probable dysregulation of GPR43 signalling. Polypeptide levels are measured, for example, by immunohistochemistry using antibodies specific for the polypeptide. A sample isolated from an individual suspected of suffering from a disease or disorder characterized by GPR43 activity is contacted with an antibody for a GPR43 polypeptide, and binding of the antibody is measured as known in the art (e.g., by measurement of the activity of an enzyme conjugated to a secondary antibody).

Another approach to the measurement of GPR43 levels uses flow cytometry analysis of cells from an affected tissue. Methods of flow cytometry, including the fluorescent labeling of antibodies specific for GPR43, are well known in the art. Other approaches include radioimmunoassay or ELISA. Methods for each of these are also well known in the art.

The amount of binding detected is compared to the binding in a sample of similar tissue from a healthy individual, or from a site on the affected individual that is not so affected. An increase of 10% or more relative to the standard is diagnostic for a disease or disorder characterized by GPR43 dysregulation.

GPR43 expression can also be measured by determining the amount of mRNA encoding the polypeptides in a sample of tissue. Levels of mRNA can be measured by quantitative or semi-quantitative PCR. Methods of "quantitative" amplification are well known to those of skill in the art, and primer sequences for the amplification of GPR43 nucleic acid are disclosed herein. A common method of quantitative PCR involves simultaneously co-amplifying a known quantity of a control sequence using the same primers. This provides an internal standard that can be used to calibrate the PCR reaction. Detailed protocols for quantitative PCR are provided in *PCR Protocols, A Guide to Methods and Applications*, Innis et al., Academic Press, Inc. N.Y., (1990), which is incorporated herein by reference. An increase of 10% or more in the amount of mRNA encoding GPR43 in a sample, relative to the amount expressed in a sample of like tissue from a healthy individual or in a sample of tissue from an unaffected location in an affected individual is diagnostic for a disease or disorder characterized by dysregulation of GPR43 signalling.

B. Qualitative Assays

Assays that evaluate whether or not a GPR43 polypeptide or the mRNA encoding it are wild-type or not can be used diagnostically. In order to diagnose a disease or disorder characterized by GPR43 dysregulation in this manner, RNA isolated from a sample is used as a template for PCR amplification of GPR43. The amplified sequences are then either directly sequenced using standard methods, or are first cloned into a vector, followed by sequencing. A difference in the sequence that changes one or more encoded amino acids relative to the sequence of wild-type GPR43 can be diagnostic of a disease or disorder characterized by dysregulation of GPR43 signalling. It can be useful, when a change in coding sequence is identified in a sample, to express the variant receptor or ligand and compare its activity to that of wild type GPR43. Among other benefits, this approach can provide novel mutants, including constitutively active and null mutants.

In addition to standard sequencing methods, amplified sequences can be assayed for the presence of specific mutations using, for example, hybridization of molecular beacons that discriminate between wild type and variant sequences. Hybridization assays that discriminate on the basis of changes as small as one nucleotide are well known in the art. Alternatively, any of a number of "minisequencing" assays can be performed, including, those described, for example, in U.S. Pat. Nos. 5,888,819, 6,004,744 and 6,013,431 (incorporated herein by reference). These assays and others known in the art can determine the presence, in a given sample, of a nucleic acid with a known polymorphism.

If desired, array or microarray-based methods can be used to analyze the expression or the presence of mutation, in GPR43 sequences. Array-based methods for minisequencing and for quantitation of nucleic acid expression are well known in the art.

C. Functional Assays.

Diagnosis of a disease or disorder characterized by the dysregulation of GPR43 signalling can also be performed using functional assays. To do so, cell membranes or cell extracts prepared from a tissue sample are used in an assay of GPR43 activity as described herein (e.g., ligand binding assays, the GTP-binding assay, GTPase assay, adenylate cyclase assay, cAMP assay, arachidonic acid level, phospholipid breakdown, diacyl glycerol or inositol triphosphate assays, PKC activation assay, or kinase assay). The activity detected is compared to that in a standard sample taken from a healthy individual or from an unaffected site on the affected individual. As an alternative, a sample or extract of a sample can be applied to cells expressing GPR43, followed by measurement of GPR43 signalling activity relative to a standard sample. A difference of 10% or more in the activity measured in any of these assays, relative to the activity of the standard, is diagnostic for a disease or disorder characterized by dysregulation of GPR43 signalling.

Modulation of GPR43 Activity in a Cell According to the Invention

The discovery of propionate as a ligand of GPR43 provides methods of modulating the activity of a GPR43 polypeptide in a cell. GPR43 activity is modulated in a cell by delivering to that cell an agent that modulates the function of a GPR43 polypeptide. This modulation can be performed in cultured cells as part of an assay for the identification of additional modulating agents, or, for example, in an animal, including a human. Agents include propionate and other SCFAs as defined herein, as well as additional modulators identified using the screening methods described herein including but not limited to any of the propionate analogues.

An agent can be delivered to a cell by adding it to culture medium. The amount to deliver will vary with the identity of the agent and with the purpose for which it is delivered. For example, in a culture assay to identify antagonists of GPR43 activity, one will preferably add an amount of agent, e.g., propionate that half-maximally activates the receptors (e.g., approximately $EC_{50}$), preferably without exceeding the dose required for receptor saturation. This dose can be determined by titrating the amount of propionate to determine the point at which further addition of propionate has no additional effect on GPR43 activity.

When a modulator of GPR43 activity is administered to an animal for the treatment of a disease or disorder, the amount administered can be adjusted by one of skill in the art on the basis of the desired outcome. Successful treatment is achieved when one or more measurable aspects of the pathology (e.g., tumor cell growth, accumulation of inflammatory cells) is changed by at least 10% relative to the value for that aspect prior to treatment.

Candidate Modulators Useful According to the Invention

The invention provides for a compound that is a modulator of a receptor of the invention.

Preferably a candidate modulator is a Short chain fatty acid or a carboxylic acid.

The candidate compound can be a synthetic compound, or a mixture of compounds, or may be a natural product (e.g. a plant extract or culture supernatant). A candidate compound according to the invention includes but is not limited to a small molecule that can be synthesized, a natural extract, peptides, polypeptides, carbohydrates, lipids, an antibody or antigen-binding fragment thereof, nucleic acids, and a small organic molecules.

Candidate modulator compounds from large libraries of synthetic or natural compounds can be screened. Numerous means are currently used for random and directed synthesis of saccharide, peptide, and nucleic acid based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and can be prepared. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds are readily modified through conventional chemical, physical, and biochemical means.

Useful compounds may be found within numerous chemical classes. Useful compounds may be organic compounds, or small organic compounds. Small organic compounds have a molecular weight of more than 50 yet less than about 2,500 daltons, preferably less than about 750, more preferably less than about 350 daltons. Exemplary classes include heterocycles, peptides, saccharides, steroids, and the like. The compounds may be modified to enhance efficacy, stability, pharmaceutical compatibility, and the like. Structural identification of an agent may be used to identify, generate, or screen additional agents. For example, where peptide agents are identified, they may be modified in a variety of ways to enhance their stability, such as using an unnatural amino acid, such as a D-amino acid, particularly D-alanine, by functionalizing the amino or carboxylic terminus, e.g. for the amino group, acylation or alkylation, and for the carboxyl group, esterification or amidification, or the like.

For primary screening, a useful concentration of a candidate compound according to the invention is from about 10 µM to about 100 µM or more (i.e. 1 mM, 10 mM, 100 mM, or even 1M), but can also be 1 nM and higher, 1 pM and higher, or 1 fM and higher. The primary screening concentration will be used as an upper limit, along with nine additional concentrations, wherein the additional concentrations are determined by reducing the primary screening concentration at half-log intervals (e.g. for 9 more concentrations) for secondary screens or for generating concentration curves.

Antibodies Useful According to the Invention

The invention provides for antibodies to GPR43. Antibodies can be made using standard protocols known in the art (See, for example, Antibodies: A Laboratory Manual ed. by Harlow and Lane (Cold Spring Harbor Press: 1988)). A mammal, such as a mouse, hamster, or rabbit can be immunized with an immunogenic form of the peptide (e.g., GPR43 polypeptide or an antigenic fragment which is capable of eliciting an antibody response, or a fusion protein as described herein above). Immunogens for raising antibodies are prepared by mixing the polypeptides (e.g., isolated recombinant polypeptides or synthetic peptides) with adjuvants. Alternatively, GPR43 polypeptides or peptides are made as fusion proteins to larger immunogenic proteins. Polypeptides can also be covalently linked to other larger immunogenic proteins, such as keyhole limpet hemocyanin. Alternatively, plasmid or viral vectors encoding GPR43 polypeptide, or a fragment of these proteins, can be used to express the polypeptides and generate an immune response in an animal as described in Costagliola et al., 2000, J. Clin. Invest. 105:803-811, which is incorporated herein by reference. In order to raise antibodies, immunogens are typically administered intradermally, subcutaneously, or intramuscularly to experimental animals such as rabbits, sheep, and mice. In addition to the antibodies discussed above, genetically engineered antibody derivatives can be made, such as single chain antibodies.

The progress of immunization can be monitored by detection of antibody titers in plasma or serum. Standard ELISA, flow cytometry or other immunoassays can also be used with the immunogen as antigen to assess the levels of antibodies. Antibody preparations can be simply serum from an immunized animal, or if desired, polyclonal antibodies can be isolated from the serum by, for example, affinity chromatography using immobilized immunogen.

To produce monoclonal antibodies, antibody-producing splenocytes can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with GPR43 polypeptide, and monoclonal antibodies isolated from the media of a culture comprising such hybridoma cells.

High Throughput Screening Kit

A high throughput screening kit according to the invention comprises all the necessary means and media for performing the detection of a modulator compound including an agonist, antagonist, inverse agonist or inhibitor to the receptor of the invention in the presence of propionate, preferably at a concentration in the range of 1 µM to 1 mM. The kit comprises materials to perform the following successive steps. Recombinant cells of the invention, comprising and expressing the nucleotide sequence encoding the GPR43 receptor, are grown on a solid support, such as a microtiter plate, more preferably a 96 well microtiter plate, according to methods well known to the person skilled in the art, especially as described in WO 00/02045. Modulator compounds according to the invention, at concentrations from about 1 µM to 1 mM or more, are added to the culture media of defined wells in the presence of an appropriate concentration of propionate (preferably in the range of 1 µM to 1 µM).

Kits according to the invention can also comprise materials necessary for second messenger assays amenable to high throughput screening analysis, including but not limited to the measurement of intracellular levels of cAMP, intracellular inositol phosphate, intracellular diacylglycerol concentrations, arachinoid acid concentration or MAP kinase or tyrosine kinase activity (as decribed above). For example, the GPR43 activity, as measured in a cyclic AMP assay, is quantified by a radioimmunoassay as previously described (26). Results are compared to the baseline level of GPR43 activity obtained from recombinant cells according to the invention in the presence of propionate but in the absence of added modulator compound. Wells showing at least 2 fold, preferably 5 fold, more preferably 10 fold and most preferably a 100 fold or more increase or decrease in GPR43 activity as compared to the level of activity in the absence of modulator, are selected for further analysis.

Other Kits Useful According to the Invention

The invention provides for kits useful for screening for modulators of GPR43 activity, as well as kits useful for diagnosis of diseases or disorders characterized by dysregulation of GPR43 signalling. Kits useful according to the invention can include an isolated GPR43 polypeptide (including a membrane-or cell-associated GPR43 polypeptide, e.g., on isolated membranes, cells expressing GPR43, or on an SPR chip). A kit can also comprise an antibody specific for GPR43. Alternatively, or in addition, a kit can contain cells transformed to express GPR43 polypeptide. In a further embodiment, a kit according to the invention can contain a polynucleotide encoding a GPR43 polypeptide. In a still further embodiment, a kit according to the invention may comprise the specific primers useful for amplification of GPR43 as described below. All kits according to the invention will comprise the stated items or combinations of items and packaging materials therefor. Kits will also include instructions for use.

Transgenic Animals

Transgenic mice provide a useful tool for genetic and developmental biology studies and for the determination of the function of a novel sequence. According to the method of conventional transgenesis, additional copies of normal or modified genes are injected into the male pronucleus of the zygote and become integrated into the genomic DNA of the recipient mouse. The transgene is transmitted in a Mendelian manner in established transgenic strains. Constructs useful for creating transgenic animals comprise genes under the control of either their normal promoters or an inducible promoter, reporter genes under the control of promoters to be analyzed with respect to their patterns of tissue expression and regulation, and constructs containing dominant mutations, mutant promoters, and artificial fusion genes to be studied with regard to their specific developmental outcome. Typically, DNA fragments on the order of 10 kilobases or less are used to construct a transgenic animal (Reeves, 1998, New. Anat., 253:19). Transgenic animals can be created with a construct comprising a candidate gene containing one or more polymorphisms according to the invention. Alternatively, a transgenic animal expressing a candidate gene containing a single polymorphism can be crossed to a second transgenic animal expressing a candidate gene containing a different polymorphism and the combined effects of the two polymorphisms can be studied in the offspring animals.

Other Transgenic Animals

The invention provides for transgenic animals that include but are not limited to transgenic mice, rabbits, rats, pigs, sheep, horses, cows, goats, etc. A protocol for the production of a transgenic pig can be found in White and Yannoutsos, Current Topics in Complement Research: 64$^{th}$ Forum in Immunology, pp. 88-94; U.S. Pat. No. 5,523,226; U.S. Pat. No. 5,573,933: PCT Application WO93/25071; and PCT Application WO95/04744. A protocol for the production of a transgenic mouse can be found in U.S. Pat. No. 5,530,177. A protocol for the production of a transgenic rat can be found in Bader and Ganten, Clinical and Experimental Pharmacology and Physiology, Supp. 3:S81-S87, 1996. A protocol for the production of a transgenic cow can be found in Transgenic Animal Technology, A Handbook, 1994, ed., Carl A. Pinkert, Academic Press, Inc. A protocol for the production of a transgenic rabbit can be found in Hammer et al., Nature 315:680-683, 1985 and Taylor and Fan, Frontiers in Bioscience 2:d298-308, 1997.

Knock Out Animals i. Standard

Knock out animals are produced by the method of creating gene deletions with homologous recombination. This technique is based on the development of embryonic stem (ES) cells that are derived from embryos, are maintained in culture and have the capacity to participate in the development of every tissue in the mouse when introduced into a host blastocyst. A knock out animal is produced by directing homologous recombination to a specific target gene in the ES cells, thereby producing a null allele of the gene. The potential phenotypic consequences of this null allele (either in heterozygous or homozygous offspring) can be analyzed (Reeves, supra).

ii. In vivo Tissue Specific Knock Out in Mice Using Cre-lox.

The method of targeted homologous recombination has been improved by the development of a system for site-specific recombination based on the bacteriophage P1 site specific recombinase Cre. The Cre-loxP site-specific DNA recombinase from bacteriophage P1 is used in transgenic mouse assays in order to create gene knockouts restricted to defined tissues or developmental stages. Regionally restricted genetic deletion, as opposed to global gene knockout, has the advantage that a phenotype can be attributed to a particular cell/tissue (Marth, 1996, Clin. Invest. 97: 1999). In the Cre-loxP system one transgenic mouse strain is engineered such that loxP sites flank one or more exons of the gene of interest. Homozygotes for this so called 'floxed gene' are crossed with a second transgenic mouse that expresses the Cre gene under control of a cell/tissue type transcriptional promoter. Cre protein then excises DNA between loxP recognition sequences and effectively removes target gene function (Sauer, 1998, Methods, 14:381). There are now many in vivo examples of this method, including the inducible inactivation of mammary tissue specific genes (Wagner et al., 1997, Nucleic Acids Res., 25:4323).

iii. Bac Rescue of Knock Out Phenotype

In order to verify that a particular genetic polymorphism/mutation is responsible for altered protein function in vivo one can "rescue" the altered protein function by introducing a wild-type copy of the gene in question. In vivo complementation with bacterial artificial chromosome (BAC) clones expressed in transgenic mice can be used for these purposes. This method has been used for the identification of the mouse circadian Clock gene (Antoch et al., 1997, Cell 89: 655).

Materials

Trypsin was from Flow Laboratories (Bioggio, Switzerland). Culture media, G418, fetal bovine serum (FBS), restriction enzymes, Platinum Pfx and Taq DNA polymerases were purchased from Life Technologies, Inc. (Merelbeke, Belgium). The radioactive product myo-D-[2-$^3$H] inositol (17.7 Ci/mmol) was from Amersham (Ghent, Belgium). Dowex AG1X8 (formate form) was from Bio-Rad Laboratories (Richmond, Calif.). ATP, propionate, acetate, formate, butyrate, valerate, beta-hydroxybutyrate, gamma-hydroxybutyrate and other carboxylic acids were obtained from Sigma Chemical Co. (St. Louis, Mo.). Forskolin was purchased from Calbiochem (Bierges, Belgium). Rolipram was a gift from the Laboratories Jacques Logeais (Trappes, France). pEFIN5 is an expression vector developed by Euroscreen (Brussels, Belgium). Monoclonal antibody specific for the dually phosphorylated forms of Erk1 and Erk2 (at Thr$^{202}$ and Tyr$^{204}$) was obtained from New England Biolabs (Beverly, Mass.).

Dosage and Mode of Administration

By way of example, a patient can be treated as follows by the administration of a modulator of GPR43 (for example, an agonist, antagonist or inhibitor of GPR43, of the invention). A modulator of GPR43 the invention can be administered to the patient, preferably in a biologically compatible solution or a pharmaceutically acceptable delivery vehicle, by ingestion, injection, inhalation or any number of other methods. The dosages administered will vary from patient to patient; a "therapeutically effective dose" can be determined, for example, by the level of enhancement of function (e.g., as determined in a second messenger assay described herein). Monitoring propionate binding will also enable one skilled in the art to select and adjust the dosages administered. The dosage of a modulator of GPR43 of the invention may be repeated daily, weekly, monthly, yearly, or as considered appropriate by the treating physician.

In one embodiment, a patient can be treated to modulate the signalling activity of a GPR43 receptor by administering to a patient a sublethal dose of an agent which inhibits or promotes the signalling activity of GPR43. A sublethal dose according to the invention, refers to a dose of an agent for inhibiting or stimulating a GPR43 signalling activity which is at or below the LD50 for the particular agent. In one embodiment, the dose of an agent which inhibits the signalling activity of GPR43 is between 1 aM and 1 M, preferably between 1 fM and 1 mM, and more preferably between 1 nM and 1 µM. In one embodiment, an agent useful for the modulation of GPR43 signalling may be an antibody which specifically binds to the ligand binding site of GPR43. An amount of anti-GPR43 antibody needed to achieve a dosage useful for the modulation of GPR43 signalling will depend upon the level of expression of GPR43, localization of receptor expression, and general state of the patient's own immune system, but generally range from 0.0005 to 5.0 mg of anti-GPR43 antibody or binding protein thereof per kilogram of body weight, with doses of 0.05 to 2.0 mg/kg/dose being more commonly used.

Pharmaceutical Compositions

The invention provides for compositions comprising a GPR43 modulator according to the invention admixed with a physiologically compatible carrier. As used herein, "physiologically compatible carrier" refers to a physiologically acceptable diluent such as water, phosphate buffered saline, or saline, and further may include an adjuvant. Adjuvants such as incomplete Freund's adjuvant, aluminium phosphate, aluminium hydroxide, or alum are materials well known in the art.

The invention also provides for pharmaceutical compositions. In addition to the active ingredients, these pharmaceutical compositions may contain suitable pharmaceutically acceptable carrier preparations which can be used pharmaceutically.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank's solution, Ringer' solution, or physiologically buffered saline. Aqueous injection suspensions may contain substances which increase the viscosity of the suspension, such as sodium carboxymethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For nasal administration, penetrants appropriate to the particular barrier to be permeated are used in the formulation. Such penetrants are generally known in the art.

The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. . . . Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition with information including amount, frequency and method of administration.

Modulation of Chemotaxis

The present invention provides a method for the modulation of the chemotaxis of PMN, and related cells in vitro or in vivo by contacting the cells with short chain fatty acid molecules of the invention. Migration of immune cells to sites of infection (or the site of antigen presence) is a common process which occurs in myriad disease states. The present invention is based, in part, on the discovery that GPR43 functions as a receptor for short chain fatty acids, such as acetate and propionate, and is responsible for mediating PMN chemotaxis in response to such SCFAs. Accordingly, the invention provides a mechanism for the modulation and/or treatment of disease states which share, as a common mechanism of action, the phenomenon of PMN cell migration. In one embodiment, the invention provides that disease states which are characterized by unwanted migration of immune cells, such as autoimmune diseases, may be modulated and/or treated by administering to a patient with such a disease an agent which inhibits a signalling activity of GPR43, or which blocks the activation of the receptor (e.g., an antibody which specifically binds to the GPR43 receptor). Alternatively, the invention provides that disease states which are characterized by insufficient immune cell migration, or diseases caused by pathogens which must be eliminated through the stimulation of an immune response may be modulated or treated by administering to a patient in need thereof, an agonist of the GPR43 receptor, including, but not limited to acetate and/or propionate. Particular diseases which may be modulated and/or treated by the methods of the invention are indicated below. The present invention is not limited, however, to these specific diseases, and may be useful in the treatment of other disease states characterized by abnormal, or insufficient immune cell migration. Accordingly, a "PMN chemotaxis-related disease" as used herein refers to a disease which includes as a component, migration of PMN cells toward or away from a soluble chemotactic factor. A "PMN chemotaxis-related disease" can be, for example, an inflammatory disease, autoimmune diseases, IBD (Inflammatory Bowel Diseases), liver cirrhosis, periodontal disease, and other diseases which are known to those of skill in the art to be mediated, at least in part, by the migration of PMN cells towards or away from a soluble chemotactic factor. A "PMN chemotaxis-related disease" can also refer to a pathologial condition resulting from infection by a pathogen, or from abnormal proliferation of an endogenous pathogen in an individual.

Intestine-Related Disorders:

It is possible that products of the commensal flora promote inflammation in the presence of an impaired mucosal barrier or injury to the mucosa (Chadwick & Anderson, 1990), leading to activation of the mucosal immune system in inflammatory bowel diseases (IBD) (Chadwick et al., 2002). IBD can involve either or both of the small and large bowel. Crohn's disease and ulcerative colitis are the best known forms of IBD. The predominant histopathologic feature of IBD is infiltration of acute and chronic inflammatory cells in the affected intestine. These immune cells can recognize and destroy intestinal cells, implicating classical immune mechanisms in IBD pathogenesis (Perlmann & Broberger, 1963). In addition, immune cells can infiltrate intestine diffusely in the absence of obvious morphological, clinical and endoscopic evidence of inflammation (Fiocchi, 1998). Monocytic cells appear also to be involved in all stages of IBD, underscoring their importance in IBD pathophysiology (Fiocchi, 1998). In addition, activated T lymphocytes induce mucosal damage in organ culture (MacDonald & Spencer, 1988) and PMN are playing a key role in the amplification of inflammation and tissue damage (Fiocchi, 1998), with a prominent neutrophil infiltration in the inflamed colonic mucosa of patients with IBD. After migration from the systemic circulation into the mucosal interstitial space, neutrophils may subsequently undergo activation to produce reactive oxygen intermediates and additional chemokines, leading to perpetuation of the inflammatory response as well as the ultimate mucosal injury. Because neutrophil infiltration is an integral component of the severely-inflamed intestine with IBD, the development of therapeutic strategies to block neutrophil migration and activation is a highly desirable target. Indeed, treatment with cyclosporin A, an inhibitor of migratory response of neutrophils, improved the inflammation of IBD patients by decreasing the inflammation due to neutrophils and lymphocytes T (Ina et al., 2002). The concept that the normal flora somehow functions as a modulator of physiological inflammation has been strengthened substantially by the observations of Duchmann et al. (Duchmann et al., 1995 & 1996). They have shown that mucosal but not peripheral blood, mononuclear cells from patients with IBD proliferate when exposed to autologous intestinal bacteria. Production of factors in the colonic milieu markedly increase production of reactive oxygen species by PMNs. Amongst these factors, SCFA are produced by anaerobic fermentation of complex carbohydrates in intestine (Pouteau et al., 1996; Topping & Clifton, 2001-Eftimiadi et al., 1987), mainly acetate, propionate and butyrate with partition as follows: acetate (60%), propionate (25%) and butyrate (15%). The colon luminal total concentration is around 70-100 mM (Sellin, 1999). Propionate and acetate, but not butyrate, are potent modulators of neutrophil function (Nakao et al., 1992) and we showed that acetate and propionate are acting on GPR43 as agonists to modulate neutrophil activities. Therefore an antagonist of GPR43 might decrease neutrophil activation and inflammation in IBD.

Because of a key role of neutrophils migration and activation in the activation of the mucosal immune system in IBD, compounds which are antagonists of GPR43 receptor signaling may be useful, according to the invention, to decrease neutrophil activation and inflammation in IBD.

Host Defense, Inflammation, Modulation of Innate Immunity and Hematopoietic Disorders GPR43 is expressed on leukocytes. The ligands of GPR43, propionate and acetate, are modulating polymorphonuclear cells as well as T lymphocytes and monocytes (Eftimiadi et al., 1991; Nakao et al., 1992; Curi et al., 1993). But none of these effects have been associated with the simulation of a given G-protein coupled receptor (GPCR), although experiments with pertussis toxin and activator/inhibitor of protein kinase C may have suggested a GPCR-mechanism. Brunkhorst et al (1992) has suggested a GPCR mechanism of action, for at least propionate and acetate, on a series of PMN-activation events such as cytoskeletal F-actin alterations, PMN polarization, F-actin localization, cytoplasmic pH oscillation, cell shape. The present invention provides that ligands of GPR43 could be used to modulate leukocyte activity in different pathologies, including, but not limited to inflammatory diseases, pathogen infection, lymphomas and leukemias to modulate leukocyte activity.

Periodontal Diseases

Periodontal disease is the consequence of a mixed Gram-negative infection in the gingival sulcus and has been associated with deficits in the neutrophil response. One potential approach to therapy is the use of biological-response modulators that enhance the neutrophil response. Various periodontal and root canal pathogens, such as the Bacteroides species, can produce significant amounts of short chain fatty acids (SCFA). Accordingly, the a GPR43 ligand, as provided by the present invention, may be useful to modulate the neutrophil response and decrease the symptoms of periodontal diseases.

Alcoholism

Most ethanol elimination occurs by oxidation to acetaldehyde and acetate catalysed principally by alcohol deshydrogenase (ADH) and aldehyde deshydrogenase (ALDH). Alcohol is eliminated from the body almost entirely by hepatic metabolism first to acetaldehyde and then to acetate and finally to carbon dioxide and water following a time-course of elimination best described by Michaelis-Menten kinetics (Fujimiya et al. 2000 Alcohol Clin Exp Res 24:16S-20S; see Li and Bosron, 1986 Ann Emerg Med 15:997-1004). Approximately 60%-75% of ethanol dose is converted to acetate (Siler S Q, Neese R A, Hellerstein M K 1999 Am J Clin Nutr 70(5):928-36). Acetate can be assessed in human blood and urine by headspace gas chromatography (Tsukamoto et al. Nihon Arukoru Yakubutsu Igakkai Zasshi 1998 3:200-9) and represents a marker for alcohol intake, heavy drinking, metabolic tolerance, abuse, chronic alcoholism and alcohol withdrawal severity (Pronko et al. 1997 Alcohol 32:761-8; Korri et al. 1985 Alcohol Clin Exp Res 9:468-71; Nuutinen et al. 1985 Alcohol 2:623-6). After ethanol, it increases to 19-57 mg/ml (Lundquist 1962 Nature N°4815, p579).

Chronic and even acute moderate alcohol use can increase host susceptibility to infections caused by bacterial and viral pathogens (i.e. Klebsiella pneumoniae (Shellito et al. 2001 25:872-81); and lung clearance of Pseudomonas aeruginosa (Greensberg et al. 1999 Alcohol Clin Exp Res 23:735-44); phagocytosis of staphylococcus aureus and epidermidis (Jareo et al., 1995 Alcohol 30:311-8; Corberand et al. 1989, Alcohol Clin Exp Res 13:542-6). Impaired host defense after alcohol exposure appears to be linked to a combination of decreased inflammatory response, altered cytokine production and abnormal reactive oxygen intermediate generation and Neutrophils functions (Szabo 1999). The sensitivity of the signaling cascade inositol phosphate (IP)/Ca2+ response in neutrophils from healthy volunteers after ingestion of 1% ethanol for 2 h is altered (Gann et al., Psychiatry Res 1999 89:189-99). Damage of PMN function by ethanol consists of ultrastructural changes of neutrophil granules, and further includes a reduction, redistribution and a typical accumulation of autophagic vacuoles (Todorovic 1999, Indian J Med Res 109:105-14; Todorovic et al. 1994, J Stud Alcohol 55:239-48), and changes in neutrophil elastase activity (Sachs et al. 1990, Am Rev Respir Dis 141:1249-55). These phenomena may accordingly promote a deficit in neutrophil bactericidal activity against germs. In addition, chronic ethanol intake modulates f-met-leu-phe (fMLP) induced chemotactic activity and superoxide production by neutrophils (Bautista et al. 1992 16:788-94).

Leucocyte infiltration in the liver is also one of the most important features of alcoholic liver disease. In alcoholic hepatitis, PMN selectively migrate to the liver (Bautista, Alcohol 2002 27:17-21; Siratori et al. 1992 J Hepatol 15:266-8). Up-regulation of chemokines in the circulation and tissue is associated with enhanced neutrophilic infiltration in the liver (Bautista, Alcohol 2002 27:17-21). In cirrhotic alcoholics chemotaxis, phagocytosis and bactericidal activity were all significantly reduced (Laharrague et al. 1985 Ann Med Interne (Paris) 136:210-2)

Acetate is capable of producing a fall in free fatty acid (FFA) after ethanol ingestion, since ethanol is able to lower circulating FFA to healthy volunteers. Increase in blood acetate after ethanol is sufficient to explain the FFA fall even without acidosis, acetate being known as an alkalinizing agent (Crouse J R, Gerson C D, DeCarli L M, Lieber C S. 1968 J Lipid Res 9(4):509-12).

Accordingly, the above suggests that neutrophil function may be impaired in chronic alcohol abusers, and therefore a ligand of GPR43, according to the invention, may be useful to restore neutrophil function.

Measuring Chemotaxis

PMN chemotaxis may be measured in vitro, according to the invention, by procedures originally developed by S. Boyden in 1962. (See, S. Boyden, J. Exp. Med. 115: pp. 453-466, 1962). Briefly, the procedure involves placing a suspension of PMN cells and a chemical agent in two separate chambers, which chambers are separated by a polycarbonate filter. The PMN may, for example, be prepared from the peripheral blood of a mammal. After a predetermined period of time, the filter is removed and cells on the filter surface closest to the chamber containing the cell suspension are carefully removed. The remaining cells on the filter are then fixed and stained. Using a high power microscope, the filter is examined and the number of cells appearing on the underside of the filter (i.e., the side of the filter closest to the chamber containing the chemical agent) are counted manually. A positive chemotactic response is indicated by the cells having migrated or "crawled" through the filter to the side closest to the chamber containing the chemical agent. Because of the time required to do so, typically the entire filter is not examined. Rather, representative sample areas are examined and counted. According to the invention, "PMN chemotaxis" is said to have occurred where there are at least 10% more PMN cells on the filter surface aposed to the chamber containing the chemotactic factor when the chemotactic factor is present in the chamber, than when the chemotactic factor is not present.

Alternatively, PMN chemotaxis may be assessed in vivo in a mammal by comparing the number of PMN cells at a given site or in a given sample at two different time points. Upon appropriate stimulus, PMN cells migrate from the peripheral blood circulation into the connective tissue, and surrounding strucutres. To determine whether chemotaxis has been modulated, for example, in response to a candidate agent such as a modulator of GPR43 signalling activity, a connective tissue sample may be obtained from a mammal and examined, using histological techniques well known to those of skill in the art, to determine the number of PMN cells present in the peripheral tissues (such as connective tissue or lymphoid organs). The number of PMN cells present may then be compared with the number present at a later time point (e.g., 1-5 hours, 1-5 days, or 1-5 weeks later). In one embodiment, the number of PMN cells present in the tissues of a mammal is compared with the number present after the administration of a candidate agent, wherein an increase or decrease in the number of PMN cells present in peripheral tissues following administration of the candidate agent identifies the agent as a modulator of PMN chemotaxis.

EXAMPLES

The invention is illustrated by the following non-limiting examples wherein the following materials and methods are employed. The entire disclosure of each of the literature references cited hereinafter are incorporated by reference herein.

Example 1

Cloning, Sequencing and Alignment

Specific oligonucleotide primers were synthesized on the basis of the sequence of the GPR43 human receptor: a sense primer 5'-GCGGAATTCACCATGCTGCCGG ACTGGAAGAG-3' (SEQ ID NO: 6) and an antisense primer 5'-CTAGTCTAG ACTGCTACTCTGTAGTGAAGTC-3' (SEQ ID NO: 7). A polymerase chain reaction (PCR) was performed on three different spleen cDNAs using the Platinum Pfx DNA Polymerase. The amplification conditions were as follows: 94° C., 15 s; 50° C., 30 s; 68° C., 2 min for 35 cycles. Amplifications resulted in a fragment of 1 kilobase containing the entire coding sequence of the GPR43 gene. The coding sequence was then subcloned between the EcorI and XbaI sites of the pcDNA3 (Invitrogen) expression vector and sequenced on both strands for each of the three cDNAs using the BigDye Terminator cycle sequencing kit (Applied Biosystems, Warrington, Great Britain).

This 990 base pair (bp)-open reading frame was also identified recently by Sawzdargo et al. (GenBank accession AF024690) and reported to encode an orphan G-protein-coupled receptor that they called GPR43. Oligonucleotide primers were synthesized on the basis of this coding sequence published in Sawzdargo et al. They were used in PCR starting from spleen cDNA. A PCR product with a size compatible with GPR43 coding sequence was inserted into the pcDNA3 expression vector and sequenced on both strands (FIG. 1). The putative membrane-spanning domains are underlined and numbered I to VII. The putative sites of phosphorylation by caseine kinase is indicated in bold.

Alignment of the amino acid sequence of GPR43 (FIG. 2) with PAR1 and other PAR related sequences was performed using the ClustalX algorithm. The dendrogram of FIG. 2 was then constructed using the TreeView algorithm. The figure shows the relationship of GPR43 with Proteinase Activated Receptor (PAR)-1, -2, -3, and-4, platelet-activating factor receptor (PAF), and G-protein coupled receptor 42 (GPR42). The latter is always an orphan receptor.

Example 2

Tissue Distribution of GPR43 Human Receptor

GPR43 mRNA was amplified by RT-PCR in several human tissues (FIG. 3).

Reverse transcription-polymerase chain reaction (RT-PCR) experiments were carried out using a panel of polyA$^+$ RNA (Clontech). The GPR43 primers were as follows: GPR43 sense primer (5'-ACTGGAAGAGCTCCTTGATC-3'; SEQ ID NO: 8) and GPR43 antisense primer (5'-CAAG-TATTGAACGATGATC-3'; SEQ ID NO: 9). The expected size of the amplified DNA band was 439 bp. Two primers synthesized on the basis of aldolase coding sequence were used as controls to produce a product with an expected size of 443 bp: aldolase sense primer 5'-GGCAAGGGCATC-CTGGCTGC-3' (SEQ ID NO: 10) and aldolase antisense reverse 5'-TAACGGG CCAGAACATTGGCATT-3' (SEQ ID NO: 11). Approximately 75 ng of poly A$^+$ RNA was reverse transcribed with Superscript II (Life Technologies, Inc., Merelbeke, Belgium) and used for PCR. PCR was performed using the Taq polymerase under the following conditions: denaturation at 94° C. for 3 min, 38 cycles at 94° C. for 1 min, 58° C. for 2 min and 72° C. for 2 min. Aliquots (10 µl) of the PCR reaction were analysed by 1% agarose gel electrophoresis.

A 439 bp-band was clearly detected in peripheral blood lymphocytes (PBL). The amplification of a fragment of aldolase coding sequence was used as control.

The distribution of GPR43 in particular peripheral blood cells, and-other cell types was investigated further using semi-quantitative PCR (FIG. 13). Semi-quantitative RT-PCR (TaqMan) experiments were carried out over a range of 12 selected human tissues using a panel of total and polyA+ RNA (Clontech, Ambion, Biochain). Total RNA from blood cells and cell lines were prepared with (Tripure Isolation Reagent, Boehringer Mannheim).

Semi-quantitative RT-PCR experiments were performed using gene specific primers to human GPR43 receptor. The GPR43 receptor primers were forward 5'-GGCTTTC-CCCGTGCAGTAC-3' (SEQ ID NO: 12), Taqman probe 5'-AGCTCTCCCGCCGGC CTCTG-3' (SEQ ID NO: 13) and reverse 5'-CCAGAGCTGCAATCACTCCA-3' (SEQ ID NO: 14).

Primers designed to the house keeping gene GAPDH forward 5'-GAAGGTGAA GGTCGGAGTC-3' (SEQ ID NO: 15), Taqman probe 5'-AGCTCTCCCGCCG GCCTCTG-3' (SEQ ID NO: 16) and reverse 5'-GAAGATG-GTGATGGGATTTC-3' (SEQ ID NO: 17) were used to produce reference mRNA profiles.

Strong level of GPR43 expression was found in polymorphonuclear neutrophils (PMN).

GPR43 also was detected at lower levels in T lymphocytes and peripheral blood mononuclear cells (PBMC) (FIG. 13). In comparison to the level of expression in the granulocytes no significant expression could be detected in the CNS and other peripheral tissues (data not shown).

Example 3

Screening for GPR43 Ligands

CHO-K1 cells (ATCC CRL-9618 (Bethesda, Md., USA) were grown in Nutrient Mixture HAM's F12 medium supplemented with 10% fetal calf serum, 100 units/ml penicillin and 100 µg/ml streptomycin. A bicistronic plasmid encoding the human GPR43 was transfected into CHO-K1 cells, using Fugene 6 (Roche Diagnostics, Mannheim, Germany). Individual clones were selected two days after transfection with 250 µg/ml zeocin and GPR43-positive clones were confirmed by northern blotting. Positive clones were used for screening with a reference small molecule library containing 250 natural ligands of G protein coupled receptors at a concentration of 1-100 µM. A specific activity was obtained with acetate and confirmed by a dose response curve. Additional related compounds were tested using the same cells.

CHO-K1 cells transfected with the bicistronic plasmid that does not encode the human GPR43 were used as control cells (mock-transfected).

Example 4

Activity of SCFA on CHO-K1 Cells Expressing hGPR43

SCFA, ranging from 1 carbon to 4 carbon, were tested on CHO-K1 cells stably expressing the human GPR43 for their ability to inhibit the activity of adenylate cyclase stimulated with forskolin.

The rank order of potency was as follows: C2 (acetate) ≧C3 (propionate)>C4 (butyrate)>>C1 (formate), with acetate being the most potent to inhibit the enzyme activity. All of these compounds decrease forskolin-stimulated adenylate cyclase activity by 75% (FIG. 4).

Figure 5:
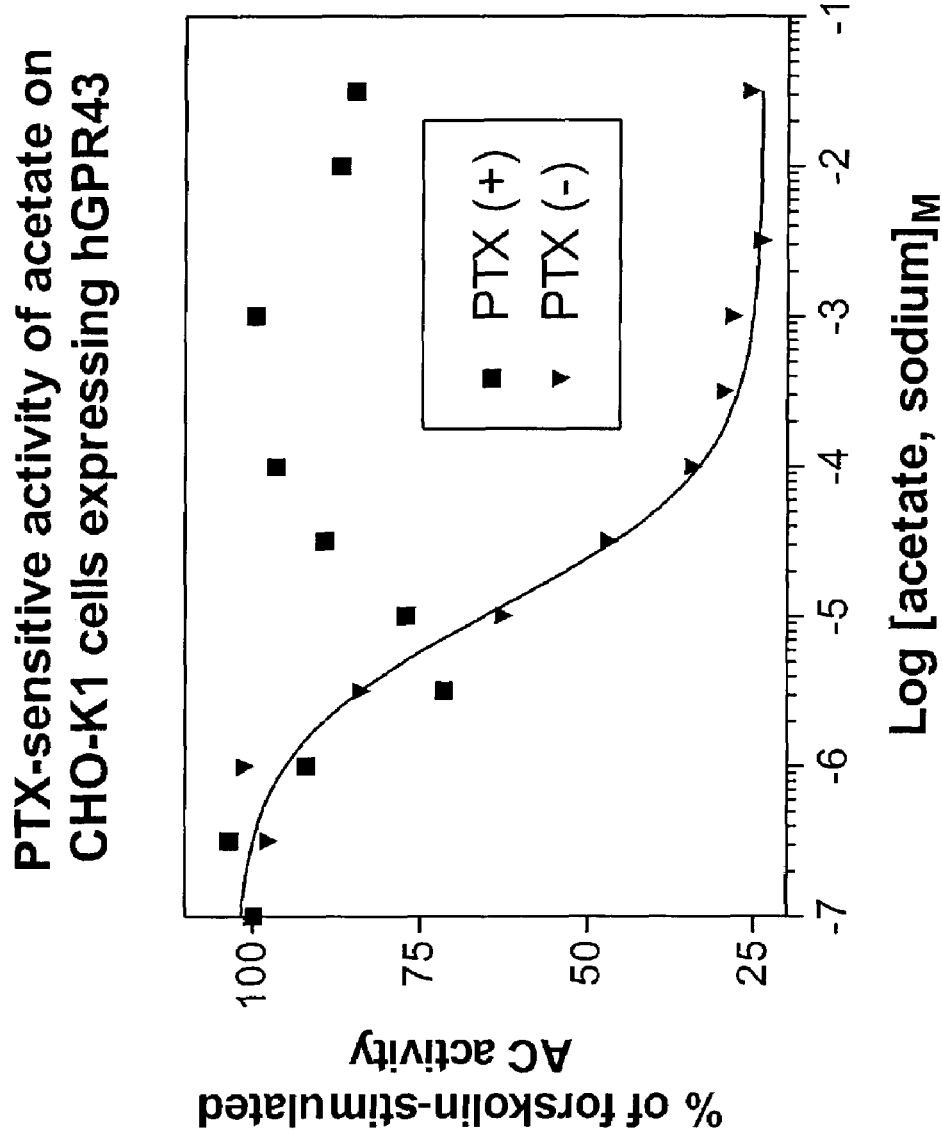
FIG. 5 illustrates the PTX-sensitivity of acetate inhibition of forskolin-stimulated adenylate cyclase activity in CHO-K1 cells stably expressing the human GPR43.

The observed effect of acetate was totally abolished by overnight preincubation with Pertussis Toxin (PTX), which disrupts the coupling between the receptor and the G i/o subunit (FIG. 5). The coupling pathway of the human GPR43 is therefore preferentially Gi in the CHO-K1.

The observed effect of fatty acid was restricted to the GPR43 expressing cells and none of the control cells, expressing other recombinant GPCR or not, showed activity with the activators mentioned (data not shown).

The above-mentioned results are pH-independent. That is, at the concentration tested, the pH of reaction buffer was between 7-7.4. In addition, equipotent activity was observed with different salts of the active SCFA, including ammonium (NH3$^+$), potassium (K$^+$) and sodium (Na$^+$) salts (see FIG. 7 for results obtained with NH3$^+$ acetate).

Example 5

Analysis of SCFA Activity in Membrane-Based Functional Assays

Figure 6:
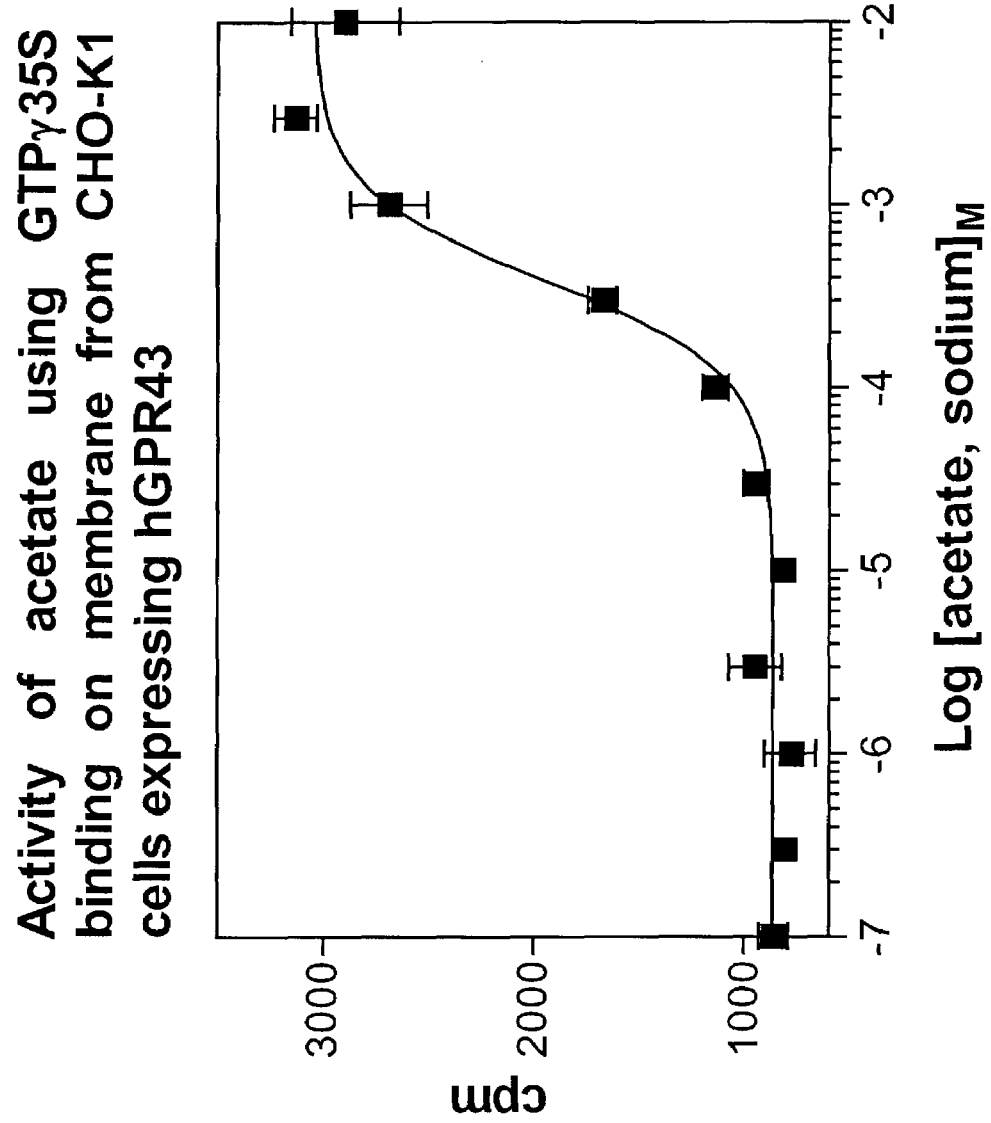
FIG. 6 illustrates the activity of acetate on the accumulation of GTPγ[$^{35}$S] bound to a membrane preparation from CHO-K1 cells stably expressing the human GPR43.

The activity of acetate was examined in a membrane-based functional test. In this assay, the accumulation of GTPγ[$^{35}$S] binding was monitored on a preparation of membranes from CHO-K1 cells expressing the human GPR43 (FIG. 6). The potency of the acetate was comparable to that observed in the cell-based functional assay monitoring cAMP levels. The rank order of potency of the SCFA tested was conserved using this membrane-based assay. That is, the assay showed that C2≧C3>C4>>C1. C4 and C1 partly activate the human receptor since the maximal response was lowest as compared to that observed with acetate and propionate (data not shown).

The activity of acetate, propionate and related compounds was restricted to GPR43 because these acids were not able to stimulate any binding in ten different membrane preparations of CHO-K1 cells expressing non related human G-protein coupled receptors such as adenosine A1 receptor, adrenergic 2C receptor, corticotropin-releasing factor 1 receptor, chemokine CCR3 receptor, leukotriene LTB4 receptor, muscarinic M4 receptor, neuropeptide FF 2S receptor, opioid 3 receptor, serotonin 5-HT1A receptor, and somatostatin sst5 receptor. All of these Gi-coupled receptors were stimulated in the same experiment by their respective reference ligand (data not shown).

Figure 7:
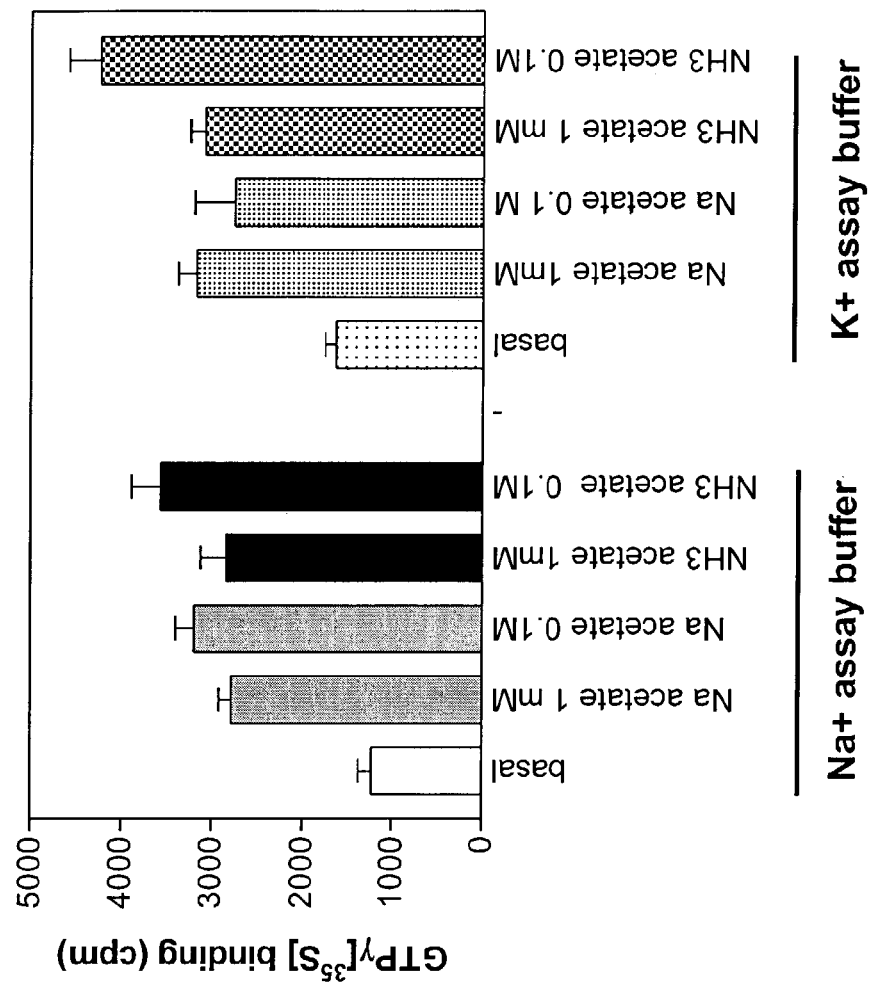
FIG. 7 illustrates the equipotent activity of different salts of acetate on the accumulation of GTPγ[$^{35}$S] bound to a membrane preparation from CHO-K1 cells stably expressing the human GPR43.

The influence of the salt was evaluated to rule out any direct counter-ion effect. In particular, sodium cations are known to modulate, positively or negatively, the activity of G-protein coupled receptors in the presence or absence of ligand. Acetate tested as sodium or ammonium salt was equipotent in activating GTPγ[$^{35}$S] binding on membranes suspended in assay buffer containing 120 mM sodium or potassium (FIG. 7).

Figure 8:
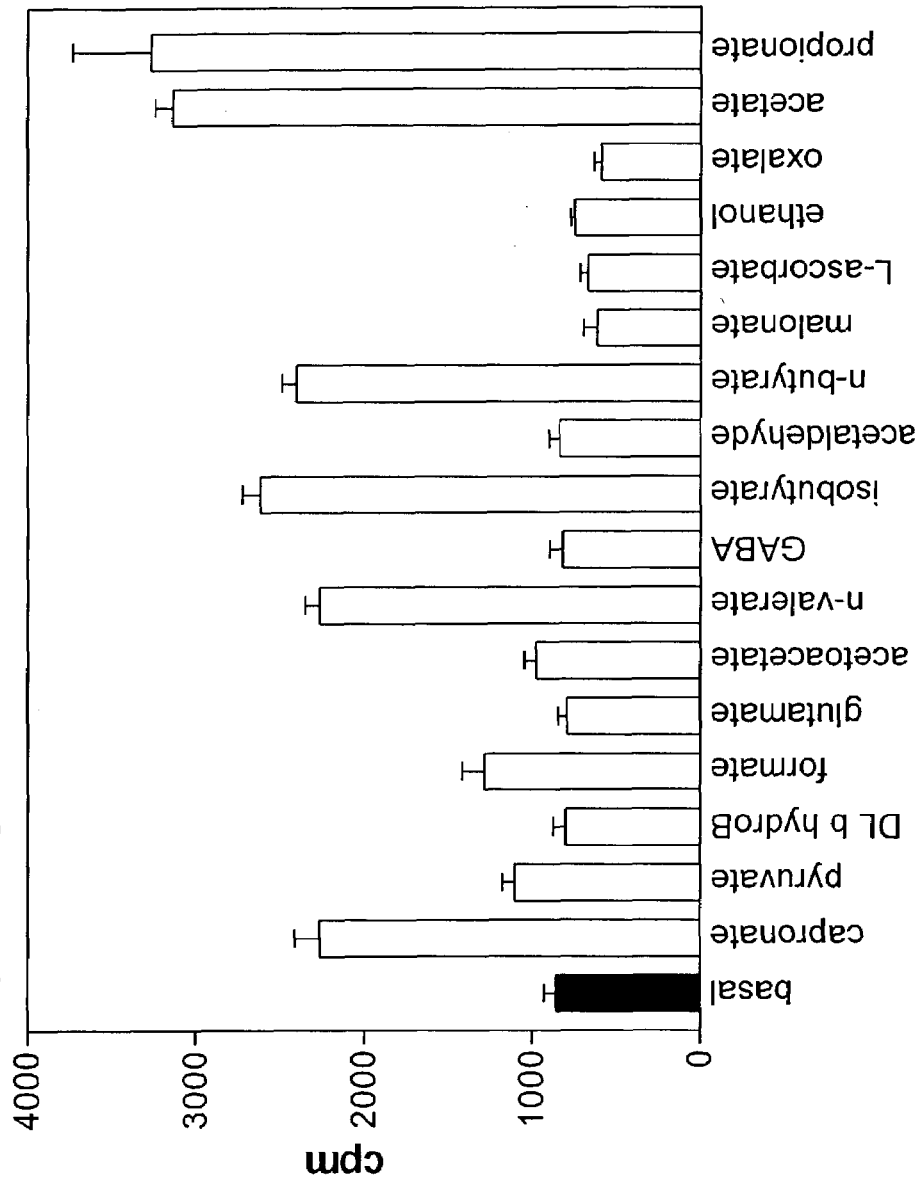
FIG. 8 illustrates the activity of SCFA and related molecules on the accumulation of GTPγ[$^{35}$S] bound to a membrane preparation from CHO-K1 cells stably expressing the human GPR43.

The activity of other SCFA and related compounds (alcohols, aldehydes, cetone, di-acids . . . ) was evaluated using a single concentration of each in the membrane-cell based assay. The order of agonist potency is acetate=propionate>n-butyrate=isobutyrate=n-valerate=caproate>>formate>>pyruvate=acetoacetate. Inactive compounds include: C2—ethanol, acetaldehyde and oxalate; C3—malonate and acetone; C4—DL-β-hydroxybutyrate, GABA, L-glutamate, succinate; and C6—citrate (FIG. 8).

Example 6

Figure 9:
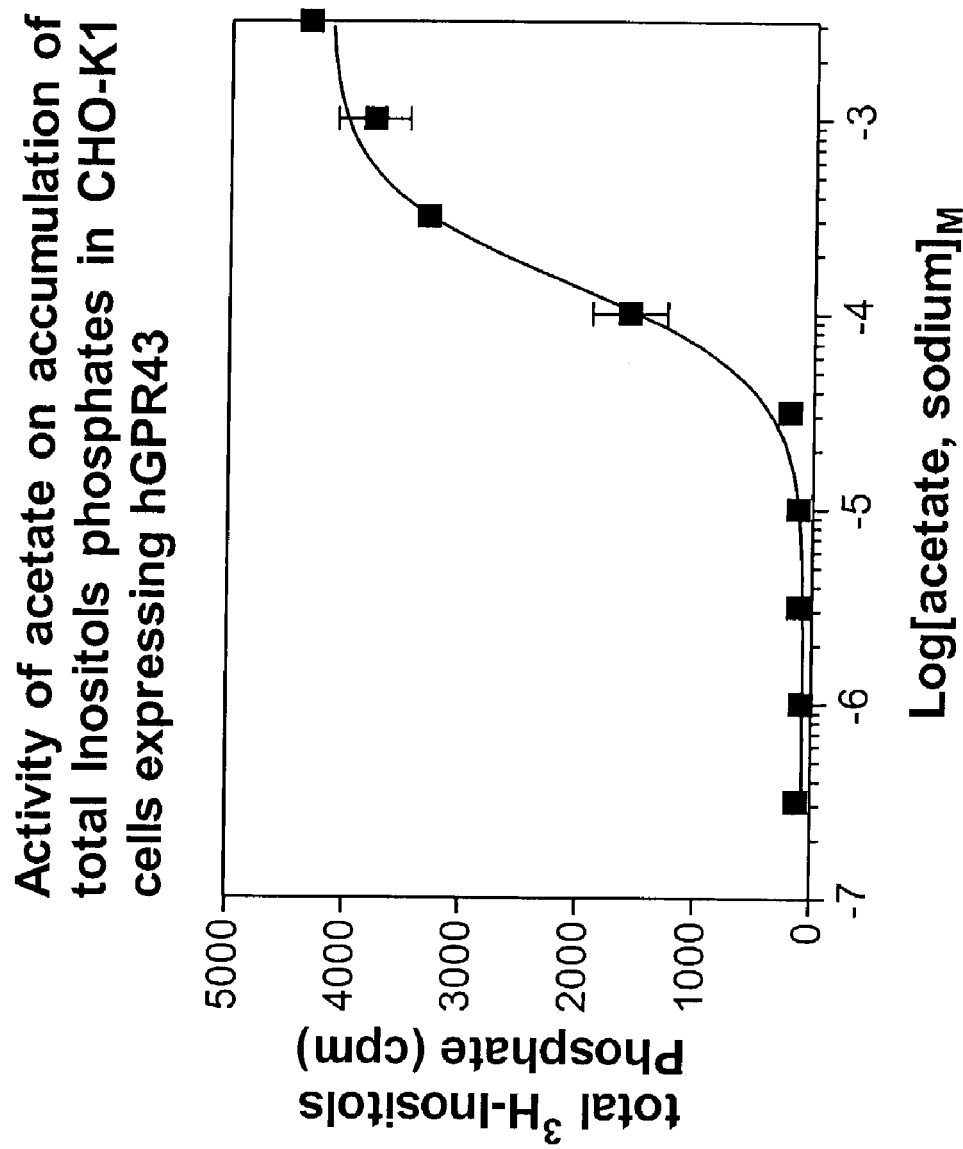
FIG. 9 illustrates the activity of acetate on the accumulation of total inositol phosphates in CHO-K1 cells stably expressing hGPR43.
Figure 10:
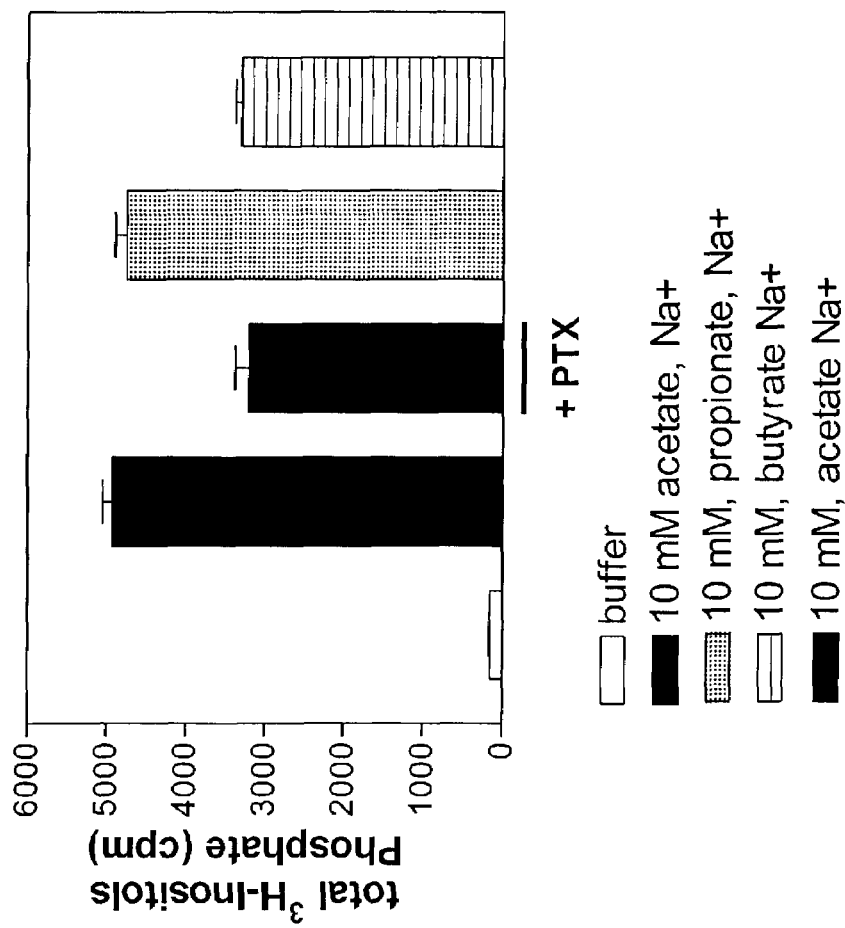
FIG. 10 illustrates the non PTX sensitive-activity of C2, C3 and C4-linear carboxylic acid on the accumulation of total inositol phosphate metabolites on CHO-K1 cells stably expressing the human GPR43.

Effect of SCFA on Activity of GPR43 as Measured by Second Messenger Accumulation SCFA were able to stimulate the production of inositol phosphates in CHO-K1 cells stably expressing human GPR43 (FIG. 9). This activation was slightly affected by a PTX-pretreatment prior to the stimulation, regardless of the SCFA used. The coupling of human GPR43 is therefore dual, involving the activation of Gq protein in addition to the above-described Gi coupling (FIG. 10).

Figure 11:
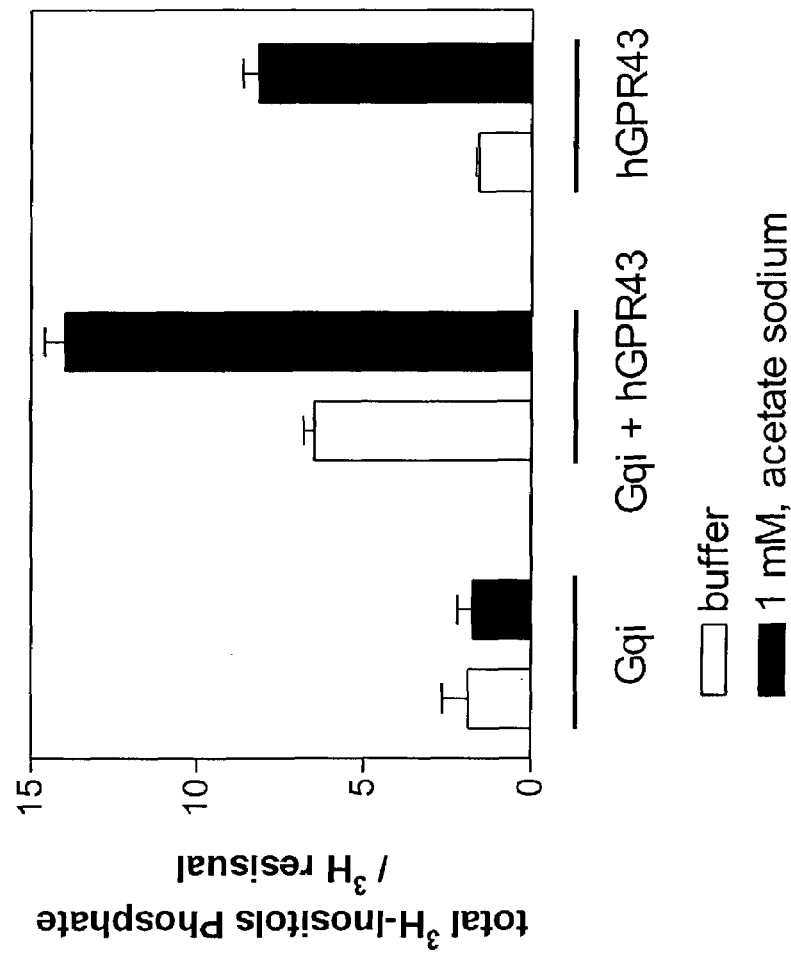
FIG. 11 illustrates the activity of acetate on the accumulation of total inositol phosphate metabolites in COS-7 cells transiently expressing the human GPR43 and/or a chimeric Gα protein.

Transient transfection of the cDNA for human GPR43 into COS-7, CHO and HEK cells, with or without co-expression of a chimeric Gqi protein, led to the fatty acid stimulation of the accumulation of inositol phosphates, reflecting the activation of Phospholipase C (FIG. 11). Control cells, transfected with Gqi only or with cDNAs for other GPCRs, such as motilin or histamine H1 receptor, were not activated by acetate and other SCFAs (data not shown). The accumulation of inositol phosphates was increased in non-SCFA-treated cells transfected with Gqi and human GPR43 cDNAs, giving evidence of the constitutive activation of the receptor in the absence of added ligand at the time of the reaction (FIG. 11).

Example 7

Formulae and Activity of SCFA's Active on GPR43

Formulae of active compounds are presented in FIG. 12. Structure-activity relationships (SRA) of the active compounds showed that, when considered with the inactivity of closely structurally-related compounds (ketones, alcohols and aldehydes), the carboxylic moiety is required for activity, this moiety being branched at the extremity of a carbon chain comprising 1-6 carbon atoms, linear or not, with optimal activity for 2-3 C. A second carboxylic moiety abolished the signal, whatever the length of the carbon chain, as observed with oxalate (C2), malonate (C3), succinate (C4), aspartate (C4), glutamate (C5) or citrate with 3 carboxylic moieties.

Substitutions with other functions differently modulate the activity of compounds on the human GPR43. For example, —OH substitution abolished the activity for a corresponding active compound (n-butyrate is active, β-hydroxybutyrate is not active), while —NH3$^+$ decreased activity without abolishing it (acetate>>glycine). The combination of —OH and —NH3$^+$ functions as in serine (C3) also abolished the activity. Ketone substituted compounds, such as pyruvate and acetoacetate, also showed decreased but consistent activity as compared to corresponding active, non-substituted compounds (acetate and n-butyrate, respectively).

Example 8

Propionate and Acetate are Able to Induce the Mobilization of Intracellular Calcium in Human Neutrophils.

The following experiments were conducted to test whether the human polymorphonuclear (PMN) leukocytes could be activated with acetate and propionate, since the receptor is strongly expressed in peripheral blood cells containing mainly PMNs. Activation was determined by the quantification of the intracellular calcium mobilized from internal pool after activation by acetate and propionate of the cell membrane receptor.

PMN were purified from the venous blood of healthy volunteers. Cells were isolated according to established methods. For intracellular calcium measurements, the cells were loaded for 30 min at room temperature with Fura-2AM (Molecular Probes). Calcium transients were monitored by a LSB 50B spectrofluorimeter (Perkin Elmer). Briefly, neutrophils suspensions (1×107 cells/ml) were incubated with 2 µM Fura-2/AM for 30 minutes at 37° C. The cells were then washed free of the extracellular probe, resuspended at 5×106 cells/ml and allowed to reequilibrate for 10 minutes at 37° C. Cells were then transferred to the thermostatted cuvette compartment (37° C.) of the fluorometer and the fluorescence monitored (excitation and emission wavelengngths, 340 and 510 nm respectively).

Figure 14:
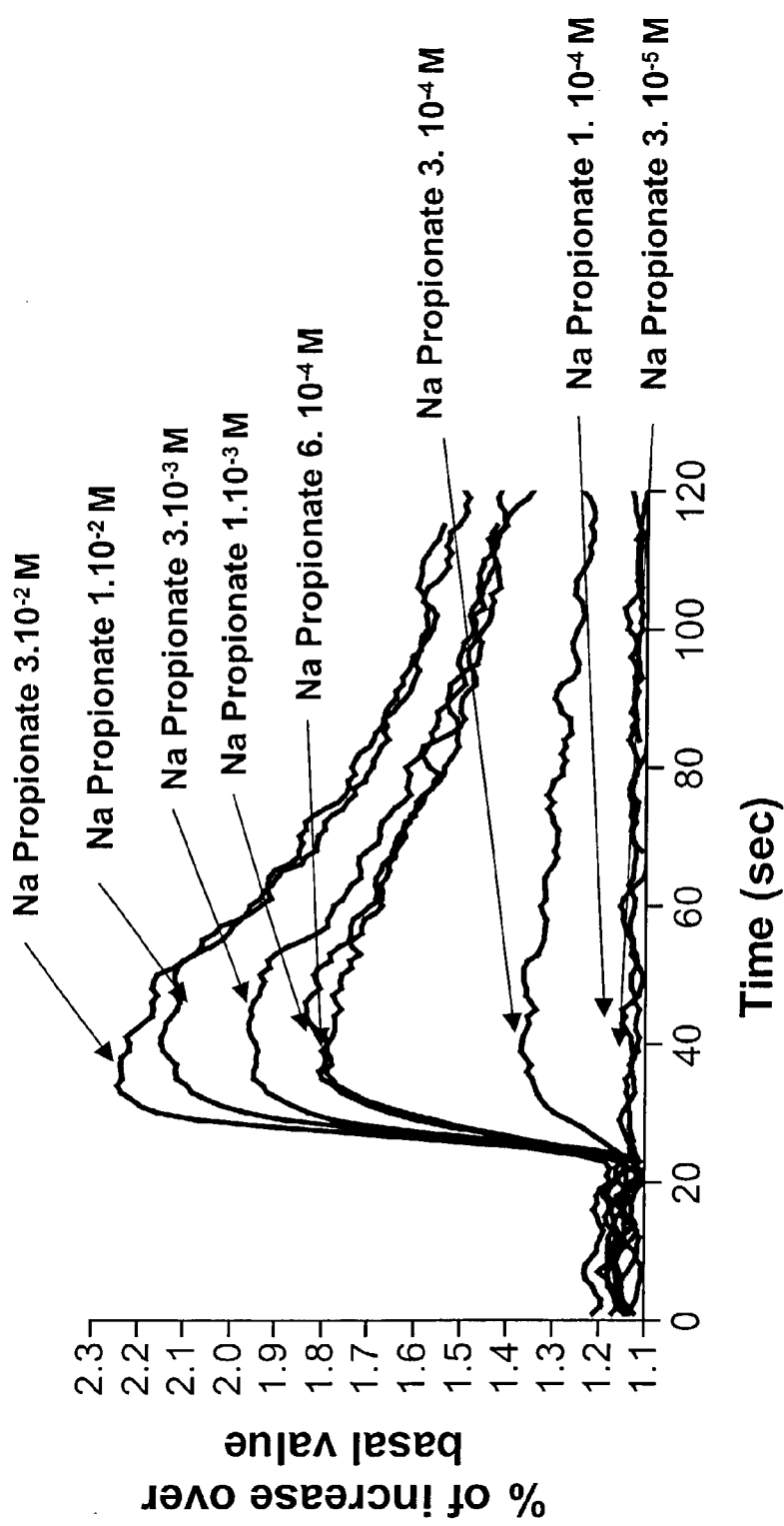
FIG. 14 shows a kinetic plot of the increase of intracellular calcium in PMN for varying concentration of Na propionate.

Injection of propionate or acetate on PMN yields to an increase of intracellular calcium as compared to basal condition. FIG. 14 shows the kinetic plot of such an increase for varying concentration of Na propionate. The increase of intracellular calcium is monitored as an increase of the ratio "basal fluorescence" over "stimulated fluorescence".

Figure 15:
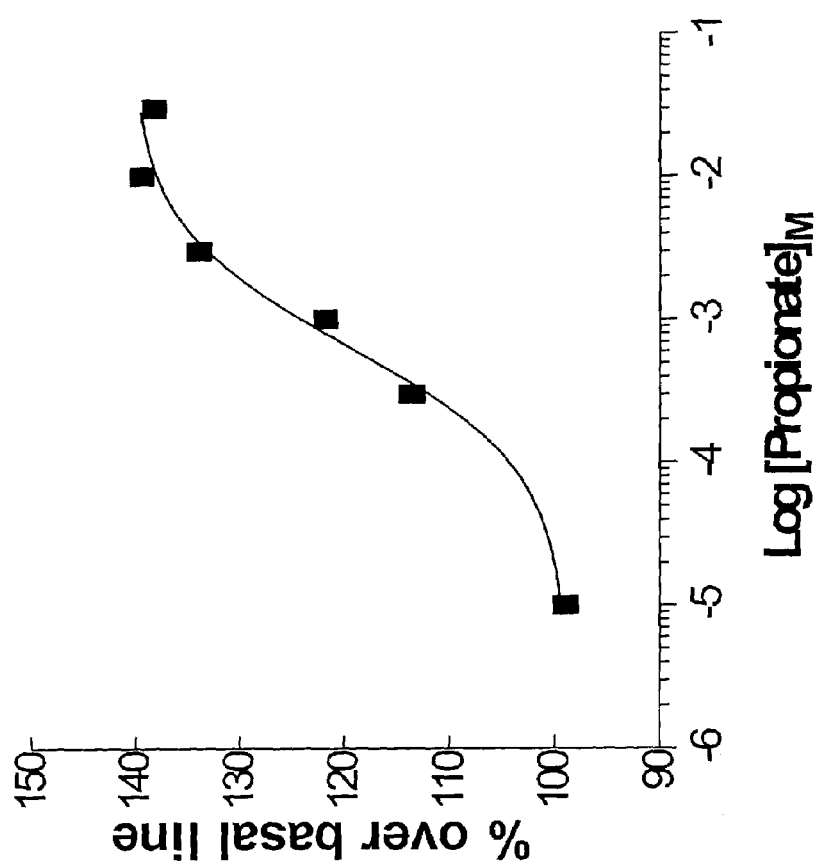
FIG. 15 shows a dose response curve for the stimulation of increased intracellular calcium levels in PMN cells induced by increasing concentrations of Na proprionate.
Figure 16:
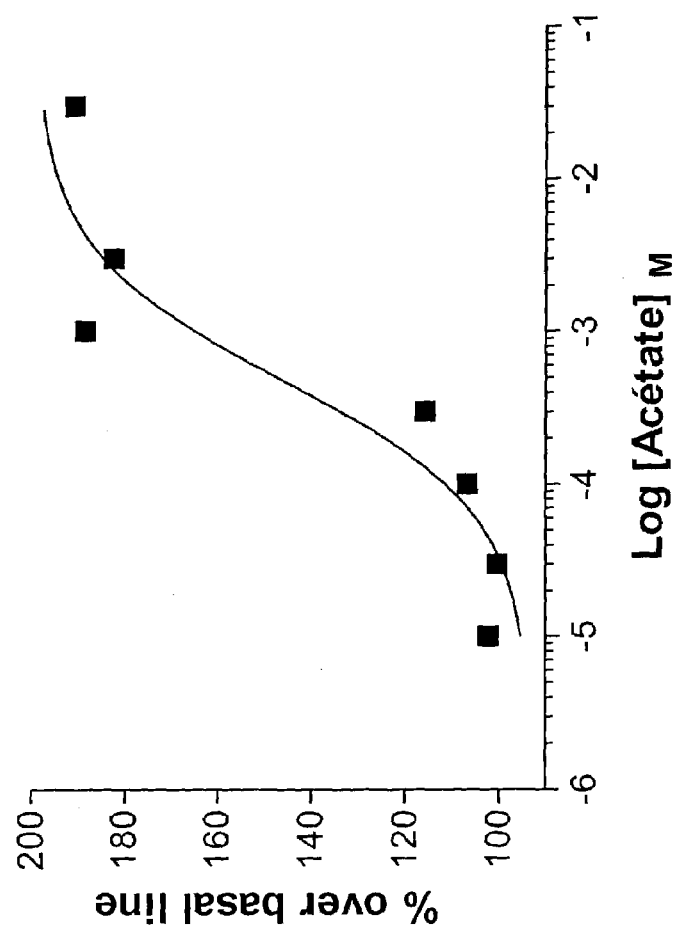
FIG. 16 shows a dose response curve for the stimulation of increased intracellular calcium levels in PMN cells induced by increasing concentrations of Na acetate.

Injection with increasing concentration of propionate (FIG. 15) or acetate (FIG. 16) leads to a concentration-dependent increase of intracellular calcium. Propionate and acetate are equipotent (EC$_{50}$=540 µM and 537 µM, for propionate and acetate respectively).

The results show that propionate and acetate are able to induce the mobilization of intracellular calcium in human neutrophils. According to our previous results describing the complete pharmacological characterization of GPR43 as the cell surface target for short-chain fatty acids such as propionate and acetate, we conclude that the observed effect on calcium mobilization is mediated through the stimulation of the receptor of interest. Naccache et al (J Cell Physiol 1988 Jul.; 136(1):118-24), Fonteriz et al (Biochem Biophys Acta Jun. 7, 1991; 1093 (1): 1-6) and Nakao et al (Infect Immun 1992 Dec.; 60 (12):5307-11) have described that acetate and propionate stimulate the cytoplasmic calcium mobilization in PMN with millimolar EC50. But none of them associated the observed response with the simulation of a given G-protein coupled receptor,(GPCR), although experiments with pertussis toxin and activator/inhibitor of protein kinase C may have suggested a GPCR-mechanism. Brunkhorst et al (Infection and Immunity July 1992, vol 60, 7:2957-2968) has suggested a GPCR mechanism of action, for at least propionate and acetate, on a serie of PMN-activation event such as cytoskeletal F-actin alterations, PMN polarization, F-actin localization, cytoplasmic pH oscillation, cell shape.

We have showed that acetate and propionate were equipotent as activator of recombinant hGPR43 expressed in recombinant system.

We conclude therefore that our data firstly associate that the actions of acetate and propionate on the calcium-mobilization on human neutrophils are mediated through the activation of GPR43 solely.

Example 9

Chemotaxis Induced by SCFAs: Calcium and Chemotactic Assays on Neutrophils:

Peripheral blood mononuclear cells were purified from buffy coats of healthy volunteers as previously described (Struyf S, De Meester I, Scharpe S, Lenaerts J P, Menten P, Wang J M, Proost P, Van Damme J., Eur J Immunol Apr. 28, 1998; 28 (4):1262-71). For intracellular calcium measurements, the cells were loaded for 30 min at room temperature with Fura-2AM (Molecular Probes). Calcium transients were monitored by a LS50B spectrofluorimeter (Perkin Elmer) as described (Grynkiewicz G, Poenie M, Tsien R Y., J Biol Chem Mar. 25, 1985;260(6):3440-50) at a final cell concentration of $10^6$ cells/ml in buffer containing 125 μM probenecid. Chemotaxis was assessed in 48-well chambers using polycarbonate filter membranes with 3 μm (mesh size) (Neuroprobes, Inc.). The results are represented as chemotactic index (FIG. 17).

Chemotactic Response of Neutrophilic Granulocytes to SCFA.:

Freshly isolated peripheral blood neutrophils from healthy donors were tested for their chemotactic response to sodium acetate and propionate. Both SCFAs yielded the classical bell-shaped dose-response curve, the optimal concentration being $10^{-3}$ M (FIG. 17). We conclude that SCFA induce chemotaxis on neutrophils. The potency of SCFAs in neutrophil chemotaxis was inferior to that of fMLP which was still fully active at $10^{-8}$ M. Furthermore, the efficacy of fMLP is also superior to that of SCFA in that the maximal chemotactic index of fMLP was on average at least 3-fold higher (data not shown).

Other Embodiments

The foregoing examples demonstrate experiments performed and contemplated by the present inventors in making and carrying out the invention. It is believed that these examples include a disclosure of techniques which serve to both apprise the art of the practice of the invention and to demonstrate its usefulness. It will be appreciated by those of skill in the art that the techniques and embodiments disclosed herein are preferred embodiments only that in general numerous equivalent methods and techniques may be employed to achieve the same result.

All of the references, including patents and patent applications, identified hereinabove, are hereby expressly incorporated herein by reference to the extent that they describe, set forth, provide a basis for or enable compositions and/or methods which may be important to the practice of one or more embodiments of the present inventions.

The invention claimed is:

1. A method of identifying an agent that modulates the function of GPR43, said method comprising:

(a) contacting a recombinant GPR43 polypeptide comprising the sequence of SEQ ID NO: 2 with a short chain fatty acid in the presence or absence of a candidate modulator under conditions permitting binding of said short chain fatty acid to said GPR43 polypeptide; and (b) measuring binding of said recombinant GPR43 polypeptide to said short chain fatty acid, wherein a decrease in binding in the presence of said candidate modulator, relative to binding in the absence of said candidate modulator, identifies said candidate modulator as an agent that modulates the function of GPR43.

2. A method of detecting, in a sample, the presence of an agent that modulates the function of GPR43, said method comprising (a) contacting a recombinant GPR43 polypeptide comprising the sequence of SEQ ID NO: 2 with a short chain fatty acid in the presence or absence of said sample under conditions permitting binding of said short chain fatty acid to said GPR43 polypeptide; and (b) measuring binding of said recombinant GPR43 polypeptide to said short chain fatty acid, wherein a decrease in binding In the presence of said sample, relative to binding in the absence of said sample, indicates the presence, in said sample of an agent that modulates the function of GPR43.

3. A method of identifying an agent that modulates the function of GPR43, said method comprising:

(a) contacting a recombinant GPR43 polypeptide comprising the sequence of SEQ ID NO: 2 with a short chain fatty acid in the presence or absence of a candidate modulator; and (b) measuring a signalling activity of said recombinant GPR43 polypeptide, wherein a change in the activity in the presence of said candidate modulator relative to the activity in the absence of said candidate modulator identifies said candidate modulator as an agent that modulates the function of GPR43.

4. A method of identifying an agent that modulates the function of GPR43, said method comprising:

(a) contacting a recombinant GPR43 polypeptide comprising the sequence of SEQ ID NO: 2 with a candidate modulator;

(b) measuring a signalling activity of said recombinant GPR43 polypeptide in the presence of said candidate modulator; and (c) comparing said activity measured in the presence of said candidate modulator to said activity measured in a reaction in which said GPR43 polypeptide is contacted with a short chain fatty acid, wherein said candidate. modulator is identified as an agent that modulates the function of GPR43 when the amount of said activity measured in the presence of said candidate modulator is at least 20% of the amount induced by said short chain fatty acid.

5. A method of detecting the presence, in a sample, of an agent that modulates the function of GPR43, said method comprising:

(a) contacting a recombinant GPR43 polypeptide comprising the sequence of SEQ ID NO: 2 with short chain fatty acid in the presence or absence of said sample;

(b) measuring a signalling activity of said recombinant GPR43 polypeptide; and (c) comparing the amount of said activity measured in a reaction containing GPR43 and short chain fatty acid without said sample to the amount of said activity measured in a reaction containing GPR43, short chain fatty acid and said sample, wherein a change in said activity in the presence of said sample relative to the activity in the absence of said sample indicates the presence, in said sample, of an agent that modulates the function of GPR43.

6. A method of detecting the presence, in a sample, of an agent that modulates the function of GPR43, said method comprising:

(a) contacting a recombinant GPR43 polypeptide comprising the sequence of SEQ ID NO: 2 with said sample;

(b) measuring a signalling activity of said recombinant GPR43 polypeptide in the presence of said sample; and (c) comparing said activity measured in the presence of said sample to said activity measured in a reaction in which said GPR43 polypeptide is contacted with a short chain fatty acid, wherein an agent that modulates the function of GPR43 is detected if the amount of said activity measured in the presence of said sample is at least 20% of the amount induced by said short chain fatty acid.

7. The method of any one of claims 1-6 wherein said short chain fatty acid is detectably labeled.

8. The method of claim 7 wherein said short chain fatty acid is detectably labeled with a moiety selected from the group consisting of a radioisotope, a fluorophore, a quencher of fluorescence, an enzyme, and an affinity tag.

9. The method of any one of claims 1-6 wherein said contacting is performed in or on a cell expressing said GPR43 polypeptide.

10. The method of any one of claims 1-6 wherein said contacting is performed in or on synthetic liposomes.

11. The method of any one of claims 1-6 wherein said contacting is performed in or on virus-induced budding membranes containing a GPR43 polypeptide.

12. The method of any one of claims 1-6 wherein said method is performed using a membrane fraction from cells expressing said GPR43 polypepticie.

13. The method of either of claims 1 or 2 wherein said measuring is performed using a method selected from the group consisting of label displacement, surface plasmon resonance, fluorescence resonance energy transfer, fluorescence quenching, and fluorescence polarization.

14. The method of any one of claims 1-6 wherein said agent is selected from the group consisting of a peptide, a polypeptide, an antibody or antigen-binding fragment thereof, a lipid, a carbohydrate, a nucleic acid, and a small organic molecule.

15. The method of any one of claims 3-6 wherein said step of measuring a signalling activity of said GPR43 polypeptide comprises detecting a change in the level of a second messenger.

16. The method of any one of claims 3-6 wherein the step of measuring a signalling activity comprises measurement of guanine nucleotide binding or exchange, adenylate cyclase activity, cAMP, Protein Kinase C activity, phosphatidylinosotol breakdown, diacylglycerol, inositol triphosphate, intracellular calcium, arachinoid acid, MAP kinase activity, tyrosine kinase activity, or reporter gene expression.

17. The method of claim 16 wherein said measuring a signalling activity comprises using an aequorin-based assay.

18. A method for identifying an agent which modulates PMN chemotaxis, comprising (a) contacting a recombinant GPR43 polypeptide comprising the sequence of SEQ ID NO: 2 with a short chain fatty acid in the presence and or absence of a candidate agent under conditions permitting binding of said short chain fatty acid to said recombinant GPR43 polypeptide; and (b) measuring a signalling activity of said recombinant GPR43 polypeptide wherein a change in signalling activity of said GPR43 in the presence of said candidate agent, relative to the signalling activity in the absence of said candidate modulator, identifies said candidate agent as an agent which modulates PMN chemotaxis.

19. A method for identifying an agent which modulates PMN chemotaxis, comprising (a) contacting a recombinant GPR43 polypeptide comprising the sequence of SEQ ID NO: 2 with a short chain fatty acid in the presence or absence of a candidate agent under conditions permitting binding of said short chain fatty acid to said recombinant GPR43 polypeptide; and (b) measuring binding of said recombinant GPR43 polypeptide to said short chain fatty acid, wherein a decrease in binding in the presence of said candidate agent, relative to binding in the absence of said candidate modulator, identifies said candidate agent as an agent that modulates PMN chemotaxis.

20. The method of claim 18 or 19, wherein said recombinant GPR43 polypeptide is present in the cell membrane of a PMN cell.

21. The method of claim 18 or 19, wherein said short chain fatty acid is detectably labeled.

22. The method of claim 21 wherein said short chain fatty acid is detectably labeled with a moiety selected from the group consisting of a radioisotope, a fluorophore, a quencher of fluorescence, an enzyme, and an affinity tag.

23. A method for identifying an agent which modulates PMN chemotaxis, comprising:

(a) contacting a recombinant GPR43 polypeptide comprising the sequence of SEQ ID NO: 2 with a candidate modulator;

(b) measuring a signaling activity of said recombinant GPR43 polypeptide in the presence of said candidate modulator; and (c) comparing said activity measured in the presence of said candidate modulator to said activity measured in a reaction in which said GPR43 polypeptide is contacted with a short chain fatty acid, wherein said candidate modulator is identified as an agent that modulates PMN chemotaxis when the amount of said activity measured in the presence of said candidate modulator is at least 20% of the amount induced by said short chain fatty acid.

24. The method of claim 23, wherein said recombinant GPR43 receptor is present in the cell membrane of a PMN cell.

25. The method of claim 23, wherein said short chain fatty acid is detectably labeled.

26. The method of claim 25 wherein said short chain fatty acid is detectably labeled with a moiety selected from the group consisting of a radioisotope, a fluorophore, a quencher of fluorescence, an enzyme, and an affinity tag.

* * * * *

SEQUENCE LISTING

```
<160> NUMBER OF SEQ ID NOS: 17

<210> SEQ ID NO 1
<211> LENGTH: 993
<212> TYPE: DNA
<213> ORGANISM: Homo sapiens

<400> SEQUENCE: 1
atgctgccgg actggaagag ctccttgatc ctcatggctt acatcatcat cttcctcact      60
ggcctccctg ccaacctcct ggccctgcgg gcctttgtgg ggcggatccg ccagccccag     120
cctgcacctg tgcacatcct cctgctgagc ctgacgctgg ccgacctcct cctgctgctg     180
ctgctgccct tcaagatcat cgaggctgcg tcgaacttcc gctggtacct gcccaaggtc     240
gtctgcgccc tcacgagttt tggcttctac agcagcatct actgcagcac gtggctcctg     300
gcgggcatca gcatcgagcg ctacctggga gtggctttcc ccgtgcagta caagctctcc     360
cgccggcctc tgtatggagt gattgcagct ctggtggcct gggttatgtc ctttggtcac     420
tgcaccatcg tgatcatcgt tcaatacttg aacacgactg agcaggtcag aagtggcaat     480
```

```
gaaattacct gctacgagaa cttcaccgat aaccagttgg acgtggtgct gcccgtgcgg    540
ctggagctgt gcctggtgct cttcttcatc cccatggcag tcaccatctt ctgctactgg    600
cgttttgtgt ggatcatgct ctcccagccc cttgtggggg cccagaggcg gcgccgagcc    660
gtggggctgg ctgtggtgac gctgctcaat ttcctggtgt gcttcggacc ttacaacgtg    720
tcccacctgg tggggtatca ccagagaaaa agccctggt ggcggtcaat agccgtggtg      780
ttcagttcac tcaacgccag tctggacccc ctgctcttct atttctcttc ttcagtggtg    840
cgcagggcat tgggagagg gctgcaggtg ctgcggaatc agggctcctc cctgttggga     900
cgcagaggca aagacacagc agaggggaca aatgaggaca ggggtgtggg tcaaggagaa    960
gggatgccaa gttcggactt cactacagag tag                                 993
```

<210> SEQ ID NO 2
<211> LENGTH: 330
<212> TYPE: PRT
<213> ORGANISM: Homo sapiens

<400> SEQUENCE: 2

```
Met Leu Pro Asp Trp Lys Ser Ser Leu Ile Leu Met Ala Tyr Ile Ile
1               5                   10                  15

Ile Phe Leu Thr Gly Leu Pro Ala Asn Leu Leu Ala Leu Arg Ala Phe
            20                  25                  30

Val Gly Arg Ile Arg Gln Pro Gln Pro Ala Pro Val His Ile Leu Leu
        35                  40                  45

Leu Ser Leu Thr Leu Ala Asp Leu Leu Leu Leu Leu Leu Leu Pro Phe
    50                  55                  60

Lys Ile Ile Glu Ala Ala Ser Asn Phe Arg Trp Tyr Leu Pro Lys Val
65                  70                  75                  80

Val Cys Ala Leu Thr Ser Phe Gly Phe Tyr Ser Ser Ile Tyr Cys Ser
                85                  90                  95

Thr Trp Leu Leu Ala Gly Ile Ser Ile Glu Arg Tyr Leu Gly Val Ala
            100                 105                 110

Phe Pro Val Gln Tyr Lys Leu Ser Arg Arg Pro Leu Tyr Gly Val Ile
        115                 120                 125

Ala Ala Leu Val Ala Trp Val Met Ser Phe Gly His Cys Thr Ile Val
    130                 135                 140

Ile Ile Val Gln Tyr Leu Asn Thr Thr Glu Gln Val Arg Ser Gly Asn
145                 150                 155                 160

Glu Ile Thr Cys Tyr Glu Asn Phe Thr Asp Asn Gln Leu Asp Val Val
                165                 170                 175

Leu Pro Val Arg Leu Glu Leu Cys Leu Val Leu Phe Phe Ile Pro Met
            180                 185                 190

Ala Val Thr Ile Phe Cys Tyr Trp Arg Phe Val Trp Ile Met Leu Ser
        195                 200                 205

Gln Pro Leu Val Gly Ala Gln Arg Arg Arg Arg Ala Val Gly Leu Ala
    210                 215                 220

Val Val Thr Leu Leu Asn Phe Leu Val Cys Phe Gly Pro Tyr Asn Val
225                 230                 235                 240

Ser His Leu Val Gly Tyr His Gln Arg Lys Ser Pro Trp Trp Arg Ser
                245                 250                 255

Ile Ala Val Val Phe Ser Ser Leu Asn Ala Ser Leu Asp Pro Leu Leu
            260                 265                 270

Phe Tyr Phe Ser Ser Ser Val Val Arg Arg Ala Phe Gly Arg Gly Leu
        275                 280                 285
```

```
Gln Val Leu Arg Asn Gln Gly Ser Ser Leu Leu Gly Arg Arg Gly Lys
    290                 295                 300

Asp Thr Ala Glu Gly Thr Asn Glu Asp Arg Gly Val Gly Gln Gly Glu
305                 310                 315                 320

Gly Met Pro Ser Ser Asp Phe Thr Thr Glu
                325                 330

<210> SEQ ID NO 3
<211> LENGTH: 7
<212> TYPE: PRT
<213> ORGANISM: Artificial
<220> FEATURE:
<223> OTHER INFORMATION: Peptide derived from myristoylated alanine-rich
      protein kinase C sybstrate protein MARCKS

<400> SEQUENCE: 3

Phe Lys Lys Ser Phe Lys Leu
1               5

<210> SEQ ID NO 4
<211> LENGTH: 13
<212> TYPE: PRT
<213> ORGANISM: Artificial
<220> FEATURE:
<223> OTHER INFORMATION: Src-releted peptide

<400> SEQUENCE: 4

Arg Arg Leu Ile Glu Asp Ala Glu Tyr Ala Ala Arg Gly
1               5                   10

<210> SEQ ID NO 5
<211> LENGTH: 11
<212> TYPE: DNA
<213> ORGANISM: Unknown
<220> FEATURE:
<223> OTHER INFORMATION: NF-kB binding element consensus sequence

<400> SEQUENCE: 5
ggggactttc c                                                          11

<210> SEQ ID NO 6
<211> LENGTH: 32
<212> TYPE: DNA
<213> ORGANISM: Artificial
<220> FEATURE:
<223> OTHER INFORMATION: GPR43 sense primer

<400> SEQUENCE: 6
gcggaattca ccatgctgcc ggactggaag ag                                   32

<210> SEQ ID NO 7
<211> LENGTH: 31
<212> TYPE: DNA
<213> ORGANISM: Artificial
<220> FEATURE:
<223> OTHER INFORMATION: GPR43 antisense primer

<400> SEQUENCE: 7
ctagtctaga ctgctactct gtagtgaagt c                                    31

<210> SEQ ID NO 8
<211> LENGTH: 20
<212> TYPE: DNA
<213> ORGANISM: Artificial
<220> FEATURE:
```

<223> OTHER INFORMATION: GPR43 sense primer

<400> SEQUENCE: 8
actggaagag ctccttgatc                                          20

<210> SEQ ID NO 9
<211> LENGTH: 19
<212> TYPE: DNA
<213> ORGANISM: Artificial
<220> FEATURE:
<223> OTHER INFORMATION: GPR43 antisense primer

<400> SEQUENCE: 9
caagtattga acgatgatc                                           19

<210> SEQ ID NO 10
<211> LENGTH: 20
<212> TYPE: DNA
<213> ORGANISM: Artificial
<220> FEATURE:
<223> OTHER INFORMATION: Aldolase sense primer

<400> SEQUENCE: 10
ggcaagggca tcctggctgc                                          20

<210> SEQ ID NO 11
<211> LENGTH: 23
<212> TYPE: DNA
<213> ORGANISM: Artificial
<220> FEATURE:
<223> OTHER INFORMATION: Aldolase antisense primer

<400> SEQUENCE: 11
taacgggcca gaacattggc att                                      23

<210> SEQ ID NO 12
<211> LENGTH: 19
<212> TYPE: DNA
<213> ORGANISM: Artificial
<220> FEATURE:
<223> OTHER INFORMATION: GPR43 forward primer

<400> SEQUENCE: 12
ggctttcccc gtgcagtac                                           19

<210> SEQ ID NO 13
<211> LENGTH: 20
<212> TYPE: DNA
<213> ORGANISM: Artificial
<220> FEATURE:
<223> OTHER INFORMATION: Taqman forward probe

<400> SEQUENCE: 13
agctctcccg ccggcctctg                                          20

<210> SEQ ID NO 14
<211> LENGTH: 20
<212> TYPE: DNA
<213> ORGANISM: Artificial
<220> FEATURE:
<223> OTHER INFORMATION: Taqman reverse probe

<400> SEQUENCE: 14
ccagagctgc aatcactcca                                          20

```
<210> SEQ ID NO 15
<211> LENGTH: 19
<212> TYPE: DNA
<213> ORGANISM: Artificial
<220> FEATURE:
<223> OTHER INFORMATION: GAPDH forward primer

<400> SEQUENCE: 15
gaaggtgaag gtcggagtc                                                19

<210> SEQ ID NO 16
<211> LENGTH: 20
<212> TYPE: DNA
<213> ORGANISM: Artificial
<220> FEATURE:
<223> OTHER INFORMATION: GADPH Taqman forward probe

<400> SEQUENCE: 16
agctctcccg ccggcctctg                                               20

<210> SEQ ID NO 17
<211> LENGTH: 20
<212> TYPE: DNA
<213> ORGANISM: Artificial
<220> FEATURE:
<223> OTHER INFORMATION: GAPDH Taqman reverse probe

<400> SEQUENCE: 17
gaagatggtg atgggatttc                                               20
```